(12) United States Patent
Jaffee et al.

(10) Patent No.: US 9,200,036 B2
(45) Date of Patent: Dec. 1, 2015

(54) MESOTHELIN VACCINES AND MODEL SYSTEMS

(75) Inventors: Elizabeth Jaffee, Lutherville, MD (US); Ralph Hruban, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/293,357

(22) Filed: Nov. 10, 2011

(65) Prior Publication Data

US 2012/0076752 A1    Mar. 29, 2012

Related U.S. Application Data

(63) Continuation of application No. 12/049,763, filed on Mar. 17, 2008, now abandoned, which is a continuation-in-part of application No. 10/618,088, filed on Jul. 14, 2003, now abandoned.

(60) Provisional application No. 60/475,783, filed on Jun. 5, 2003, provisional application No. 60/414,931, filed on Sep. 30, 2002, provisional application No. 60/398,217, filed on Jul. 24, 2002, provisional application No. 60/395,556, filed on Jul. 12, 2002, provisional application No. 60/918,267, filed on Mar. 15, 2007.

(51) Int. Cl.
| | |
|---|---|
| *A61K 38/00* | (2006.01) |
| *C07K 14/00* | (2006.01) |
| *C07K 7/06* | (2006.01) |
| *A61K 39/00* | (2006.01) |
| *C07K 16/30* | (2006.01) |
| *C12N 15/85* | (2006.01) |
| *C07K 14/47* | (2006.01) |

(52) U.S. Cl.
CPC .............. *C07K 7/06* (2013.01); *A61K 39/0011* (2013.01); *C07K 16/30* (2013.01); *C12N 15/8509* (2013.01); *A01K 2267/0331* (2013.01); *A61K 2039/505* (2013.01); *A61K 2039/522* (2013.01); *A61K 2039/523* (2013.01); *A61K 2039/53* (2013.01); *A61K 2039/55522* (2013.01); *A61K 2039/6031* (2013.01); *C07K 14/4748* (2013.01); *C12N 2710/16522* (2013.01); *C12N 2740/13043* (2013.01)

(58) Field of Classification Search
None
See application file for complete search history.

(56) References Cited

U.S. PATENT DOCUMENTS

| | | |
|---|---|---|
| 5,320,956 A | 6/1994 | Willingham et al. |
| 5,498,698 A | 3/1996 | Yamaguchi et al. |
| 5,723,318 A | 3/1998 | Yamaguchi et al. |
| 5,763,183 A | 6/1998 | Pesonen et al. |
| 5,795,872 A | 8/1998 | Ricigliano et al. |
| 5,830,463 A | 11/1998 | Duke et al. |
| 5,951,976 A | 9/1999 | Segal |
| 5,981,259 A | 11/1999 | Franzusoff |
| 6,033,674 A | 3/2000 | Jaffee et al. |
| 6,051,237 A * | 4/2000 | Paterson .................... 424/200.1 |
| 6,083,502 A | 7/2000 | Pastan et al. |
| 6,153,430 A | 11/2000 | Pastan et al. |
| 6,171,777 B1 | 1/2001 | Cook et al. |
| 6,224,868 B1 | 5/2001 | Wong et al. |
| 6,270,795 B1 | 8/2001 | Jones et al. |
| 6,350,445 B1 | 2/2002 | Jaffee et al. |
| 6,358,933 B1 | 3/2002 | Aguilar Rubido et al. |
| 6,384,018 B1 | 5/2002 | Content et al. |
| 6,448,086 B1 | 9/2002 | Khosravi et al. |
| 6,472,375 B1 | 10/2002 | Hoon et al. |
| 6,475,995 B1 | 11/2002 | Roy et al. |
| 6,488,926 B1 | 12/2002 | Khan et al. |
| 6,495,143 B2 | 12/2002 | Lee et al. |
| 6,500,432 B1 | 12/2002 | Dalemans et al. |
| 6,770,445 B1 * | 8/2004 | Scholler et al. ................. 435/7.1 |
| 7,375,183 B1 * | 5/2008 | Pastan et al. ................... 530/350 |
| 2002/0019331 A1 | 2/2002 | Cheever et al. |
| 2002/0034753 A1 | 3/2002 | Yang et al. |
| 2002/0051990 A1 | 5/2002 | Ople et al. |
| 2003/0211498 A1 | 11/2003 | Morin et al. |
| 2004/0037840 A1 | 2/2004 | Beier et al. |
| 2005/0249748 A1 | 11/2005 | Dubensky, Jr. et al. |

FOREIGN PATENT DOCUMENTS

| | | |
|---|---|---|
| EP | 0 517 925 A1 | 12/1992 |
| EP | 0 621 285 A1 | 10/1994 |
| JP | 11-502710 A | 3/1999 |
| WO | 93/13132 A1 | 7/1993 |
| WO | 94/10312 A1 | 5/1994 |
| WO | 96/30514 A1 | 10/1996 |
| WO | 97/24132 A1 | 7/1997 |
| WO | 97/25068 A2 | 7/1997 |
| WO | 98/53319 A2 | 11/1998 |
| WO | 99/28471 A2 | 6/1999 |

(Continued)

OTHER PUBLICATIONS

Sensi et al., "Intralesional Selection of T Cell Clonotypes in the Immune Response to Melanoma Antigens Occurring During Vaccination," Journal of Immunotherapy, May 1998, vol. 21, No. 3, pp. 198-204.

(Continued)

*Primary Examiner* — Michail Belyavskyi
(74) *Attorney, Agent, or Firm* — Banner & Witcoff, Ltd.

(57) ABSTRACT

Mesothelin can be used as an immunotherapeutic target. It induces a cytolytic T cell response. Portions of mesothelin which induce such responses are identified. Vaccines can be either polynucleotide- or polypeptide-based. Carriers for raising a cytolytic T cell response include bacteria and viruses. A mouse model for testing vaccines and other antitumor therapeutics and prophylactics comprises a strongly mesothelin-expressing, transformed peritoneal cell line.

7 Claims, 24 Drawing Sheets

(56) References Cited

FOREIGN PATENT DOCUMENTS

| WO | 00/20027 A2 | 4/2000 |
|---|---|---|
| WO | 00/36107 A2 | 6/2000 |
| WO | 00/50900 A2 | 8/2000 |
| WO | 00/73346 A1 | 12/2000 |
| WO | 01/18046 A2 | 3/2001 |
| WO | 01/57270 A2 | 8/2001 |
| WO | 01/57271 A2 | 8/2001 |
| WO | 01/92581 A2 | 12/2001 |
| WO | 02/00677 A1 | 1/2002 |
| WO | 02/055705 A2 | 7/2002 |
| WO | 02/068677 A2 | 9/2002 |
| WO | 02/101075 A2 | 12/2002 |
| WO | 02/102235 A2 | 12/2002 |
| WO | 03/014322 A2 | 2/2003 |
| WO | 03/042661 A2 | 5/2003 |
| WO | 03/050243 A2 | 6/2003 |
| WO | 2006/076678 A2 | 7/2006 |

OTHER PUBLICATIONS

Berd et al., "Induction of Cell-Mediated Immunity to Autologous Melanoma Cells and Regression of Metastases After Treatment With a Melanoma Cell Vaccine Preceded by Cyclophosphamide," Cancer Research, May 1986, vol. 46, pp. 2573-2577.

Hoon et al., "Suppressor Cell Activity in a Randomized Trial of Patients Receiving Active Specific Immunotherapy with Melanoma Cell Vaccine and Low Dosages of Cyclophosphamide," Cancer Research, Sep. 1, 1990, vol. 50, pp. 5358-5364.

Fischereder et al., "Immortalization and Characterization of Human Peritoneal Mesothelial Cells," Kidney International, Jun. 1997, vol. 51, No. 6, pp. 2006-2012.

Mazurek et al., "Metabolic Cooperation Between Different Oncogenes During Cell Transformation: Interaction Between Activated RAS and HPV-16 E7," Oncogene, Oct. 18, 2001, vol. 20, No. 47, pp. 6891-6898.

Argani, et al., "Discovery of New Markers of Cancer Through Serial Analysis of Gene Expression: Prostate Stem Cell Antigen is Overexpressed in Pancreatic Adenocarcinoma," Jun. 1, 2001, Cancer Research 61:4320-4324.

Chang, et al., "Isolation and Characterization of a Monoclonal Antibody, K1, Reactive With Ovarian Cancers and Normal Mesothelium," 1992, Int. J. Cancer 50 (3):373-381.

Chang, et al., "Characterization of the Antigen (CAK1) Recognized by Monoclonal Antibody K1 Present on Ovarian Cancers and Normal Mesothelium," Jan. 1, 1992, Cancer Research 52:181-186.

Chang, et al., "Molecular Cloning of Mesothelin, A Differentiation Antigen Present on Mesothelium, Mesotheliomas, and Ovarian Cancers," Jan. 1996, PNAS USA 93:136-140.

Hough, et al., "Large-Scale Serial Analysis of Gene Expression Reveals Genes Differentially Expressed in Ovarian Cancer," Nov. 15, 2000, Cancer Research 60:6281-6287.

Jaffee, et al., "Novel Allogeneic Granulocyte-Macrophage Colony-Stimulating Factor-Secreting Tumor Vaccine for Pancreatic Cancer: A Phase I Trial of Safety and Immune Activation," Jan. 1, 2001, Journal of Clinical Oncology 19(1):145-156.

Kojima, et al., "Molecular Cloning and Expressing of Megakaryocyte Potentiating Factor cDNA," 1995, The Journal of Biological Chemistry 270(37):21984-21990.

Schafer, et al., "Induction of a Cellular Immune Response to a Foreign Antigen by a Recombinant *Listeria monocytogenes* Vaccine," Jul. 1, 1992 J. Immunology, 149(1):53-59.

Suarez-Alvarez, et al., "Circulating IgG Response to Stromelysin-3, Collagenase-3, Galectin-3 and Mesothelin in Patients with Pharynx/Larynx Squamous Cell Carcinoma," 2001, Anticancer Research 21:3677-3684.

Waanders, et al., "Melanoma-Reactive Human Cytotoxic T Lymphocytes Derived from Skin Biopsies of Delayed-Type Hypersensitivity Reactions Induced by Injection of an Autologous Melanoma Cell Line," May 1997, Clinical Cancer Research 3:685-696.

Yamaguchi, et al., "A Novel Cytokine Exhibiting Megakaryocyte Potentiating Activity From a Human Pancreatic Tumor Cell Line HPC-Y5," 1994, The Journal of Biological Chemistry 269(2):805-808.

Angelakopoulos et al., "Safety and Shedding of an Attenuated Strain of *Listeria monocytogenes* with a Deletion of actA/plcB in Adult Volunteers: a Dose Escalation Study of Oral Inoculation", Infection and Immunity, Jul. 2002, pp. 3592-3601, vol. 70, No. 7.

Argani et al., "Mesothelin is Overexpressed in the Vast Majority of Ductal Adenocarcinomas of the Pancreas: Identification of a New Pancreatic Cancer Marker by Serial Analysis of Gene Expression (SAGE)", Clinical Cancer Research, Dec. 2001, pp. 3862-3868, vol. 7.

Arrington et al., "Plasmid Vectors Encoding Cholera Toxin or the Heat-Labile Enterotoxin from *Escherichia coli* are Strong Adjuvants fro DNA Vaccines", Journal of Virology, May 2002, pp. 4536-4546, vol. 76, No. 9.

Baltz, "Vaccines in the treatment of cancer", Am J Health-Syst Pharm, Nov. 15 1995, pp. 2574-2585, vol. 52.

Bera et al., "Mesothelin is Not Required for Normal Mouse Development or Reproduction", Molecular and Cellular Biology, Apr. 2000, pp. 2902-2906, vol. 20, No. 8.

Chang et al., "Flavivirus DNA Vaccines Current Status and Potential", Ann New York Acad Sci., Dec. 2001, pp. 272-285, vol. 951.

Chowdhury et al., "Analysis of cloned Fvs from a phage display library indicates that DNA immunization can mimic antibody response generated by cell immunizations", JIM, 1999, pp. 83-91, vol. 231.

Chowdhury et al., "Generation of high titer antisera in rabbits by DNA immunization", JIM, 2001, pp. 147-154, vol. 249.

Chowdhury et al., "Isolation of a high-affinity stable single-chain Fv specific for mesothelin from DNA-immunized mice by phage display and construction of a recombinant immunotoxin with anti-tumor activity", Proc. Natl. Acad. Sci. USA, Jan. 1998, pp. 669-674, vol. 95.

Cohen et al., "Modulating the immune response to genetic immunization", The FASEB Journal, Dec. 1998, pp. 1611-1626, vol. 12.

Darji et al., Oral Somatic Transgene Vaccination Using Attenuated *S. typhimurium*, Cell, Dec. 12 1997, pp. 765-775, vol. 91.

Darji et al., "Oral delivery of DNA vaccines using attenuated *Salmonella typhimurium* as carrier", FEMS Immunology and Medical Microbiology, 2000, pp. 341-349, vol. 27.

Glomski et al., "The *Listeria monocytogenes* hemolysin has an acidic pH optimum to compartmentalize activity and prevent damage to infected host cells", The Journal of Cell Biology, Mar. 18 2002, pp. 1029-1038, vol. 156, No. 6.

Gunn et al., "Two *Listeria monocytogenes* Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16", The Journal of Immunology, 2001, pp. 6471-6479, vol. 167.

Hellström et al., "Tumor Immunology: An Overview", Ann. New York Acad. Sci., 1993, pp. 24-33, vol. 690.

Lauer et al., "Construction, Characterization, and Use of Two *Listeria monocytogenes* Site-Specific Phage Integration Vectors", Journal of Bacteriology, Aug. 2002, pp. 4177-4186, vol. 184, No. 15.

Liau et al., "Tumor Immunity within the Central Nervous System Stimulated by Recombinant *Listeria monocytogenes* Vaccination", Cancer Research, Apr. 15, 2002, pp. 2287-2293, vol. 62.

Makitalo et al., "ELISpot and ELISA analysis of spontaneous, mitogen-induced and antigen-specific cytokine production in cynomolgus and rhesus macaques", JIM, 2002, pp. 85-97, vol. 270.

Medina et al., "Use of live bacterial vaccine vectors for antigen delivery: potential and limitations", Vaccine, 2001, pp. 1573-1580, vol. 19.

Pan et al., "Regressin of Established B16F10 Melanoma with a Recombinant *Listeria monocytogenes* Vaccine", Cancer Research, Oct. 15, 1999, pp. 5264-5269, vol. 59.

Poland et al., "Science, medicine, and the future New vaccine development", BMJ, Jun. 2002, pp. 1315-1319, vol. 324.

Portnoy et al., "The cell biology of *Listeria monocytogenes* infection: the intersection of bacterial pathogenesis and cell-mediated immunity", JCB, Aug. 5, 2002, pp. 409-414, vol. 158, No. 3.

(56) References Cited

OTHER PUBLICATIONS

Rubio-Godoy et al., "Discrepancy between ELISPOT IFN-γ secretion and binding of A2/peptide multimers to TCR reveals interclonal dissociation of CTL effector function from TCR-peptide/MHC complexes half-life", Proc. Natl. Acad. Sci. USA, Aug. 28, 2001, pp. 10302-10307, vol. 98, No. 18.
Ryu et al., "Relationships and Differentially Expressed Genes among Pancreatic Cancers Examined by Large-scale Serial Analysis of Gene Expression", Cancer Research, Feb. 1, 2002, pp. 819-826, vol. 62.
Scholler et al., "Soluble member(s) of the mesothelin/megakaryocyte potentiating factor family are detectable in sera from patients with ovarian carcinoma", Proc. Natl. Acad. Sci. USA, Sep. 1999, pp. 11531-11536, vol. 96.
Shen et al., "Compartmentalization of Bacterial Antigens: Differential Effects on Priming of CD8 T Cells and Protective Immunity", Cell, Feb. 20, 1998, pp. 535-545, vol. 92.
Shen et al., "Recombinant *Listeria monocytogenes* as a live vaccine vehicle for the induction of protective anti-viral cell-mediated immunity", Proc. Natl. Acad. Sci. USA, Apr. 1995, pp. 3987-3991, vol. 92.
Stubbs et al., "Whole recombinant yeast vaccine activates dendritic cells and elicits protective cell-mediated immunity", Nature Medicine, May 2001, pp. 625-629, vol. 7, No. 5.
Vecino et al., "Mucosal DNA vaccination with highly attenuated *Shigella* is superior to attenuated *Salmonella* and comparable to intramuscular DNA vaccination for T cells against HIV", Immunology Letters, 2002, pp. 197-204, vol. 82.
Ward et al., "Immunotherapeutic potential of whole tumour cells", Cancer Immunology, 2002.
Weiss et al., "Transfer of eukaryotic expression plasmids to mammalian host cells by bacterial carriers", Current Opinion in Biotechnology, 2001, pp. 467-472, vol. 12.
Arrington et al., "Plasmid vectors encoding cholera toxin or the heat-labile enterotoxin from *Escherichia coli* are strong adjuvants for DNA vaccines", J Virol May 2002; 76(9):4536-46 (Abstract only).
Arvilommi H., "ELISPOT for detecting antibody-secreting cells in response to infections and vaccination", APMIS Jun. 1996; 104(6):401-10 (Abstract only).
Hassan et al, Eur. J. Can. 44:46-53 (2008).
Hung et al., Vaccine 25:127-135 (2007).
Hung et al., Gene Therapy 14:921-929 (2007).
Change et al., Gene Therapy 14:1189-1198 (2007).
Dubensky et al., J. Immunother. 29(6) Abstract (2006).
Li et al., J. Immunother. 29(6) Abstract (Nov./Dec. 2006).
Yokokawa et al., Clin. Cancer Res. 11(17):6342-6351 (2005).
Blattman et al., Science: 200-205 (2004).
Bruhn et al., Microbes & Infect. XX: 1-11 (2007).
Daudel et al., Expert. Rev. Vaccines 6(1): 97-110 (2007).
Pardoll, Nature Immunology 2:227-238 (2002).
Laheru et al., ASCO Mtg 2007 Gastrointestinal Cancers Symposium Abstract No. 106.
Voskoglou-Nomikos, (Clin. Can. Res. (:4227-4239(2003)).
Dennis, (Nature 442:739-741 (2006)).
Ayyoub et al., J. Immunol. 172:7206-7211 (2004).
Glick (Gen. Engineer. News 28(&) pp. 6 and 9 (Apr. 1, 2008).
Biijer et al., (Expert Rev. Vaccines 6($):591-603 (2007)).
Lin et al., "Treatment of Established Tumors with a Novel Vaccine that Enhances Major Histocompatibility Class II Presentation of Tumor Antigen," Cancer Research, Jan. 1, 1996, vol. 56, pp. 21-26.
Quan, et al. Disease-a-Month, 1997. vol. 43, pp. 745-808.
Weiskirch and Paterson. *Listeria monocytogenes*: a potent vaccine vector for neoplastic and infectious disease. Immunological Reviews, 1997. vol. 158, pp. 159-169.
Schirle, Weinschenk, and Stevanovic. Combining computer algorithms with experimental approaches permits the rapid and accurate identification of T cell epitopes from defined antigens. Journal of Immunological Methods, 2001. vol. 257, pp. 1-16.
Bodey, Bodey, Siegel, and Kaiser. Failure of cancer vaccines: the significant limitations of this approach to immunotherapy. Anticancer Research, 2000. vol. 20, pp. 2665-2676.
Lee, Wang, Nielsen, Wunderlich, Migueles, Connors, Steinberg, Rosenberg, and Marincola. Increased vaccine-specific T cell frequency after peptide-based vaccination correlates with increased susceptibility to in vitro stimulation but does not lead to tumor regression. Journal of Immunology, 1999. vol. 163, pp. 6292-6300.
Forni, Lollini, Musiani, and Colombo. Immunoprevention of cancer: is the time ripe? Cancer Research, 2000. vol. 60, pp. 2571-2575.
Gura. Systems for identifying new drugs are often faulty. Science, 1997. vol. 278, pp. 1041-1042.
De Gruijl and Curiel. Cancer vaccine strategies get bigger and better. Nature Medicine, 1999. vol. 5, pp. 1124-1125.
Chatterjee, Foon, and Kohler. Idiotypic antibody immunotherapy of cancer. Cancer Immunology Immunotherapy, 1994. vol. 38, pp. 75-82.
Kellan D, "Of mice and men: values and liabilities of the athymic nude mouse model in anticancer drug development," European Journal of Cancer, 2004, vol. 40, pp. 827-836.
Verma and Somia, "Gene therapy—promises, problems, and prospects," Nature, 1997, vol. 389, pp. 239-242.
Pfeifer and Verma, "Gene therapy: promises and problems," Annual Reviews in Genomics and Human Genetics, 2001. vol. 2, pp. 177-211.
Vile, Russell, and Lemoine, "Cancer gene therapy: hard lessons and new courses," Gene Therapy, 2000, vol. 7, pp. 2-8.
Li et al., Lancet 363: 1049-105 (2004).
Hassan et al., Clin. Can. Res. 10:3937-3942 (2004).
Azevedo et al.; "Main Features of DNA-based immunization vectors."; Brazilian Journal of Medical and Biological Research; vol. 32; No. 2; Feb. 1999; Abstract.
Morrow et al., "Recombinant viruses as vectors for mucosal immunity", Curr Top Microbiol Immunol 1999;236:255-73 (Abstract only).
Poland et al., "New vaccine development", BMJ Jun. 1, 2002;324(7349):1315-9 (Abstract only).
Polo et al., "Alphavirus DNA and particle replicons for vaccines and gene therapy", Dev Biol (Basel) 2000;104:181-5 (Abstract only).
Prazeres et al., "Purification of plasmids for gene therapy and DNA vaccination", Biotechnol Annu Rev 2001;7:1-30 (Abstract Only).
Lindsley et al., "Immunoprophylaxis of hepatitis C virus infection", Clin Liver Dis Nov. 2001;5(4):1091-103 (Abstract Only).
Ramsay et al., "Genetic vaccination strategies for enhanced cellular, humoral and mucosal immunity", Immunol Rev Oct. 1999;171:27-44 (Abstract Only).
Reimann et al., "DNA vaccines", Vox Sang 2000;78 Suppl 2:57-60 (Abstract Only).
Restifo et al., "The promise of nucleic acid vaccines", Gene Ther Jan. 2000;7(2):89-92 (Abstract Only).
Ryu et al., "Relationships and differentially expressed genes among pancreatic cancers examined by large-scale serial analysis of gene expression", Cancer Res Feb. 1, 2002;62(3):819-26 (Abstract Only).
Schirmbeck et al., "Revealing the potential of DNA-based vaccination: lessons learned from the hepatitis B virus surface antigen", Biol Chem Apr. 2001;382(4):543-52 (Abstract Only).
Schmittel et al., "Quantification of tumor-specific T lymphocytes with the ELISPOT assay", J Immunother May-Jun. 2000;23(3):289-95 (Abstract Only).
Suarez-Alvarez et al., "Circulating IgG response to stromelysin-3, collagenase-3, galectin-3 and mesothelin in patients with pharynx/larynx squamous cell carcinoma", Anticancer Res Sep.-Oct. 2001;21(5):3677-84 (Abstract Only).
Sundaram et al., "Synthetic peptides as cancer vaccines", Biopolymers 2002;66(3):200-16 (Abstract Only).
Vecino et al., "Mucosal DNA vaccination with highly attenuated *Shigella* is superior to attenuated *Salmonella* and comparable to intramuscular DNA vaccination for T cells against HIV", Immunol Lett Jul. 3, 2002;82(3):197-204 (Abstract Only).
Ward et al., "Immunotherapeutic potential of whole tumour cells", Cancer Immunol Immunother Sep. 2002;51(7):351-7 (Abstract Only).
Westwater et al., "Development of a P1 phagemid system for the delivery of DNA into Gram-negative bacteria", Microbiology Apr. 2002;148(Pt 4):943-50 (Abstract Only).

(56) References Cited

OTHER PUBLICATIONS

Wlazlo et al., "DNA tumor vaccines", Arch Immunol Ther Exp (Warsz) 2001;49(1):1-11 (Abstract Only).

Yamashita et al., "Mapping and determination of the cDNA sequence of the Erc gene preferentially expressed in renal cell carcinoma in the Tsc2 gene mutant (Eker) rat model", Biochem Biophys Res Commun Aug. 18, 2000;275(1):134-40 (Abstract Only).

Zoller et al., "Active vaccination after allogeneic bone marrow cell transplantation: a new option in the Immunotherapy of cancer?", Arch Immunol Ther Exp (Warsz) 2002;50(3):197-224 (Abstract Only).

Anderson et al., Tissue Antigens, Jun. 2000;55(6):519-531.

Feltkamp et al., Mol. Immunol. Dec. 1994; 31(18):1391-1401.

Ezzell, J. NIH Res., 1995, 7:46-49.

Thomas et al., J. Exp. Med. 200(3):297-306 (2004).

Laheru et al., AACR-NCI-EORTC International Conference.Molecular Targets and Cancer Therapeutics, Nov. 14-18, 200S, Philadelphia, PA, Clin. Cancer Res. 2005; 11(24 Suppl) Dec. 15, 2005 (pp. 1-2).

Boeck et al., Onkologie, Feb. 2007; 30(1-2):39-42, Epub, Jan. 26, 2007 (Abstract only).

Brockstedt et al., Spore Poster CRS-207 (pp. 1-14), 1995.

Chen et al., Cancer 110(2):421-431 (2007).

Clincaltrials.gov (VAC07001), 2001.

Bera TK et al., "Mesothelin is not required for normal mouse development or reproduction", Mol Cell Biol Apr. 2000; 20(8):2902-6 (Abstract only).

Bramson et al., "The efficacy of genetic vaccination is dependent upon the nature of the vector system and antigen", Expert Opin Biol Ther Jan. 2002;2(1):75-85 (Abstract only).

Chang GJ et al., "Flavivirus DNA vaccines: current status and potential", Ann N Y Acad Sci Dec. 2001;951:272-85 (Abstract only).

Cohen et al., "Modulating the immune response to genetic immunization", FASEB J Dec. 1998;12(15):1611-26 (Abstract only).

Cohen EP, "DNA-based vaccines for the treatment of cancer—an experimental model", Trends Mol Med Apr. 2001;7(4):175-9 (Abstract only).

Edgeworth et al., "Vaccine development against HIV-1: current perspectives and future directions", Immunol Res 2002;25(1):53-74 (Abstract only).

Feltquate DM, "DNA vaccines: vector design, delivery, and antigen presentation", J Cell Biochem Suppl 1998;30-31:304-11 (Abstract only).

Hassan et al., "Antitumor Activity of SS(dsFv)PE38 and SS1(dsFv)PE38, Recombinant Antimesothelin Immunotoxins against Human Gynecologic Cancers Grown in Organotypic Culture in Vitro", Clin Cancer Res Nov. 2002;8(11):3520-3526 (Abstract only), 2000.

Hassan et al., "Anti-tumor activity of K1-LysPE38QQR, an immunotoxin targeting mesothelin, a cell-surface antigen overexpressed in ovarian cancer and malignant mesothelioma", J Immunother 200 Jul.-Aug.;23(4):473-9 (Abstract only).

Haupt et al., "The potential of DNA vaccination against tumor-associated antigens for antitumor therapy", Exp Biol Med (Maywood) Apr. 2002;227(4):227-37 (Abstract only).

Havranek et al., "Advances in prostate cancer Immunotherapy", Surg Oncol Jun. 2002;11(1-2):35-45 (Abstract only).

Hellstrom I., "Nucleic Acid Vaccines for Chemoprevention of Ovarian Cancer", Grant No. 5P50CA083636-040002 (Abstract only), 2000.

Hellstrom I., "Mesothelin Antigens for Diagnosis/Therapy of Ovarian Cancer", Grant No. 5R01CA085780-03 (Abstract only), 2007.

Hippo et al., "Differential gene expression profiles of scirrhous gastric cancer cells with high metastatic potential to peritoneum or lymph nodes", Cancer Res Feb. 1, 2001;61(3):889-95 (Abstract only).

Hough et al., "Large-scale serial analysis of gene expression reveals genes differentially expressed in ovarian cancer", Cancer Res Nov. 15, 2000;60(22):6281-7 (Abstract only).

Kaufman et al., "Immunotherapy for pancreatic cancer: current concepts", Hematol Oncol Clin North Am Feb. 2002;16(1):159-97, viii (Abstract only).

Lundstrom K., "Alphavirus vectors for gene therapy applications" Curr Gene Ther May 2001;1(1):19-29 (Abstract only).

Makitalo et al., "ELISpot and ELISA analysis of spontaneous, mitogen-induced and antigen-specific cytokine production in cynomolgus and rhesus macaques", J Immunol Methods Dec. 1, 2002;270(1):85-97 (Abstract only).

Mashishi et al., "The ELISPOT assay: an easily transferable method for measuring cellular responses and identifying T cell epitopes", Clin Chem Lab Med Sep. 2002;40(9):903-10 (Abstract only).

Mitchell MS., "Cancer vaccines, a critical review—Part I", Curr Opin Investig Drugs Jan. 2002;3(1):140-9 (Abstract only).

Monath TP., "Japanese encephalitis vaccines: current vaccines and future prospects", Curr Top Microbiol Immunol 2002;267:105-38 (Abstract only).

Monzavi-Karbassi et al., "Current concepts in cancer vaccine strategies", Biotechniques Jan. 2001;30(1):170-2, 174, 176 (Abstract only).

* cited by examiner

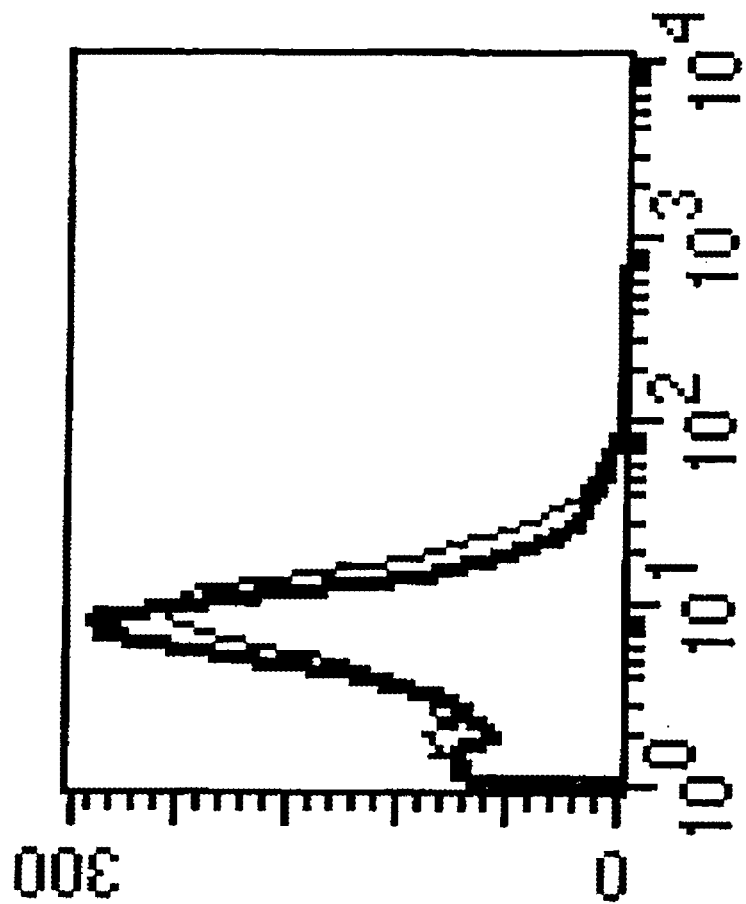

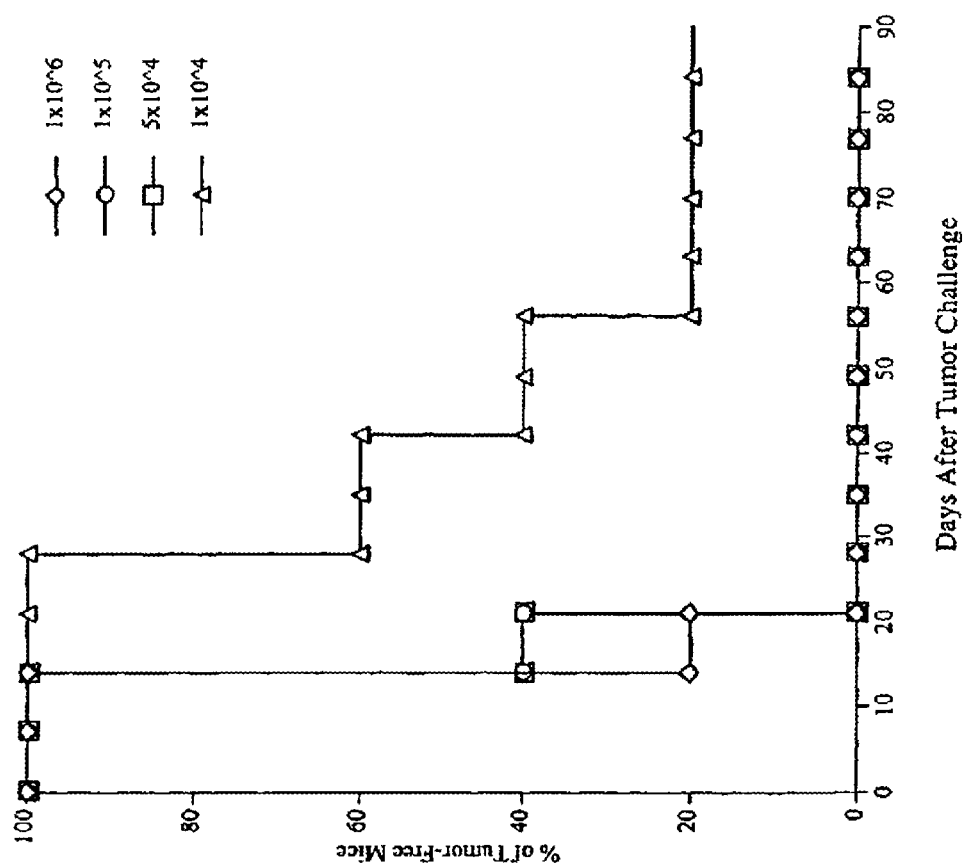

SEQUENCE LISTING

```
<160> NUMBER OF SEQ ID NOS: 22

<210> SEQ ID NO 1
<211> LENGTH: 9
<212> TYPE: PRT
<213> ORGANISM: Homo sapiens

<400> SEQUENCE: 1

Ser Leu Leu Phe Leu Leu Phe Ser Leu
 1               5

<210> SEQ ID NO 2
<211> LENGTH: 9
<212> TYPE: PRT
<213> ORGANISM: Homo sapiens
```

-continued

```
<400> SEQUENCE: 2

Val Leu Pro Leu Thr Val Ala Glu Val
1               5

<210> SEQ ID NO 3
<211> LENGTH: 9
<212> TYPE: PRT
<213> ORGANISM: Homo sapiens

<400> SEQUENCE: 3

Glu Leu Ala Val Ala Leu Ala Gln Lys
1               5

<210> SEQ ID NO 4
<211> LENGTH: 9
<212> TYPE: PRT
<213> ORGANISM: Homo sapiens

<400> SEQUENCE: 4

Ala Leu Gln Gly Gly Gly Pro Pro Tyr
1               5

<210> SEQ ID NO 5
<211> LENGTH: 9
<212> TYPE: PRT
<213> ORGANISM: Homo sapiens

<400> SEQUENCE: 5

Phe Tyr Pro Gly Tyr Leu Cys Ser Leu
1               5

<210> SEQ ID NO 6
<211> LENGTH: 9
<212> TYPE: PRT
<213> ORGANISM: Homo sapiens

<400> SEQUENCE: 6

Leu Tyr Pro Lys Ala Arg Leu Ala Phe
1               5

<210> SEQ ID NO 7
<211> LENGTH: 9
<212> TYPE: PRT
<213> ORGANISM: Homo sapiens

<400> SEQUENCE: 7

Ser Leu Tyr Asn Thr Val Ala Thr Leu
1               5

<210> SEQ ID NO 8
<211> LENGTH: 10
<212> TYPE: PRT
<213> ORGANISM: Homo sapiens

<400> SEQUENCE: 8

Gln Val Pro Leu Arg Pro Met Thr Tyr Lys
1               5                   10

<210> SEQ ID NO 9
<211> LENGTH: 9
<212> TYPE: PRT
<213> ORGANISM: Homo sapiens
```

```
<400> SEQUENCE: 9

Ala Phe Leu Pro Trp His Arg Leu Phe
1               5

<210> SEQ ID NO 10
<211> LENGTH: 9
<212> TYPE: PRT
<213> ORGANISM: Homo sapiens

<400> SEQUENCE: 10

Gly Ile Leu Gly Phe Val Phe Thr Leu
1               5

<210> SEQ ID NO 11
<211> LENGTH: 30
<212> TYPE: DNA
<213> ORGANISM: Mus musculus

<400> SEQUENCE: 11
cccgaattca tggccttgcc aacagctcga                                    30

<210> SEQ ID NO 12
<211> LENGTH: 30
<212> TYPE: DNA
<213> ORGANISM: Mus musculus

<400> SEQUENCE: 12
tatggatccg ctcagcctta aagctgggag                                    30

<210> SEQ ID NO 13
<211> LENGTH: 9
<212> TYPE: PRT
<213> ORGANISM: Homo sapiens

<400> SEQUENCE: 13

Leu Leu Ala Leu Leu Met Ala Gly Leu
1               5

<210> SEQ ID NO 14
<211> LENGTH: 9
<212> TYPE: PRT
<213> ORGANISM: Homo sapiens

<400> SEQUENCE: 14

Ala Leu Gln Pro Gly Thr Ala Leu Leu
1               5

<210> SEQ ID NO 15
<211> LENGTH: 9
<212> TYPE: PRT
<213> ORGANISM: Homo sapiens

<400> SEQUENCE: 15

Ala Leu Leu Pro Ala Leu Gly Leu Leu
1               5

<210> SEQ ID NO 16
<211> LENGTH: 9
<212> TYPE: PRT
<213> ORGANISM: Homo sapiens

<400> SEQUENCE: 16

Ala Leu Gln Pro Ala Ala Ala Ile Leu
1               5
```

```
<210> SEQ ID NO 17
<211> LENGTH: 9
<212> TYPE: PRT
<213> ORGANISM: Homo sapiens

<400> SEQUENCE: 17

Leu Leu Pro Ala Leu Gly Leu Leu Leu
1               5

<210> SEQ ID NO 18
<211> LENGTH: 9
<212> TYPE: PRT
<213> ORGANISM: Homo sapiens

<400> SEQUENCE: 18

Gln Leu Gly Glu Gln Cys Trp Thr Ala
1               5

<210> SEQ ID NO 19
<211> LENGTH: 9
<212> TYPE: PRT
<213> ORGANISM: Homo sapiens

<400> SEQUENCE: 19

Ala Leu Leu Cys Tyr Ser Cys Lys Ala
1               5

<210> SEQ ID NO 20
<211> LENGTH: 9
<212> TYPE: PRT
<213> ORGANISM: Homo sapiens

<400> SEQUENCE: 20

Asp Tyr Tyr Val Gly Lys Lys Asn Ile
1               5

<210> SEQ ID NO 21
<211> LENGTH: 9
<212> TYPE: PRT
<213> ORGANISM: Homo sapiens

<400> SEQUENCE: 21

Tyr Tyr Val Gly Lys Lys Asn Ile Thr
1               5

<210> SEQ ID NO 22
<211> LENGTH: 9
<212> TYPE: PRT
<213> ORGANISM: Homo sapiens

<400> SEQUENCE: 22

Glu Ile Asp Glu Ser Leu Ile Phe Tyr
1               5
```

MESOTHELIN VACCINES AND MODEL SYSTEMS

This application is a continuation-in-part of U.S. application Ser. No. 10/618,088, which claims the benefit of provisional U.S. Applications Ser. No. 60/395,556, filed Jul. 12, 2002, 60/398,217, filed Jul. 24, 2002, Ser. No. 60/414,931, filed Sep. 30, 2002, Ser. No. 60/475,783 filed Jun. 5, 2003, and Ser. No. 60/918,267 filed Mar. 15, 2007. The contents of each of the aforementioned applications are specifically incorporated herein.

This invention was made using funds from the U.S. government. The terms of grants NCI CA62924, NCI RO1 CA72631, NCI RO1 CA71806, U19 CA72108-02, NCDDG RFA CA-95-020, and NCDGG 1U19 CA113341-01 mandate that the U.S. government retains certain rights in the invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of cancer therapeutics, cancer prognosis, and anti-cancer drug development. In some aspects it relates to mesothelin as a therapeutic target. In another aspect it relates to developing other therapeutic targets.

BACKGROUND OF THE INVENTION

Transformation from a normal to a malignant cell involves complex genetic and epigenetic changes, affecting a large number of genes (1, 2). Many of these altered genes are translated into new, altered, or overexpressed proteins that may represent candidate targets for immune rejection. T cell screening of cDNA libraries isolated from tumor cells, biochemical elution and purification of major histocompatibility complex (MHC) bound antigens, and antibody screening of phage display libraries (SEREX method) have greatly facilitated the identification of tumor antigens, particularly those expressed by malignant melanomas (3-13). As a result, there are a number of antigen-specific vaccine approaches under clinical development for this disease (3-6, 14). Unfortunately, these antigen identification approaches have not been successful for identifying antigens expressed by many other common cancers. The major limitation has been the inability to generate patient-derived T cell lines and clones that can be employed to identify immune relevant tumor targets. Furthermore, T cell responses to specific human tumor antigens have not yet been correlated with clinical responses after immunotherapy.

The recent development of high throughput technologies that can quantify gene expression in human tissues has led to the identification of a large number of genes that are differentially expressed in tumors relative to the normal tissue from which they derive (15-18). These gene expression databases can be used as initial filters upon which to apply a functional immune-based screening strategy (19). A growing number of genes shown to be differentially expressed in pancreatic adenocarcinomas using serial analysis of gene expression (SAGE) have been tabulated and reported (20-22). However, it is unclear which of these differentially expressed genes are immunologically relevant for an anti-tumor response. There is a need in the art for a way of identifying immunologically relevant proteins among the proteins which are differentially expressed in tumor and normal tissues.

BRIEF SUMMARY OF THE INVENTION

In a first embodiment a method is provided for inducing a T-cell response to a tumor that overexpresses mesothelin relative to normal tissue from which the tumor is derived. The tumor can be, for example, an ovarian cancer, a pancreatic cancer, a mesothelioma, or a squamous cell carcinoma. A vaccine comprising a polypeptide comprising an MHC Class I- or Class II-binding epitope of mesothelin is administered to a patient who has said tumor or who has had said tumor removed. The patient can also be one who is at risk of developing such a tumor. The epitope binds to an allelic form of MHC class I or MHC class II which is expressed by the patient. A T-cell response to mesothelin is thereby induced. The vaccine does not comprise whole tumor cells. The polypeptide is optionally mesothelin. The T-cell response may be a $CD4^+$ T-cell response and/or a $CD8^+$ T-cell response.

In a second embodiment a method is provided for inducing a T-cell response to a tumor that overexpresses mesothelin relative to normal tissue from which the tumor is derived. The tumor can be, for example, an ovarian cancer, a pancreatic cancer, a mesothelioma, or a squamous cell carcinoma. A vaccine comprising a polynucleotide encoding a polypeptide comprising an MHC Class I- or MHC Class II-binding epitope of mesothelin is administered to a patient who has said tumor or who has had said tumor removed. The patient can also be one who is at risk of developing such a tumor. The epitope binds to an allelic form of MHC class I or class II which is expressed by the patient. A T-cell response to mesothelin is thereby induced. The vaccine does not comprise whole tumor cells. The polypeptide encoded by the polynucleotide of the vaccine is optionally mesothelin. The T-cell response may be a $CD4^+$ T-cell response and/or a $CD8^+$ T-cell response.

In a third embodiment a method is provided for identifying immunogens useful as candidates for anti-tumor vaccines. A protein is selected which is expressed by a tumor and which is minimally or not expressed by normal tissue from which the tumor is derived. Preferably the protein is expressed by a greater than 10% of tumor isolates tested of a type of tumor. Lymphocytes of humans who have been vaccinated with a vaccine which expresses the protein are tested to determine if the lymphocytes comprise $CD8^+$ T cells or $CD4^+$ T cells which are specific for the protein. The presence of the $CD8^+$ T cells or $CD4^+$ T cells indicates that the protein is a candidate for use as an anti-tumor vaccine.

A fourth embodiment of the invention provides a method of predicting future response to a tumor vaccine in a patient who has received the tumor vaccine. Lymphocytes of the patient are tested to determine if the lymphocytes comprise $CD8^+$ T cells or $CD4^+$ T cells which are specific for an antigen in the vaccine. The presence of said $CD8^+$ T cells or $CD4^+$ T cells predicts a longer survival time than the absence of said $CD8^+$ T cells or $CD4^+$ T cells.

A fifth embodiment of the invention provides a vaccine which induces a $CD8^+$ T cell or $CD4^+$ T cell response. The vaccine comprises a polypeptide comprising an MHC Class I- or MHC Class II-binding epitope of mesothelin. The epitope binds to an allelic form of MHC class I or class II which is expressed by the patient. A T-cell response to mesothelin is thereby induced. The vaccine does not comprise whole tumor cells. The vaccine further comprises a carrier for stimulating a T cell immune response. The polypeptide is optionally mesothelin.

Another embodiment of the invention provides another vaccine which induces a CD8+ T cell or CD4+ T cell response. The vaccine comprises a polynucleotide encoding a polypeptide comprising an MHC Class I- or MHC Class II-binding epitope of mesothelin. The epitope binds to an allelic form of MHC class I or class II which is expressed by the patient. A CD8+ T cell or CD4+ T cell response to mesothelin is thereby induced. The vaccine does not comprise whole tumor cells. The vaccine further comprises a carrier for stimulating a T cell immune response. The polypeptide encoded by the polynucleotide of the vaccine is optionally mesothelin.

Another embodiment of the invention provides an isolated polypeptide of 9 to 25 amino acid residues. The polypeptide comprises an epitope selected from the group consisting of SLLFLLFSL (SEQ ID NO: 1); VLPLTVAEV (SEQ ID NO: 2); ELAVALAQK (SEQ ID NO: 3); ALQGGGPPY (SEQ ID NO: 4); FYPGYLCSL (SEQ ID NO: 5); and LYPKARLAF (SEQ ID NO:6).

Yet another embodiment of the invention provides an antibody that binds to an epitope selected from the group consisting of SLLFLLFSL (SEQ ID NO: 1); VLPLTVAEV (SEQ ID NO: 2); ELAVALAQK (SEQ ID NO: 3); ALQGGGPPY (SEQ ID NO: 4); FYPGYLCSL (SEQ ID NO:5); and LYPKARLAF (SEQ ID NO:6).

Yet another embodiment of the invention provides a CD8+ T cell or CD4+ T cell line that binds to MHC class I-peptide complexes, wherein the peptide comprises an epitope selected from the group consisting of SLLFLLFSL (SEQ ID NO: 1); VLPLTVAEV (SEQ ID NO: 2); ELAVALAQK (SEQ ID NO: 3); ALQGGGPPY (SEQ ID NO: 4); FYPGYLCSL (SEQ ID NO:5); and LYPKARLAF (SEQ ID NO:6).

A tenth embodiment of the invention provides a method for predicting future response to a tumor vaccine in a patient who has received the vaccine. The tumor vaccine comprises at least one T-cell epitope of mesothelin. The patient is tested to determine if the patient has a delayed type hypersensitivity (DTH) response to mesothelin, wherein the presence of said response predicts a longer survival time than the absence of said response.

An eleventh embodiment of the invention provides a recombinant mouse cell line which comprises peritoneal cells which have been transformed by HPV-16 genes E6 and E7 and an activated oncogene. The cell line is capable of forming ascites and tumors upon intraperitoneal injection into an immunocompetent mouse.

Also provided is a mouse model which comprises a mouse which has been injected with a recombinant mouse cell line. The recombinant mouse cell line comprises peritoneal cells transfected by HPV-16 genes E6 and E7 and an activated oncogene. The former genes immortalize and the latter gene transforms. The cell line is capable of forming ascites and tumors upon intraperitoneal injection into an immunocompetent mouse.

Another aspect of the invention is a method of testing a substance to determine if it is a potential drug for treating a cancer. The cancer may be, for example, an ovarian cancer, a pancreatic cancer, a mesothelioma, or a squamous cell carcinoma. A test substance is contacted with a mouse model. The mouse model comprises a mouse that has been injected with a recombinant mouse cell line. The injection can be accomplished before or after the test substance is contacted with the mouse. The recombinant mouse cell line comprises peritoneal cells which have been transfected by HPV-16 genes E6 and E7 and an activated oncogene. The cell line is capable of forming ascites and tumors upon intraperitoneal injection into an immunocompetent mouse. One determines whether the test substance causes delay of tumor formation or regression of a tumor in the mouse model, diminution of ascites volume in the mouse model, or longer survival time in the mouse model. Any of these effects indicates that the test substance is a potential drug for treating cancer.

In yet another aspect of the invention a method is provided for treating a mammal having a tumor which overexpresses mesothelin relative to normal tissue from which it is derived. A composition comprising a polynucleotide encoding mesothelin is administered to a mammal who has such a tumor or who has had such a tumor removed. The composition does not comprise whole tumor cells. In addition, antibodies which specifically bind to mesothelin are administered to the mammal.

BRIEF DESCRIPTION OF THE DRAWINGS

FIG. 1A. T2 cells expressing HLA-A2 and pulsed with either: no peptide (black line), a Mesothelin A1309-318 binding peptide (green line), Mesothelin A220-29 (pink line), and Mesothelin A2530-539 (blue line). Peptide pulsed cells were stained with an unlabeled mouse anti-HLA class I molecule monoclonal antibody W6/32 and a goat-anti-mouse FITC-labeled IgG2a secondary antibody. FIG. 1B. T2 cells genetically modified to express A3 and pulsed with either: no peptide (black line), Mesothelin A1309-318 binding peptide (green line), Mesothelin A383-92 (pink line), and Mesothelin A3225-234 (blue line). Peptide pulsed cells were stained with an unlabeled mouse anti-human HLA-A3 specific monoclonal antibody GAPA3 and a FITC-labeled IgG2a secondary antibody. FIG. 1C. T2 cells genetically modified to express A24 and pulsed with either: no peptide (black line), Mesothelin A1309-318 peptide (green line), Mesothelin A24435-444 (pink line), and Mesothelin A24475-484 (blue line). Peptide pulsed cells were stained with an unlabeled pan-HLA antibody W6/32 and a FITC-labeled IgG2a secondary antibody. FIG. 1D. T2 cells expressing HLA-A2 and pulsed with either: Mesothelin A1309-318 binding peptide (green line), PSCA A25-13 (pink line), PSCA A214-22 (blue line), PSCA A2108-116 (orange line) and PSCA A243-51 (red line). Peptide pulsed cells were stained with an unlabeled mouse anti-HLA class I molecule monoclonal antibody W6/32 and a goat-anti-mouse FITC-labeled IgG2a secondary antibody. FIG. 1E. T2 cells genetically modified to express A3 and pulsed with either: Mesothelin A1309-318 binding peptide (green line), PSCA A399-107 (pink line), A35-13 (blue line), A314-22 (orange line), A3109-117 (purple line), A343-51 (red line), and PSCA A320-28 (yellow line). Peptide pulsed cells were stained with an unlabeled mouse anti-human HLA-A3 specific monoclonal antibody GAPA3 and a FITC-labeled IgG2a secondary antibody. FIG. 1F. T2 cells genetically modified to express A24 and pulsed with either: Mesothelin A1309-318 peptide (green line), PSCA A2476-84 (pink line), PSCA A24108-116 (blue line), PSCA A2499-107 (orange line), PSCA A24109-117 (purple line), and PSCA A2477-85 (red line). Peptide pulsed cells were stained with an unlabeled pan-HLA antibody W6/32 and a FITC-labeled IgG2a secondary antibody.

FIG. 2A. ELISPOT analysis of PBL from two patients who were HLA-A 2 and HLA-A3 positive; FIG. 2B. ELISPOT analysis of PBL from two patients who were HLA-A24 positive. FIG. 2C. ELISPOT analysis was performed on PBL from all 14 patients who were treated on the phase I allogeneic GM-CSF secreting pancreatic tumor vaccine study (28). ELISPOT analysis for IFN-γ-expressing cells was performed using PBMC that were isolated on the day prior to vaccination or 28 days following the first vaccination. Lymphocytes were isolated by ficoll-hypaque separation and stored frozen in liquid nitrogen until the day of assay. CD8+ T cell enrichment was performed prior to analysis. T2-A3 cells were pulsed with the two mesothelin derived epitopes MesoA3(83-92) (open squares), MesoA3(225-234) (closed circle) and HIV-NEFA3 (94-103) (open triangle). T2-A2 cells were pulsed with the two mesothelin derived epitopes MesoA2(20-29) (closed squares), MesoA2(530-539) (open circle), and HIV-GAG(77-85), (closed triangle). T2-A24 cells were pulsed with the two mesothelin derived epitopes MesoA24 (435-444) (open diamond), MesoA24(475-484) (closed diamond), and tyrosinase A24(206-214) (star). All DTH responders are represented by red lines, and DTH non-responders are represented by black lines. For the detection of nonspecific background, the number of IFN-γ spots for CD8+ T cells specific for the irrelevant control peptides were counted. The HLA-A2 binding HIV-GAG protein derived epitope (SLYNTVATL; SEQ ID NO:7), the HLA-A3 binding HIV-NEF protein derived epitope (QVPLRPMTYK; SEQ ID NO: 8), and the HLA-A24 binding tyrosinase protein derived epitope (AFLPWHRLF; SEQ ID NO: 9) were used as negative control peptides in these assays. Data represents the average of each condition assayed in triplicate and standard deviations were less than 5%. Plotted are the # of human interferon gamma (hIFNg) spots per 105 CD8+ T cells. Analysis of each patient's PBL was performed at least twice.

FIG. 4A. ELISPOT analysis of PBL from two patients who were HLA-A3 positive; FIG. 4B. ELISPOT analysis of PBL from two patients who were HLA-A 2 and HLA-A3 positive; FIG. 4C. ELISPOT analysis of PBL from two patients who were HLA-A24 positive. FIG. 4D. ELISPOT analysis of PBL from eight patients who were non-responders. ELISPOT analysis for IFN-γ-expressing cells was performed using PBMC that were isolated on the day prior to vaccination or 28 days following each of the vaccination. Lymphocytes were isolated by ficoll-hypaque separation and stored frozen in liquid nitrogen until the day of assay. CD8+ T cell enrichment was performed prior to analysis. T2-A3 cells were pulsed with the six PSCA derived epitopes: PSCAA3(7-15) (closed squares), PSCAA3 (52-60) (closed diamond), PSCAA3(109-117) (SEQ ID NO: 17) (closed triangle), PSCAA3(43-51) (SEQ ID NO: 18) (open square), PSCAA3(20-28) (SEQ ID NO: 19) (open diamond), and PSCAA3(99-107) (SEQ ID NO: 16) (open triangle). Negative HIV-NEFA3 (94-103) values were subtracted out. T2-A2 cells were pulsed with the three PSCA derived epitopes: PSCAA2(5-13) (SEQ ID NO: 13) (closed squares), PSCAA2(14-22) (SEQ ID NO: 14) (closed diamonds), PSCAA2(108-116) (SEQ ID NO: 15) (closed triangles). Negative HIV-GAG(77-85) values were subtracted out. T2-A24 cells were pulsed with the five PSCA derived epitopes: PSCAA24(76-84) (SEQ ID NO: 20) (closed diamond), PSCAA24(77-85) (SEQ ID NO: 21) (star), PSCAA24(109-117) (SEQ ID NO:17) (closed triangles), PSCAA24(108-116) (SEQ ID NO: 15) (closed circle), and PSCAA24(99-107) (SEQ ID NO: 16) (open triangle). Negative Tyrosinase A24(206-214) (SEQ ID NO:9) values were subtracted. All DTH responders are represented by red lines, and DTH non-responders are represented by black lines. For the detection of nonspecific background, the number of IFN-γ spots for CD8+ T cells specific for the irrelevant control peptides were counted. The HLA-A2 binding HIV-GAG protein derived epitope (SLYNTVATL; SEQ ID NO:7), the HLA-A3 binding HIV-NEF protein derived epitope (QVPLRPMTYK; SEQ ID NO: 8), and the HLA-A24 binding tyrosinase protein derived epitope (AFLPWHRLF; SEQ ID NO: 9) were used as negative control peptides in these assays. Data represents the average of each condition assayed in triplicate and standard deviations were less than 5%. The number of human interferon gamma (hIFNg) spots per 105 CD8+ T cells is plotted. Analysis of each patient's PBL was performed at least twice.

FIG. 6A. ELISPOT analysis of PBL from two patients who were HLA-A3 positive; FIG. 6B. ELISPOT analysis of PBL from two patients who were HLA-A 2 and HLA-A3 positive; FIG. 6C. ELISPOT analysis of PBL from two patients who were HLA-A24 positive. ELISPOT analysis for IFN-γ-expressing cells was performed using PBMC that were isolated on the day prior to vaccination or 28 days following each vaccination as described in FIG. 2A to 2D. Each peptide has the same symbol code as described for FIG. 2A to 2D. The DTH responders are represented by the red lines and the DTH non-responders are represented by the black lines. For the detection of non-specific background, the number of IFN-γ spots for CD8+ T cells specific for the irrelevant control peptides were counted. The HLA-A2 binding HIV-GAG protein derived epitope (SLYNTVATL; SEQ ID NO: 7), the HLA-A3 binding HIV-NEF protein derived epitope (QVPLRPMTYK; SEQ ID NO:8), and the HLA-A24 binding melanoma tyrosinase protein derived epitope (AFLPWHRLF; SEQ ID NO: 9) were used as negative control peptides in these assays. Data represent the average of each condition assayed in triplicate and standard deviations were less than 5%. Plotted are the number of human interferon gamma (hIFNg) spots per 105 CD8+ T cells. Analysis of each patient's PBL was performed at least twice.

(FIG. 7B) Hematoxylin and eosin staining of the explanted tumors viewed at 90× magnification. The tumors displayed a papillary configuration, morphologically consistent with tumors derived from the peritoneum or ovaries. Tumors viewed at 400× magnification. The inset displays the features of a WF-3 tumor cell in greater detail.

FIGS. 8A and 8B show MHC class I (FIG. 8A) and MHC class II (FIG. 8B) presentation on the mouse WF-3 tumor cells. WF-3 tumor cells were harvested, trypsinized, washed, and resuspended in FACSCAN buffer. Anti-H2 Kb/H-2D monoclonal antibody or anti-1-Ab monoclonal antibody was added, followed by flow cytometry analysis to detect MHC class I and class II expression on WF-3 tumor cells. (8A) WF-3 tumor cells were positive for MHC class I presentation (thick line) compared to the MHC class I-negative control (thin line). (8B) WF-3 tumor cells were negative for MHC class II presentation. The thin line indicates staining of the MHC class II-negative control.

FIGS. 9A to 9B show the effect of WF-3 tumor dose on ascites formation in two independent trials shown in FIG. 9A and FIG. 3B. WF-3 tumor cells were injected into C57BL/6 mice intraperitoneally at various doses ($1\times10^4$, $5\times10^4$, $1\times10^5$, and $1\times10^6$ cells/mouse). Mice were monitored twice a week for ascites formation and tumor growth. Note: All of the mice injected with $5\times10^4$, $1\times10^5$, and $1\times10^6$ cells intraperitoneally, developed ascites and tumor growth within 30 days. 20% of mice injected with $1\times10^4$ cells were tumor-free without ascites formation after 90 days of tumor injection. The data are from one representative experiment of two performed.

FIG. 10. RT-PCR. RT-PCR was performed using the Superscript One-Step. RT-PCR Kit (Gibco, BRL) and a set of primers: 5'-CCCGAATTCATGGCCTTGCCAA-CAGCTCGA-3' (SEQ ID NO: 11) and 5'-TATGGAATC-CGCTCAGCCTTAAAGCTGGGAG-3' (SEQ ID NO:12). Lane 1, size marker. Lane 2, RNA from W-3 cells and Lane 3, RNA from mesothelin-negative B 16 tumor cells. Specific amplification (indicated by an arrow) was observed in Lane 2 (WF-3 cells) but not in the Lane 3 (B16 cells).

Fig. 14A) Luminescence images of representative Defb29 Vegf-luc/Hmeso challenged mice treated with pcDNA3-Hmeso or pcDNA3 DNA vaccines from day 3 and 60 after tumor challenge. FIG. 14B) Bar graph depicting the luminescence activity (tumor load) of tumor-bearing mice treated with pcDNA3-Hmeso DNA or pcDNA3 DNA from day 3 and 60 after tumor challenge. FIG. 14C) Kaplan Meier survival analysis of the tumor challenged mice treated with pcDNA3-Hmeso or pcDNA3 DNA vaccines. The days indicated follow from day 0 of tumor challenge.

FIG. 15A) Luminescence images of representative mice challenged with Defb29 Vegf-luc/Hmeso cells without depletion or with CD4 depletion, CD8 depletion or NK depletion from days 0, 14 and 30 after tumor challenge. FIG. 15B) Kaplan & Meier survival analysis of the pcDNA3-Hmeso vaccinated mice challenged with Defb29 Vegf-luc/Hmeso tumor cells without depletion or with CD4 depletion, CD8 depletion or NK depletion. The days indicated follow from day 0 of tumor challenge.

FIG. 17A) Representative figures of luminescence images of 96-well plates showing complement-mediated lysis effect on Defb29 Vegf-luc/Hmeso or Defb29 Vegf-luc cells. Note: Significant lysis was demonstrated by decrease of luminescence activity. FIG. 17B) Bar graph depicting the quantification of luminescence in Defb29 Vegf-luc/Hmeso or Defb29 Vegf-luc tumor cells mixed with sera from pcDNA3-Hmeso immunized mice or sera from naïve mice.

FIG. 19A) Representative luminescence images of tumor-bearing athymic nude mice that received sera from naïve mice or sera from pcDNA3-Hmeso immunized mice. FIG. 19B) Bar graph depicting the luminescence activity (tumor load) on day 28 after tumor challenge of tumor-bearing athymic nude mice treated with sera from naïve mice or sera from pcDNA3-Hmeso immunized mice. FIG. 19C) Kaplan & Meier survival analysis of tumor-bearing athymic nude mice that received sera from naïve mice or sera from pcDNA3-Hmeso immunized mice.

FIG. 20A) Bar graph depicting the luminescence activity (tumor load) on day 28 after tumor challenge of tumor-bearing athymic nude mice treated with sera from naïve mice or sera from pcDNA3-Hmeso immunized mice. FIG. 20B) Kaplan & Meier survival analysis of tumor-bearing athymic nude mice that received sera from naïve mice or sera from pcDNA3-Hmeso immunized mice. The days indicated follow from day 0 of tumor challenge.

DETAILED DESCRIPTION OF THE INVENTION

Figure 1:
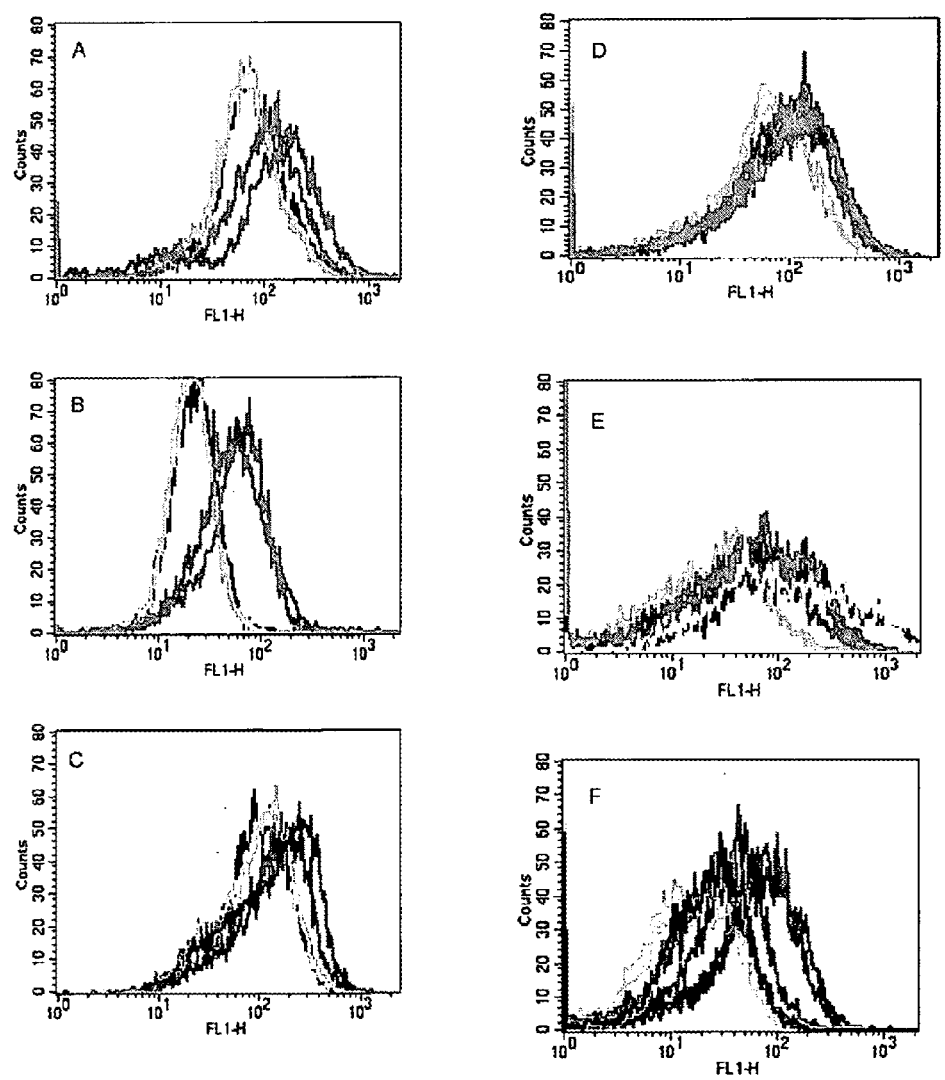
FIGS. 1A to 1F show a T2 binding assay that identifies mesothelin and PSCA protein derived epitopes that bind to HLA-A2, A3, and A24 molecules. T2 cells were pulsed with 100-400 micrograms of peptide overnight at room temperature before analysis by flow cytometry.

The recent development of high-throughput technologies that quantify gene expression has led to the identification of many genes that are differentially expressed in human cancers. However, differential expression does not, on its own, indicate that an antigen is a therapeutic target. Therefore, a functional immunologic screen was applied to a SAGE gene expression database in order to identify immunologically relevant tumor antigens. We previously reported the association of prolonged disease-free survival and in vivo induction of anti-tumor immunity in three of fourteen patients receiving a pancreatic tumor vaccine. Here we identify mesothelin as a tumor antigen recognized by uncultured CD8+ T cells isolated from these vaccinated patients. Moreover, the induction of mesothelin-specific T cells was not found in the eleven other patients who received the same vaccine but relapsed. To validate mesothelin as a tumor antigen, we show that none of the patients respond to another differentially expressed gene product, prostate stem cell antigen. These data identify mesothelin as an in vitro marker of vaccine induced immune responses that correlate with clinical anticancer responses. The inventors also describe a functional genomic approach for identifying and validating other immunologically relevant human tumor antigens.

The vaccines of the present invention can be administered by any means known in the art for inducing a T cell cytolytic response. These means include oral administration, intravenous injection, percutaneous scarification, subcutaneous injection, intramuscular injection, and intranasal administration. The vaccines can be administered intradermally by gene gun. Gold particles coated with DNA may be used in the gene gun. Other inoculation routes as are known in the art can be used.

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types aas macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Further additives, such as preservatives, stabilizers, adjuvants, antibiotics, and other substances can be used as well. Preservatives, such as thimerosal or 2-phenoxy ethanol, can be added to slow or stop the growth of bacteria or fungi resulting from inadvertent contamination, especially as might occur with vaccine vials intended for multiple uses or doses. Stabilizers, such as lactose or monosodium glutamate (MSG), can be added to stabilize the vaccine formulation against a variety of conditions, such as temperature variations or a freeze-drying process.

Viral vectors can be used to administer polynucleotides encoding a polypeptide comprising a mesothelin epitope. Such viral vectors include vaccinia virus and avian viruses, such as Newcastle disease virus. Others may be used as are known in the art.

One particular method for administering polypeptide vaccine is by pulsing the polypeptide onto an APC or dendritic cell in vitro. The polypeptide binds to MHC molecules on the surface of the APC or dendritic cell. Prior treatment of the APCs or dendritic cells with interferon-γ can be used to increase the number of MHC molecules on the APCs or dendritic cells. The pulsed cells can then be administered as a carrier for the polypeptide. Peptide pulsing is taught in Melero et al., *Gene Therapy* 7:1167 (2000).

Naked DNA, such as viral or plasmid DNA molecules, can be injected directly into the host to produce an immune response. Such naked DNA vaccines may be injected intramuscularly into human muscle tissue, or through transdermal or intradermal delivery of the vaccine DNA, typically using biolistic-mediate gene transfer (i.e., gene gun). Recent reviews describing the gene gun and muscle injection delivery strategies for DNA immunization include Tuting, Curr. Opin. Mol. Ther. (1999) 1: 216-25, Robinson, Int. J. Mol. Med. (1999) 4: 549-55, and Mumper and Ledbur, Mol. Biotechnol. (2001) 19: 79-95. Other possible methods for delivering plasmid DNA includes electroporation and iontophoreses.

Another possible gene delivery system comprises ionic complexes formed between DNA and polycationic liposomes (see, e.g., Caplen et al. (1995) Nature Med. 1: 39). Held together by electrostatic interaction, these complexes may dissociate because of the charge screening effect of the polyelectrolytes in the biological fluid. A strongly basic lipid composition can stabilize the complex, but such lipids may be cytotoxic. Other possible methods for delivering DNA includes electroporation and iontophoreses.

The use of intracellular and intercellular targeting strategies in DNA vaccines may further enhance the mesothelin-specific antitumor effect. Previously, intracellular targeting strategies and intercellular spreading strategies have been used to enhance MHC class I or MHC class II presentation of antigen, resulting in potent CD8+ or CD4+ T cell-mediated antitumor immunity, respectively. For example, MHC class I presentation of a model antigen, HPV-16 E7, was enhanced using linkage of *Mycobacterium tuberculosis* heat shock protein 70 (HSP70) (Chen, et al., (2000), Cancer Research, 60: 1035-1042), calreticulin (Cheng, et al., (2001) J Clin Invest, 108:669-678) or the translocation domain (domain II) of Pseudomonas aeruginosa exotoxin A (ETA(dII)) (Hung, et al., (2001) Cancer Research, 61: 3698-3703) to E7 in the context of a DNA vaccine. To enhance MHC class II antigen processing, the sorting signals of the lysosome associated membrane protein (LAMP-1) have been linked to the E7 antigen, creating the Sig/E7/LAMP-1 chimera (Ji, et al, (1999), Human Gene Therapy, 10: 2727-2740). To enhance further the potency of naked DNA vaccines, an intercellular strategy that facilitates the spread of antigen between cells can be used. This improves the potency of DNA vaccines as has been shown using herpes simplex virus (HSV-1) VP22, an HSV-1 tegument protein that has demonstrated the remarkable property of intercellular transport and is capable of distributing protein to many surrounding cells (Elliot, et al., (1997) Cell, 88: 223-233). Such enhanced intercellular spreading of linked protein, results in enhancement of antigen-specific CD8+ T cell-mediated immune responses and antitumor effect. Any such methods can be used to enhance DNA vaccine potency against mesothelin-expressing tumors.

Mesothelin is known to be expressed in ovarian cancer, pancreatic cancer, mesothelioma, and squamous cell carcinomas carcinomas of the esophagus, lung, and cervix. Thus the vaccines of the invention are useful for treating at least these types of tumors. Other tumors which express mesothelin can also be treated similarly.

In one embodiment, the vaccines of the present invention comprise a polypeptide comprising at least one MHC Class I-binding epitope of mesothelin or at least one MHC Class II-binding epitope of mesothelin. Alternatively, the vaccines of the present invention optionally comprise a polynucleotide encoding a polypeptide comprising at least one MHC Class I-binding epitope of mesothelin or at least one MHC Class II-binding epitope of mesothelin. Optionally, the polypeptides of the vaccines (or the p olypeptides encoded by the polynucleotides of the vaccines) comprise a plurality of MHC Class I-binding epitopes of mesothelin and/or MHC Class II-binding epitopes of mesothelin. The multiple epitopes of the polypeptides may bind the same or different MHC allelic molecules. In one embodiment, the epitopes of the polypeptide bind a diverse variety of MHC allelic molecules.

While MHC Class I-binding epitopes are effective in the practice of the present invention, MHC Class II-binding epitopes can also be used. The former are useful for activating $CD8^+$ T cells and the latter for activating $CD4^+$ T cells. Publicly available algorithms can be used to select epitopes that bind to MHC class I and/or class II molecules. For example, the predictive algorithm "BIMAS" ranks potential HLA binding epitopes according to the predictive half-time disassociation of peptide/HLA complexes (23). The "SYFPEITHI" algorithm ranks peptides according to a score that accounts for the presence of primary and secondary HLA-binding anchor residues (25). Both computerized algorithms score candidate epitopes based on amino acid sequences within a given protein that have similar binding motifs to previously published HLA binding epitopes. Other algorithms can also be used to identify candidates for further biological testing.

Polypeptides for immunization to raise a cytolytic T cell response are optionally from 8 to 25 amino acid residues in length. Although nonamers are specifically disclosed herein, any 8 contiguous amino acids of the nonamers can be used as well. The polypeptides can be fused to other such epitopic polypeptides, or they can be fused to carriers, such as B-7, interleukin-2, or interferon-γ. The fusion polypeptide can be made by recombinant production or by chemical linkage, e.g., using heterobifunctional linking reagents. Mixtures of polypeptides can be used. These can be mixtures of epitopes for a single allelic type of an MHC molecule, or mixtures of epitopes for a variety of allelic types. The polypeptides can also contain a repeated series of an epitope sequence or different epitope sequences in a series.

The effectiveness of an MHC Class I-binding epitope of mesothelin or an MHC Class II-binding epitope of mesothelin as an immunogen in a vaccine can be evaluated by assessing whether a peptide comprising the epitope is capable of activating T-lymphocytes from an individual having a successful immunological response to a tumor that overexpresses mesothelin (relative to normal tissue from which the tumor is derived), when the peptide is bound to an MHC molecule on an antigen-presenting cell and contacted with the T-lymphocytes under suitable conditions and for a time sufficient to permit activation of T-lymphocytes. A specific example of such an assessment is illustrated in Examples 1-4, below.

Multiple groups have cloned cDNAs encoding mesothelin, and the sequences of the cDNA clones, as well as the sequence of the encoded mesothelin polypeptides, have been reported in U.S. Pat. No. 6,153,430, Chang and Pastan, *Proc. Natl. Acad. Sci. USA,* 93:136-140 (1996), Kojima et al., *J. Biol. Chem.,* 270:21984-21990 (1995), and U.S. Pat. No. 5,723,318. These references, including the sequences of the mesothelin-encoding nucleic acids, corresponding mesothelin polypeptides, and fragments described therein, are incorporated by reference herein in their entirety. Mesothelin cDNA encodes a protein with a molecular weight of approximately 69 kD, i.e., the primary translation product. The 69 kD form of mesothelin is proteolytically processed to form a 40 kD mature mesothelin protein that is membrane-bound (Chang and Pastan (1996)). The term "mesothelin" as used herein encompasses all naturally occurring variants of the mesothelin, regardless of the cell or tissue in which the protein is expressed. In one embodiment, the mesothelin protein comprises one or more of the following amino acid sequences: SLLFLLFSL (SEQ ID NO:1); VLPLTVAEV (SEQ ID NO:2); ELAVALAQK (SEQ ID NO:3); ALQGGGPPY (SEQ ID NO:4); FYPGYLCSL (SEQ ID NO:5); and LYPKARLAF (SEQ ID NO:6). For instance, the mesothelin protein optionally comprises one, two, three, four, or five of these epitopes. In another embodiment, the mesothelin protein comprises each of the following amino acid sequences: SLLFLLFSL (SEQ ID NO:1); VLPLTVAEV (SEQ ID NO:2); ELAVALAQK (SEQ ID NO:3); ALQGGGPPY (SEQ ID NO:4); FYPGYLCSL (SEQ ID NO:5); and LYPKARLAF (SEQ ID NO:6).

The vaccines of the invention optionally comprise mesothelin or a polynucleotide encoding mesothelin. For instance, the vaccine may comprise or encode the mature form of mesothelin, the primary translation product, or the full-length translation product of the mesothelin gene. In one embodiment, the vaccine comprises the cDNA of mesothelin. In addition to the use of naturally occurring forms of mesothelin (or polynucleotides encoding those forms), polypeptides comprising fragments of mesothelin, or polynucleotides encoding fragments of mesothelin may be used in the vaccines. The polypeptides in the vaccines or encoded by polynucleotides of the vaccines are optionally at least about 95%, at least about 90%, at least about 85%, at least about 80%, at least about 75%, at least about 70%, at least about 65%, at least about 60%, at least about 55%, or at least about 50% identical to mesothelin.

In an alternative embodiment of the invention, the polypeptide of the vaccine or the polypeptide encoded by the polynucleotide of the vaccine is not a naturally-occurring mesothelin protein, such as the mature mesothelin protein, the primary translation product of mesothelin, or the mature megakaryocyte potentiating factor.

In one embodiment, the MHC Class I-binding epitope of mesothelin comprises less than 15 amino acids, less than 14 amino acids, less than 13 amino acids, less than 12 amino acids, or less than 11 amino acids in length. In another embodiment, the MHC Class I-binding epitope of mesothelin comprises at least seven or at least eight contiguous amino acids present in a peptide selected from the group consisting of SLLFLLFSL (SEQ ID NO:1), VLPLTVAEV (SEQ ID NO:2), ELAVALAQK (SEQ ID NO:3), ALQGGGPPY (SEQ ID NO:4), FYPGYLCSL (SEQ ID NO:5), and LYPKARLAF (SEQ ID NO:6). The MHC Class I-binding epitope of mesothelin is at least 7 amino acids in length, at least 8 amino acids in length, or at least 9 amino acids in length.

In addition, the MHC Class I-binding epitopes of mesothelin and the MHC Class II binding epitopes of mesothelin used in vaccines of the present invention need not necessarily be identical in sequence to the naturally occurring epitope sequences within mesothelin. The naturally occurring epitope sequences are not necessarily optimal peptides for stimulating a CTL response. See, for example, (Parkhurst, M. R. et al., *J. Immunol.,* 157:2539-2548, (1996); Rosenberg, S. A. et al., *Nat. Med.,* 4:321-327, (1998)). Thus, there can be utility in modifying an epitope, such that it more readily induces a CTL response. Generally, epitopes may be modified at two types of positions. The epitopes may be modified at amino acid residues that are predicted to interact with the MHC molecule, in which case the goal is to create a peptide sequence that has a higher affinity for the MHC molecule than does the parent epitope. The epitopes can also be modified at amino acid residues that are predicted to interact with the T cell receptor on the CTL, in which case the goal is to create an epitope that has a higher affinity for the T cell receptor than does the parent epitope. Both of these types of modifications can result in a variant epitope that is related to a parent eptiope, but which is better able to induce a CTL response than is the parent epitope.

Thus, the MHC Class I-binding epitopes of mesothelin identified in the Examples below (SEQ ID NO:1-6), or identified by application of the methods of the invention, and the MHC Class II-binding epitopes of mesothelin identified by application of the methods of the invention can be modified by the substitution of one or more residues at different, possibly selective, sites within the epitope sequence. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (H is, Arg, Lys); Group 4—large, aliphatic, nonpolar residues (Met, Leu, Ile, Val, Cys); and Group 4—large, aromatic residues (Phe, Tyr, Trp). An acidic amino acid might also be substituted by a different acidic amino acid or a basic (i.e., alkaline) amino acid by a different basic amino acid. Less conservative substitutions might involve the replacement of one amino acid by another that has similar characteristics but is somewhat different in size, such as replacement of an alanine by an isoleucine residue.

Plasmids and viral vectors, for example, can be used to express a tumor antigen protein in a host cell. The host cell may be any prokaryotic or eukaryotic cell. Thus, for example, a nucleotide sequence derived from the cloning of mesothelin proteins, encoding all or a selected portion of the full-length protein, can be used to produce a recombinant form of a mesothelin polypeptide via microbial or eukaryotic cellular processes. The coding sequence can be ligated into a vector and the loaded vector can be used to transform or transfect hosts, either eukaryotic (e.g., yeast, avian, insect or mammalian) or prokaryotic (bacterial) cells. Such techniques involve standard procedures which are well known in the art.

Typically, expression vectors used for expressing a polypeptide, in vivo or in vitro contain a nucleic acid encoding an antigen polypeptide, operably linked to at least one transcriptional regulatory sequence. Regulatory sequences are art-recognized and can be selected to direct expression of the subject proteins in the desired fashion (time and place). Transcriptional regulatory sequences are described, for example, in Goeddel, Gene Expression Technology: Methods in Enzymology 185, Academic Press, San Diego, Calif. (1990).

Suitable vectors for the expression of a polypeptide comprising HLA-binding epitopes include plasmids of the types: pBR322-derived plasmids, pEMBL-derived plasmids, pEX-derived plasmids, pBTac-derived plasmids and pUC-derived plasmids for expression in prokaryotic cells, such as *E. coli*. Mammalian expression vectors may contain both prokaryotic and eukaryotic sequences in order to facilitate the propagation of the vector in bacteria, and one or more eukaryotic transcription units that can be expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. Vaccinia and avian virus vectors can also be used. The methods which may be employed in the preparation of vectors and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

Other types of expression cassettes can also be used. For instance, the references described below in regard to viral, bacterial, and yeast vectors illustrate additional expression vectors which may be used in the present invention.

In another embodiment of the invention, a polypeptide described herein, or a polynucleotide encoding the polypeptide, is delivered to a host organism in an immunogenic composition comprising yeast. The use of live yeast DNA vaccine vectors for antigen delivery has been reviewed recently and reported to be efficacious in a mouse model using whole recombinant *Saccharomyces cerevisiae* yeast expressing tumor or HIV-1 antigens (see Stubbs et al. (2001) Nature Medicine 7: 625-29).

The use of live yeast vaccine vectors is known in the art. Furthermore, U.S. Pat. No. 5,830,463, the contents of which are incorporated herein by reference, describes particularly useful vectors and systems for use in the instant invention. The use of yeast delivery systems may be particularly effective for use in the tumor/cancer vaccine methods and formulations of the invention as yeast appears to trigger cell-mediated immunity without the need for an additional adjuvant. Particularly preferred yeast vaccine delivery systems are non-pathogenic yeast carrying at least one recombinant expression system capable of modulating an immune response.

Bacteria can also be used as carriers for the epitopes of the present invention. Typically the bacteria used are mutant or recombinant. The bacterium is optionally attenuated. For instance, a number of bacterial species have been developed for use as vaccines and can be used in the present invention, including, but not limited to, *Shigella flexneri, E. coli, Listeria monocytogenes, Yersinia enterocolitica, Salmonella typhimurium, Salmonella typhi* or mycobacterium. The bacterial vector used in the immunogenic composition may be a facultative, intracellular bacterial vector. The bacterium may be used to deliver a polypeptide described herein to antigen-presenting cells in the host organism. The use of live bacterial vaccine vectors for antigen delivery has been reviewed recently (Medina and Guzman (2001) Vaccine 19: 1573-1580; Weiss and Krusch, (2001) Biol. Chem. 382: 533-41; and Darji et al. (2000) FEMS Immunol and Medical Microbiology 27: 341-9). Furthermore, U.S. Pat. Nos. 6,261,568 and 6,488,926, the contents of which are incorporated herein by reference, describe systems useful for cancer vaccines.

Bacterially mediated gene transfer is particularly useful in genetic vaccination by intramuscular, intradermal, or oral administration of plasmids; such vaccination leads to antigen expression in the vaccinee. Furthermore, bacteria can provide adjuvant effects and the ability to target inductive sites of the immune system. Furthermore, bacterial vaccine vectors have almost unlimited coding capacity. The use of bacterial carriers is often associated with still other significant benefits, such as the possibility of direct mucosal or oral delivery. Other direct mucosal delivery systems (besides live viral or bacterial vaccine carriers) which can be used include mucosal adjuvants, viral particles, ISCOMs, liposomes, and microparticles.

Both attenuated and commensal microorganisms have been successfully used as carriers for vaccine antigens. Attenuated mucosal pathogens which may be used in the invention include: *L. monocytogenes, Salmonella* spp., *V. cholorae, Shigella* spp., mycobacterium, *Y. enterocolitica*, and *B. anthracis*. Commensal strains which can be used in the invention include: *S. gordonii, Lactobacillus* spp., and *Staphylococcus* spp. The genetic background of the carrier strain used in the formulation, the type of mutation selected to achieve attenuation, and the intrinsic properties of the immunogen can be adjusted to optimize the extent and quality of the immune response elicited. The general factors to be considered to optimize the immune response stimulated by the bacterial carrier include: selection of the carrier; the specific background strain, the attenuating mutation and the level of attenuation; the stabilization of the attenuated phenotype and the establishment of the optimal dosage. Other antigen-related factors to consider include: intrinsic properties of the antigen; the expression system, antigen-display form and stabilization of the recombinant phenotype; co-expression of modulating molecules and vaccination schedules.

*Salmonella typhimurium* can be used as a bacterial vector in the immunogenic compositions of the invention. Use of this bacterium as an effective vector for a vaccine has been demonstrated in the art. For instance, the use of *S. typhimurium* as an attenuated vector for oral somatic transgene vaccination has been described (see Darji et al. (1997) Cell 91: 765-775; and Darji et al. (2000) FEMS Immun and Medical Microbiology 27: 341-9). Indeed most knowledge of bacteria-mediated gene transfer has been acquired using attenuated *S. typhimurium* as carrier. Two metabolically attenuated strains that have been used include *S. typhimurium* aroA, which is unable to synthesize aromatic amino acids, and *S. typhimurium* 22-11, which is defective in purine metabolism. Several antigens have been expressed using these carriers: originally, listeriolysin and actA (two virulence factors of *L. monocytogenes*) and beta-galactosidase (β-gal) of *E. coli* were successfully tested. Cytotoxic and helper T cells as well as specific antibodies could be detected against these antigens following oral application of a single dose of the recombinant salmonella. In addition, immunization with *Salmonella* carrying a listeriolysin-encoding expression plasmid elicited a protective response against a lethal challenge with *L. monocytogenes*. Oral transgene vaccination methodology has now been extended to include protective responses in herpes simplex virus 2 and hepatitis B infection models, with cell-mediated immune responses detected at the mucosal level.

In tumor models using/β-gal as a surrogate tumor antigen, partial protective immunity against an aggressive fibrosarcoma was induced by orally administering *Salmonella* carrying a β-gal-encoding plasmid (see Paglia et al. (1998) Blood 92: 3172-76). In similar experiments using a β-gal-expressing transfectant of the murine renal cell carcinoma line RENCA, Zöller and Christ (Woo et al. (2001) Vaccine 19: 2945-2954) demonstrated superior efficacy when the antigen-encoding plasmid was delivered in bacterial carriers as opposed to using naked DNA. Interestingly, *Salmonella* can be used to induce a tumor growth retarding response against the murine melanoma B16; the *Salmonella* carry minigenes encoding epitopes of the autologous tumor antigens gp100 and TRP2 fused to ubiquitin. This suggests that under such circumstances peripheral tolerance towards autologous antigens can be overcome. This was confirmed by the same group (Lode et al. (2000) Med Ped Oncol 35: 641-646 using similar constructs of epitopes of tyrosine hydroxylase as autologous antigen in a murine neuroblastoma system. Furthermore, these findings were recently extended by immunizing mice that were transgenic for human carcinogenic antigen (hCEA) using a plasmid encoding a membrane-bound form of complete hCEA. In this case, a hCEA-expressing colon carcinoma system was tested and protection against a lethal challenge with the tumor could be improved by systemic application of interleukin 2 (IL-2) as adjuvant during the effector phase (see Xiang et al. (2001) Clin Cancer Res 7:856s-864s).

Another bacterial vector which may be used in the immunogenic compositions described herein is *Salmonella typhi*. The *S. typhi* strain commonly used for immunization—Ty21a galE—lacks an essential component for cell-wall synthesis. Recently developed improved strains include those attenuated by a mutation in guaBA, which encodes an essential enzyme of the guanine biosynthesis pathway (Pasetti et al., Infect. Immun. (2002) 70:4009-18; Wang et al., Infect. Immun. (2001) 69:4734-41; Pasetti et al., Clin. Immunol. (1999) 92:76-89). Additional references describing the use of *Salmonella typhi* and/or other *Salmonella* strains as delivery vectors for DNA vaccines include the following: Lundin, Infect. Immun. (2002) 70:5622-7; Devico et al., Vaccine, (2002) 20:1968-74; Weiss et al., Biol. Chem. (2001) 382:533-41; and Bumann et al., FEMS Immunol. Med. Microbiol. (2000) 27:357-64.

The vaccines and immunogenic compositions of the present invention can employ *Shigella flexneri* as a delivery vehicle. *S. flexneri* represents the prototype of a bacterial DNA transfer vehicle as it escapes from the vacuole into the cytosol of the host cell. Several attenuated mutants of *S. flexneri* have been used successfully to transfer DNA to cell lines in vitro. Auxotrophic strains were defective in cell-wall synthesis (Sizemore et al. (1995) Science 270: 299-302 and Courvalin et al. (1995) C R Acad Sci Ser III, 318: 1207-12), synthesis of aromatic amino acids (Powell et al. (1996) Vaccines 96: Molecular Approaches to the Control of Infectious Disease; Cold Spring Harbor Laboratory Press) or synthesis of guanine nucleotides (Anderson et al. (2000) Vaccine 18: 2193-2202).

The vaccines and immunogenic compositions of the present invention can comprise *Listeria monocytogenes* (Portnoy et al, Journal of Cell Biology, 158:409-414 (2002); Glomski et al., Journal of Cell Biology, 156:1029-1038 (2002)). The ability of *L. monocytogenes* to serve as a vaccine vector has been reviewed in Wesikirch, et al., Immunol. Rev. 158:159-169 (1997). Strains of *Listeria monocytogenes* have recently been developed as effective intracellular delivery vehicles of heterologous proteins providing delivery of antigens to the immune system to induce an immune response to clinical conditions that do not permit injection of the disease-causing agent, such as cancer (U.S. Pat. No. 6,051,237; Gunn et al., J. Of Immunology, 167:6471-6479 (2001); Liau, et al., Cancer Research, 62: 2287-2293 (2002); U.S. Pat. No. 6,099, 848; WO 99/25376; and WO 96/14087) and HIV (U.S. Pat. No. 5,830,702). A recombinant *L. monocytogenes* vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

As a facultative intracellular bacterium, *L. monocytogenes* elicits both humoral and cell-mediated immune responses. Following entry of *Listeria* into a cell of the host organism, the *Listeria* produces *Listeria*-specific proteins that enable it to escape from the phagolysosome of the engulfing host cell into the cytosol of that cell. Here, *L. monocytogenes* proliferates, expressing proteins necessary for survival, but also expressing heterologous genes operably linked to *Listeria* promoters. Presentation of peptides of these heterologous proteins on the surface of the engulfing cell by MHC proteins permit the development of a T cell response. Two integration vectors that are useful for introducing heterologous genes into the bacteria for use as vaccines include pL1 and pL2 as described in Lauer et al., Journal of Bacteriology, 184: 4177-4186 (2002).

In addition, attenuated forms of *L. monocytogenes* useful in immunogenic compositions have been produced. The ActA protein of *L. monocytogenes* is sufficient to promote the actin recruitment and polymerization events responsible for intracellular movement. A human safety study has reported that oral administration of an actA/plcB-deleted attenuated form of *Listeria monocytogenes* caused no serious sequelae in adults (Angelakopoulos et al., Infection and Immunity, 70:3592-3601 (2002)). Other types of attenuated forms of *L. monocytogenes* have also been described (see, for example, WO 99/25376 and U.S. Pat. No. 6,099,848, which describe auxotrophic, attenuated strains of *Listeria* that express heterologous antigens).

*Yersinia enterocolitica* is another intracellular bacteria that can optionally be used as a bacterial vector in immunogenic compositions of the present invention. The use of attenuated strains of *Yersini enterocolitica* as vaccine vectors is described in PCT Publication WO 02/077249.

In further embodiments of the invention, the immunogenic compositions of the invention comprise mycobacterium, such as *Bacillus* Calmette-Guerin (BCG). The *Bacillus* of Calmette and Guerin has been used as a vaccine vector in mouse models (Gicquel et al., Dev. Biol. Stand 82:171-8 (1994)). See also, Stover et al., Nature 351: 456-460 (1991).

Alternatively, viral vectors can be used. The viral vector will typically comprise a highly attenuated, non-replicative virus. Viral vectors include, but are not limited to, DNA viral vectors such as those based on adenoviruses, herpes simplex virus, avian viruses, such as Newcastle disease virus, poxviruses such as vaccinia virus, and parvoviruses, including adeno-associated virus; and RNA viral vectors, including, but not limited to, the retroviral vectors. Vaccinia vectors and methods useful in immunization protocols are described in U.S. Pat. No. 4,722,848. Retroviral vectors include murine leukemia virus, and lentiviruses such as human immunodeficiency virus. Naldini et al. (1996) Science 272:263-267. Replication-defective retroviral vectors harboring a polynucleotide of the invention as part of the retroviral genome can be used. Such vectors have been described in detail. (Miller, et al. (1990) Mol. Cell. Biol. 10:4239; Kolberg, R. (1992) J. NIH Res. 4:43; Cornetta, et al. (1991) Hum. Gene Therapy 2:215).

Adenovirus and adeno-associated virus vectors useful in this invention may be produced according to methods already taught in the art. (See, e.g., Karlsson, et al. (1986) EMBO 5:2377; Carter (1992) Current Opinion in Biotechnology 3:533-539; Muzcyzka (1992) Current Top. Microbiol. Immunol. 158:97-129; Gene Targeting: A Practical Approach (1992) ed. A. L. Joyner, Oxford University Press, NY). Several different approaches are feasible.

Alpha virus vectors, such as Venezuelan Equine Encephalitis (VEE) virus, Semliki Forest virus (SFV) and Sindbis virus vectors, can be used for efficient gene delivery. Replication-deficient vectors are available. Such vectors can be administered through any of a variety of means known in the art, such as, for example, intranasally or intratumorally. See Lundstrom, Curr. Gene Ther. 2001 1:19-29.

Additional references describing viral vectors which could be used in the methods of the present invention include the following: Horwitz, M. S., Adenoviridae and Their Replication, in Fields, B., et al. (eds.) Virology, Vol. 2, Raven Press New York, pp. 1679-1721, 1990); Graham, F. et al., pp. 109-128 in Methods in Molecular Biology, Vol. 7: Gene Transfer and Expression Protocols, Murray, E. (ed.), Humana Press, Clifton, N.J. (1991); Miller, et al. (1995) FASEB Journal 9:190-199, Schreier (1994) Pharmaceutica Acta Helvetiae 68:145-159; Schneider and French (1993) Circulation 88:1937-1942; Curiel, et al. (1992) Human Gene Therapy 3:147-154; WO 95/00655; WO 95/16772; WO 95/23867; WO 94/26914; WO 95/02697 (Jan. 26, 1995); and WO 95/25071.

In another form of vaccine, DNA is complexed with liposomes or ligands that often target cell surface receptors. The complex is useful in that it helps protect DNA from degradation and helps target plasmid to specific tissues. The complexes are typically injected intravenously or intramuscularly.

Polynucleotides used as vaccines can be used in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g., with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647.

In addition, complex coacervation is a process of spontaneous phase separation that occurs when two oppositely charged polyelectrolytes are mixed in an aqueous solution. The electrostatic interaction between the two species of macromolecules results in the separation of a coacervate (polymer-rich phase) from the supernatant (polymer-poor phase). This phenomenon can be used to form microspheres and encapsulate a variety of compounds. The encapsulation process can be performed entirely in aqueous solution and at low temperatures, and has a good chance, therefore, of preserving the bioactivity of the encapsulant. In developing an injectable controlled release system, the complex coacervation of gelatin and chondroitin sulfate to encapsulate a number of drugs and proteins has been exploited (see Truong, et al. (1995) Drug Delivery 2: 166) and cytokines have been encapsulated in these microspheres for cancer vaccination (see Golumbek et al. (1993) Cancer Res 53: 5841). Anti-inflammatory drugs have also been incorporated for intra-articular delivery to the joints for treating osteoarthritis (Brown et al. (1994) 331: 290). U.S. Pat. Nos. 6,193,970, 5,861,159 and 5,759,582, describe compositions and methods of use of complex coacervates for use as DNA vaccine delivery systems of the instant invention. In particular, U.S. Pat. No. 6,475,995, the contents of which are incorporated herein by reference, teaches DNA vaccine delivery systems utilizing nanoparticle coacervates of nucleic acids and polycations which serve as effective vaccines when administered orally.

Antibodies can be isolated which are specific for a particular MHC Class I- of Class II binding epitope of mesothelin. These antibodies may be monoclonal or polyclonal. They can be used, inter alia, for isolating and purifying polypeptides for use as vaccines. T-cell lines that bind to an MHC class I or class II-peptide complex comprising a particular MHC Class I- of Class II binding epitope of mesothelin are useful for screening for T cell adjuvants and immune response enhancers. Such cell lines can be isolated from patients who have been immunized with a mesothelin-containing vaccine and who have mounted an effective T cell response to mesothelin.

Antibodies can be used therapeutically as well. The antibodies can be raised against particular epitopes, combinations of epitopes, or whole mesothelin. The antibodies can be administered in the form of an immune serum of a mammal who has been immunized with mesothelin, mesothelin-producing cells, mesothelin-encoding viruses, mesothelin polynucleotide, mesothelin epitope polypeptides, mesothelin epitope polypeptide-producing cells, mesothelin epitope-encoding viruses, mesothelin-epitope encoding polynucleotide, etc. The antibodies can be administered in an antiserum or isolated and/or purified from antiserum. The antibodies can be monoclonal or polyclonal. The antibodies can be from the same species of animal as the recipient or different. The antibodies may be genetically engineered or modified to resemble antibodies of the recipient species, although not actually made in cells of the recipient species. For example, humanized or chimeric antibodies can be used.

Antibodies can be administered as a passive immune therapy, rather than as an immune response-inducing therapy. The antibodies may, however, interact with the recipient's immune system to kill tumor cells, for example, using complement.

Combination of passive and active immune therapies can be utilized to increase the recipient's anti-tumor response and to prolong life. An example of such a combination therapy involves a polynucleotide encoding mesothelin and an antibody specifically binding mesothelin. If epitope-targeted vaccines and antibodies are used they may be directed targeted to the same or different portions of the mesothelin protein.

Vaccines, as the term is used herein, may be administered before or after a tumor is detected. They can be administered when a tumor is surgically removed or before or after such removal. The term vaccine implies that an immune response is induced or enhanced. It does not imply any level of effectiveness or prevention. It does not imply absolute prevention or absolute cure.

To test candidate cancer vaccines in the mouse model, the candidate vaccine containing the desired tumor antigen can be administered to a population of mice either before or after challenge with the tumor cell line of the invention. Thus the mouse model can be used to test for both therapeutic and prophylactic effects. Vaccination with a candidate vaccine can be compared to control populations that are either not vaccinated, vaccinated with vehicle alone, or vaccinated with a vaccine that expresses an irrelevant antigen. If the vaccine is a recombinant microbe, its relative efficacy can be compared to a population of microbes in which the genome has not been modified to express the antigen. The effectiveness of candidate vaccine can be evaluated in terms of effect on tumor or ascites volume or in terms of survival rates. The tumor or ascites volume in mice vaccinated with candidate vaccine may be about 5%, about 10%, about 25%, about 50%, about 75%, about 90% or about 100% less than the tumor volume in mice that are either not vaccinated or are vaccinated with vehicle or a vaccine that expresses an irrelevant antigen. The differential in tumor or ascites volume may be observed at least about 10, at least about 17, or at least about 24 days following the implantation of the tumor cells into the mice. The median survival time in mice vaccinated with a nucleic acid-modified microbe may be, for example, at least about 2, at least about 5, at least about 7, or at least about 10 days longer than in mice that are either not vaccinated or are vaccinated with vehicle or a vaccine that expresses an irrelevant antigen.

The mouse model can be used to test any kind of cancer treatment known in the art. These may be conventional or complementary medicines. These can be immunological agents or cytotoxic agents. For example, the candidate cancer treatment may be radiation therapy, chemotherapy, or surgery. The candidate cancer treatment may be a combination of two or more therapies or prophylaxes, including but not limited to anti-cancer agents, anti-tumor vaccines, radiation therapy, chemotherapies, and surgery.

Any oncogene known in the art can be used to make the peritoneal or mesothelium cell line for making the mouse model. Such oncogenes include without limitation, Ki-ras, Erb-B2, N-ras, N-myc, L-myc, C-myc, ABL1, EGFR, Fos, Jun, c-Ha-ras, and SRC.

The vaccines, polynucleotides, polypeptides, cells, and viruses of the present invention can be administered to either human or other mammals. The other mammals can be domestic animals, such as goats, pigs, cows, horses, and sheep, or can be pets, such as dogs, rabbits, and cats. The other mammals can be experimental subjects, such as mice, rats, rabbits, monkeys, or donkeys.

A reagent used in therapeutic methods of the invention is present in a pharmaceutical composition. Pharmaceutical compositions typically comprise a pharmaceutically acceptable carrier, which meets industry standards for sterility, isotonicity, stability, and non-pyrogenicity and which is nontoxic to the recipient at the dosages and concentrations employed. The particular carrier used depends on the type and concentration of the therapeutic agent in the composition and the intended route of administration. If desired, a stabilizing compound can be included. Formulation of pharmaceutical compositions is well known and is described, for example, in U.S. Pat. Nos. 5,580,561 and 5,891,725.

The determination of a therapeutically effective dose is well within the capability of those skilled in the art. A therapeutically effective dose refers to that amount of active ingredient that increases anti-tumor cytolytic T-cell activity relative to that which occurs in the absence of the therapeutically effective dose.

For any substance, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Effective in vivo dosages of polynucleotides and polypeptides are in the range of about 100 ng to about 200 ng, 500 ng to about 50 mg, about 1 µg to about 2 mg, about 5 µg to about 500 µg, and about 20 µg to about 100 µg.

Desirable immunogens for use as anti-tumor vaccines are those which are highly differentially expressed between tumors and their corresponding normal tissues. Expression differences are preferably at least 2-fold, 3-fold, 4-fold, 5-fold, or even 10 fold. Expression can be measured by any means known in the art, including but not limited to SAGE, microarrays, Northern blots, and Western blots. Interest in such proteins as immunogens is enhanced by determining that humans respond to immunization with the protein (or gene encoding it) by generating CD4 or CD8 T cells which are specifically activated by the protein. Testing for such activation can be done, inter alia, using TAP deficient cell lines such as the human T2 cell line to present potential antigens in an MHC complex. Activation can be measured by any assay known in the art. One such assay is the ELISPOT assay. See references 33-35.

Future responses to tumor vaccines can be predicted based on the response of CD8+ and or CD4+ T cells. If the tumor vaccine comprises mesothelin or at least one T cell epitope of mesothelin, then monitoring of the of CD8+ and or CD4+ response to mesothelin provides useful prognostic information. A robust CD8+ and or CD4+ response indicates that the patient has mounted an effective immunological response and will survive significantly longer than those who have not mounted such a response. The tumor vaccine may comprise whole tumor cells, particularly pancreatic, ovarian or mesothelioma cells. The tumor vaccine may comprise a polyethylene glycol fusion of tumor cells and dendritic cells. The tumor vaccine may comprise apoptotic or necrotic tumor cells which have been incubated with dendritic cells. The tumor vaccine may comprise mRNA or whole RNA which has been incubated with dendritic cells. The T cell responses to mesothelin can be measured by any assay known in the art, including an ELISPOT assay. Alternatively, future response to such a tumor vaccine can be monitored by assaying for a delayed type hypersensitivity response to mesothelin. Such a response has been identified as a positive prognostic indicator.

Test substances which can be tested for use as a potential drug or immune enhancing agent can be any substance known in the art. The substance can be previously known for another purpose, or it can be previously unknown for any purpose. The substance can be a purified compound, such as a single protein, nucleic acid, or small molecule, or it can be a mixture, such as an extract from a natural source. The substance can be a natural product, or it can be a synthetic product. The substance can be specifically and purposefully synthesized for this purpose or it can be a substance in a library of compounds which can be screened.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

To identify genes that can serve as potential immune targets for the majority of pancreatic adenocarcinoma patients, we focused only on those genes that were non-mutated, overexpressed by the majority of pancreatic cancer patients, and overexpressed by the vaccine cell lines. One gene at the top of this list was mesothelin (20, 21). For comparison and validation purposes we also looked at prostate stem cell antigen (PSCA). SAGE data demonstrated PSCA to be expressed by pancreatic tumors at similar levels to that of mesothelin (22).

We used the combination of two public use computer algorithms (23-25) to predict peptide nonamers that bind to three common human leukocyte antigen (HLA)-class I molecules. All 14 patients treated with the allogeneic GM-CSF vaccine express at least one of these HLA-Class I molecules (Table 2). The predictive algorithm "BIMAS", ranks potential HLA binding epitopes according to the predictive half-time disassociation of peptide/HLA complexes (23). The "SYFPEITHI" algorithm ranks peptides according to a score that accounts for the presence of primary and secondary HLA-binding anchor residues (25). Both computerized algorithms score candidate epitopes based on amino acid sequences within a given protein that have similar binding motifs to previously published HLA binding epitopes. We synthesized the top two ranking mesothelin epitopes for HLA-A2, HLA-A3, and HLA-A24 and the top six PSCA epitopes for each MHC molecule favored by both algorithms (Table 1), since at least one of these three HLA class I molecules is expressed by the 14 patients that were treated in our vaccine study (Table 2).

TABLE 1

Mesothelin peptides predicted to bind to HLA A2, A3, and A24.

| HLA-Restriction | Amino Acid Sequence | Amino Acid Position in Protein |
|---|---|---|
| HLA-A2 | SLLFLLFSL (SEQ ID NO: 1) | Mesothelin A2 $_{(20-28)}$ |
| HLA-A2 | VLPLTVAEV (SEQ ID NO: 2) | Mesothelin A2 $_{(530-538)}$ |
| HLA-A2 | LLALLMAGL (SEQ ID NO: 13) | PSCA A2 $_{(5-13)}$ |
| HLA-A2 | ALQPGTALL (SEQ ID NO: 14) | PSCA A2 $_{(14-22)}$ |
| HLA-A2 | ALLPALGLL (SEQ ID NO: 15) | PSCA A2 $_{(108-116)}$ |
| HLA-A3 | ELAVALAQK (SEQ ID NO: 3) | Mesothelin A3 $_{(83-92)}$ |

TABLE 1-continued

Mesothelin peptides predicted to bind to HLA A2, A3, and A24.

| HLA-Restriction | Amino Acid Sequence | Amino Acid Position in Protein |
|---|---|---|
| HLA-A3 | ALQGGGPPY (SEQ ID NO: 4) | Mesothelin A3 $_{(225-234)}$ |
| HLA-A3 | ALQPAAAIL (SEQ ID NO: 16) | PSCA A3 $_{(99-107)}$ |
| HLA-A3 | LLALLMAGL (SEQ ID NO: 13) | PSCA A3 $_{(5-13)}$ |
| HLA-A3 | ALQPGTALL (SEQ ID NO: 14) | PSCA A3 $_{(14-22)}$ |
| HLA-A3 | LLPALGLLL (SEQ ID NO: 17) | PSCA A3 $_{(109-117)}$ |
| HLA-A3 | QLGEQCWTA (SEQ ID NO: 18) | PSCA A3 $_{(43-51)}$ |
| HLA-A3 | ALLCYSCKA (SEQ ID NO: 19) | PSCA A3 $_{(20-28)}$ |
| HLA-A24 | FYPGYLCSL (SEQ ID NO: 5) | Mesothelin A24 $_{(435-444)}$ |
| HLA-A24 | LYPKARLAF (SEQ ID NO: 6) | Mesothelin A24 $_{(475-484)}$ |
| HLA-A24 | DYYVGKKNI (SEQ ID NO: 20) | PSCA A24 $_{(76-84)}$ |
| HLA-A24 | ALLPALGLL (SEQ ID NO: 15) | PSCA A24 $_{(108-116)}$ |
| HLA-A24 | ALQPAAAIL (SEQ ID NO: 16) | PSCA A24 $_{(99-107)}$ |
| HLA-A24 | LLPALGLLL (SEQ ID NO: 17) | PSCA A24 $_{(109-117)}$ |
| HLA-A24 | YYVGKKNIT (SEQ ID NO: 21) | PSCA A24 $_{(77-85)}$ |

The three peptides, HIV-gag A2$_{77-85}$ (SLYNTVATL) (SEQ ID NO: 7) (48), HIV-NEF A3$_{94-103}$ (QVPLRPMTYK) (SEQ ID NO: 8) (49), and tyrosinase A24$_{206-214}$ (AFLPWHRLF) (SEQ ID NO:9) (50), are previously published epitopes that were used as control peptides for HLA-A2, A3, and A24 binding, respectively. The Mesothelin A1$_{309-318}$ binding epitope (EIDESLIFY) (SEQ ID NO: 22) was used as a negative control peptide for all binding studies. The M1 peptide (GILGFVFTL)$_{58-66}$ (SEQ ID NO: 10) (Gotch et al 1988) was used as a positive control for all of the HLA-A2 studies.

TABLE 2

Selected Characteristics of the 14 patients treated with an allogeneic GM-CSF secreting pancreatic tumor vaccine.

| Pt # | Disease Status | | | Dose × $10^7$ Cells | # of total vaccines received | HLA Class I Expression at the A Locus[1] | Post-vaccine increase in DTH to Auto Tumor[2] | Disease-free Survival (months) | Overall Survival (months) |
|---|---|---|---|---|---|---|---|---|---|
| | T (cm) | LN | Margins | | | | | | |
| 1 | 3.0 | 5/17 | − | 1 | 2 | A1, A2 | 0 | 11 | 14 |
| 2 | 2.7 | 3/17 | + | 1 | 1 | A2, A3 | 0 | 6 | 14 |
| 3 | 2.5 | 3/11 | + | 1 | 1 | A1, A3 | 0 | 9 | 18 |
| 4 | 2.5 | 3/14 | − | 5 | 1 | A2, A29 | 0 | 8 | 10 |
| 5 | 2.7 | 2/23 | − | 5 | 4 | A3, A3 | 0 | 15 | 39 |
| 6 | 2.5 | 2/17 | − | 5 | 3 | A2, A24 | 0 | 13 | 27 |
| 7 | 4.0 | 4/13 | + | 10 | 1 | A31, A24 | 0 | 16 | 18 |
| 8 | 2.7 | 5/18 | + | 10 | 2 | A2, A3 | 252 mm | 60+ | 60+ |
| 9 | 1.2 | 2/11 | − | 10 | 1 | A3, A31 | 0 | 8 | 21 |
| 10 | 2.0 | 11/27 | − | 50 | 1 | A3, A30 | 0 | 9 | 17 |
| 11 | 3.5 | 2/32 | + | 50 | 1 | A1, A3 | N/A | 9 | 13 |
| 12 | 2.5 | 2/11 | − | 50 | 1 | A3, A33 | N/A | 11 | 13 |
| 13 | 3.0 | 2/14 | − | 50 | 4 | A3, A23 | 100 mm | 60+ | 60+ |
| 14 | 3.0 | 0/14 | + | 50 | 4 | A1, A24 | 110 mm | 60+ | 60+ |

Abbreviations:
Pt = patient,
# = number,
T = tumor size at surgery,
LN = number of positive lymph nodes/total number of lymph nodes sampled,
HLA = human leukocyte antigen,
DTH = delayed type hypersensitivity testing,
Auto = autologous,
N/A = not assessed due to unavailability of DTH cell reagents,
+ = still alive and disease-free.
[1]HLA typing was performed serologically and confirmed molecularly.
[2]Delayed type hypersensitivity reactions to autologous tumor cells was assessed using unpassaged autologous tumor cells. $10^6$ autologous tumor cells were placed pre-vaccination, and at 28 days post-vaccination. Reported are the post-vaccination change in the product of the perpendicular diameters (measured in mm) of the observed induration at 48 hours after cell placement.

Binding of these epitopes to their respective HLA class I molecule was tested by pulsing TAP deficient T2 cells that expressed the corresponding HLA class I molecule (T2-A2, T2-A3, or T2-A24 cells). As shown in FIG. 1A, pulsing of two mesothelin-derived epitopes predicted to bind to HLA-A2 allows for detection of HLA-A2 on the cell surface of T2-A2 cells by flow cytometry following staining with the HLA class I specific antibody, W6/32. In contrast, unpulsed T2 cells or T2 cells pulsed with an mesothelin epitope predicted to bind to HLA-A1 do not stain with the same antibody. Binding of T2 cells pulsed with two candidate mesothelin derived HLA-A3 and two candidate HLA-A24 epitopes are shown in FIG. 1B and FIG. 1C, respectively. A similar binding experiment was done with the PSCA derived peptides for HLA-A2, HLA-A3, and HLA-A24. (FIG. 1D, FIG. 1E and FIG. 1F).

Materials and Methods: Identification of candidate genes and epitope selection. SAGE was used to identify mesothelin as one of the genes overexpressed in pancreatic cancer cell lines and fresh tissue as previously reported (20, 21). Two computer algorithms that are available to the general public and accessible through the internet were used to predict peptides that bind to HLA A2, A3, and A24 molecules. "BIMAS" was developed by K. C. Parker and collaborators http://bimas.dcrt.nih.gov/ (NIH) that determined the optimal binding for the most common HLA class I molecule types (23). "SYFPEITHI" was developed by Rammensee et al. and ranks the peptides according to a score that takes into account the presence of primary and secondary MHC-binding anchor residues http://www.uni-tuebingen.de/uni/kxi (24).

Materials and Methods: Peptides and T2 cell lines. Peptides were synthesized by Macromolecular Resources (Fort Collins, Colo.) according to published sequences: M1 peptide GILGFVFTL (SEQ ID NO: 10), derived from influenza matrix protein (amino acid positions 58-66) (28), Mesothelin A2 peptides and PSCA A2 peptides listed in table 1 were identified using the available databases, HIV-gag A2 peptide SLYNTVATL (SEQ ID NO: 7) (amino acid positions 75-83) (29) contain an HLA-A2 binding motif. Mesothelin A3 peptides and PSCA A3 peptides and HIV-NEF A3 peptide QVPLRPMTYK (SEQ ID NO: 8) (amino acid positions 94-103) (30) contain an HLA-A3 binding motif. Mesothelin A24 peptides and PSCA A24 peptides and Tyrosinase peptide AFLPWHRLF (SEQ ID NO: 9) (amino acid positions 206-214) (31) contain an HLA-A24 binding motif. Stock solutions (1 mg/ml) of each peptide were prepared in 10% DMSO (JTBaker, Phillippsburg, N.J.) and further diluted in cell culture medium to yield a final peptide concentration of 10 ng/ml for each assay. The control M1 peptide was initially dissolved in 100% DMSO and further diluted in cell culture medium using the same stock and final concentrations. The T2 cells are a human B and T lymphoblast hybrid that only express the HLA-A*0201 allele (26). The human T2 cell line is a TAP deficient cell line that fails to transport newly digested HLA class I binding epitopes from the cytosol into the endoplasmic reticulum where these epitopes would normally bind to nascent HLA molecules and stabilize them for expression on the cell surface (26). The T2-A3 are T2 cells genetically modified to express the HLA-A301 allele and were a gift from Dr. Walter Storkus (University of Pittsburgh) (32). T2-A24 are T2 cells genetically modified to express the HLA-A24 allele. The HLA-A24 gene was a gift from Dr. Paul Robbins (Surgery Branch, National Cancer Institute) (31). T2 cells were grown in suspension culture in RPMI-1640 (Gibco, Grand Island, N.Y.), 10% serum (Hyclone, Logan, Utah) supplemented with 200 µM L-Glutamine (Gibco, Grand Island, N.Y.), 50 units-µg/ml Pen/Strep (Gibco), 1% NEAA (Gibco), and 1% Na-Pyruvate (Gibco).

Materials and Methods: Peptide/MHC binding Assays. T2 cells expressing the HLA molecule of interest were resuspended in AimV serum free media (Gibco) to a concentration of $2.5 \times 10^5$ cells/ml and pulsed with 100-200 micrograms of peptide at room temperature overnight. Pulsing at room temperature allows for optimizing the number of empty HLA molecules available for binding each epitope (30). The cells were washed and resuspended at $1 \times 10^5$ cells/ml. Peptide binding was determined by FACS (Beckon Dickenson, San Jose, Calif.) analysis.

Example 2

Figure 2A:
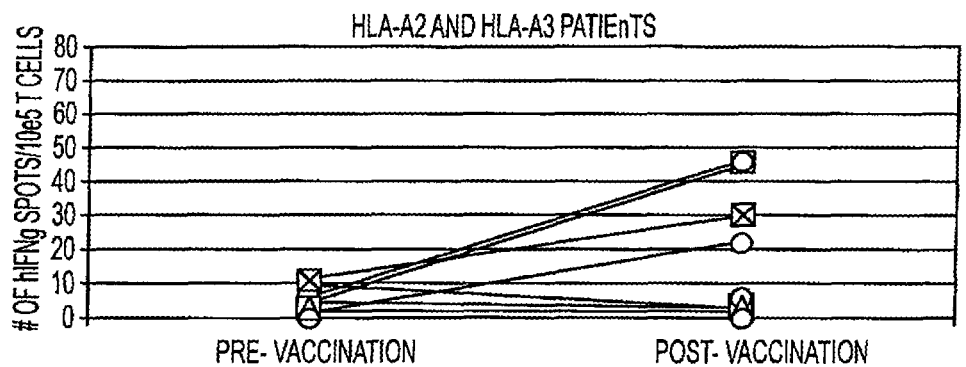
FIGS. 2A to 2C show an ELISPOT analysis of CD8+ T cells from PBMCs which demonstrates post-vaccination induction of mesothelin-specific T cells in three DTH responders but not in 11 non-DTH responders who received an allogeneic GM-CSF-secreting tumor vaccine for pancreatic cancer.

To determine if mesothelin and PSCA are recognized by CD8+ T cells, we screened antigen-pulsed T2 cells with CD8+ T cell enriched PBL from patients that have received an allogeneic GM-CSF secreting pancreatic tumor vaccine. We previously reported the association of in vivo post-vaccination delayed type hypersensitivity (DTH) responses to autologous tumor in three of eight patients receiving the highest two doses of vaccine. These "DTH responders" (each of whom had poor prognostic indicators at the time of primary surgical resection (27) are the only patients who remain clinically free of pancreatic cancer >4 years after diagnosis ((27), Table 2). PBL obtained prior to vaccination and 28 days after the first vaccination were initially analyzed. T2-A3 cells pulsed with the two A3 binding epitopes were incubated overnight with CD8+ T cell enriched lymphocytes isolated from the peripheral blood of patient 10 (non-DTH responder who relapsed 9 months after diagnosis) and 13 (DTH responder who remains disease-free) and analyzed using a gamma interferon (IFN-γ) ELISPOT assay. The ELISPOT assay was chosen because it requires relatively few lymphocytes, is among the most sensitive in vitro assays for quantitating antigen-specific T cells, and correlates number of antigen-specific T cells with function (cytokine expression) (33-35). The number of IFN-γ spots per $1 \times 10^5$ CD8+ positive T cells detected in the peripheral blood of the two patients prior to vaccination and twenty-eight days following the first vaccination in response to the two HLA-A3 binding mesothelin peptides are shown in FIG. 2A.

Figure 2B:
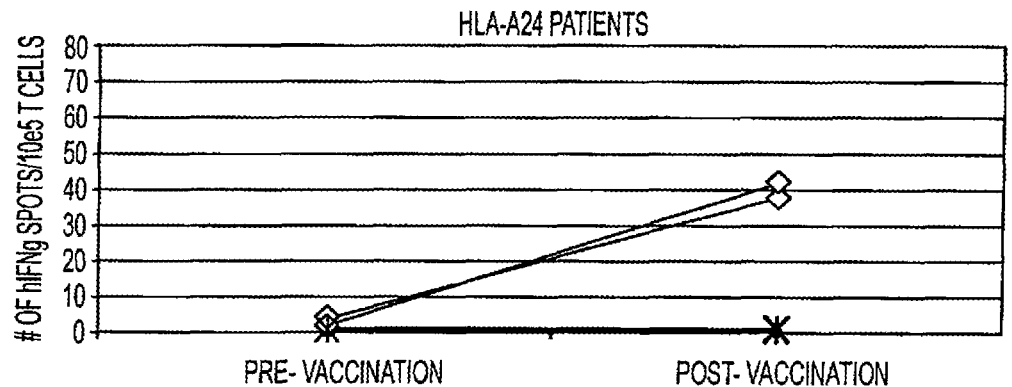
Figure 2C:
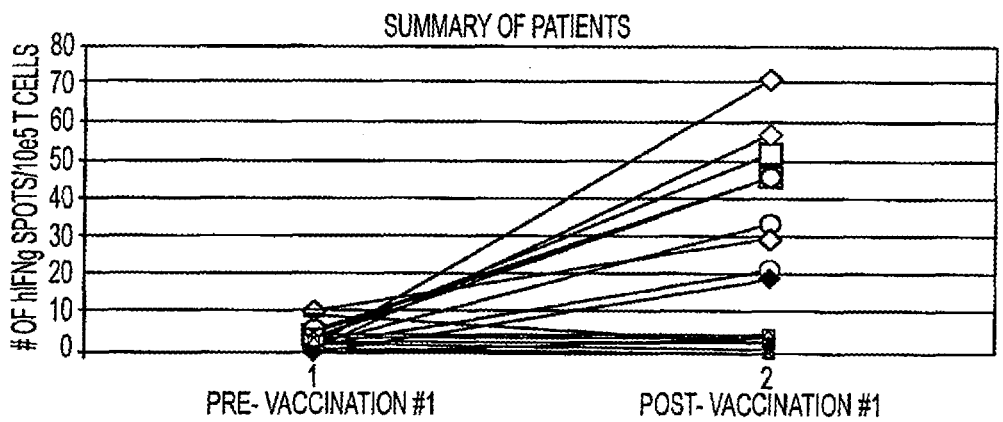

Induction of mesothelin-specific T cells was detected twenty-eight days following vaccination in patient 13 a DTH responder, but not in patient 10, a non-DTH responder. Similarly, post-vaccination induction of mesothelin-specific CD8+ T cells was observed in two other disease-free DTH responders (patient 8 and patient 14), but not for two other non-DTH responders when tested with T2-A2 and T2-A24 cells pulsed with the A2 (FIG. 2B) and A24 (FIG. 2C) binding epitopes, respectively. A summary of the ELISPOT results analyzing all 14 patients treated with the allogeneic vaccine on this study for the induction of mesothelin-specific CD8+ T cells following the first vaccination are shown in FIG. 2D. These data demonstrate that there is a direct correlation between observed post-vaccination in vivo DTH responses to autologous tumor, long term disease-free survival, and post-vaccination induction of mesothelin-specific T cell responses in this clinical trial. Specifically, each of the three DTH responders demonstrated a post-vaccination induction in T cell response to every mesothelin peptide that matched their respective HLA type, whereas only one of eleven DTH non-responders had an increased post-vaccination mesothelin-specific T cell response and only to a single peptide. Thus, the in vitro measurement of mesothelin-specific T cells responses represents a new candidate in vitro immune marker for predicting which patients will respond to this vaccine therapy.

Materials and Methods: Peripheral blood lymphocytes (PBL) and donors. Peripheral blood (100 cc pre-vaccination and 28 days after each vaccination) were obtained from all fourteen patients who received an allogeneic GM-CSF secreting pancreatic tumor vaccine as part of a previously reported phase I vaccine study (27). Informed consent for banking lymphocytes to be used for this antigen identification study was obtained at the time of patient enrollment into the study. Pre and post-vaccine PBL were isolated by density gradient centrifugation using Ficoll-Hypaque (Pharmacia, Uppsala, Sweden). Cells were washed twice with serum free RPMI-1640. PBL were stored frozen at −180° C. in 90% AIM-V media containing 10% DMSO.

Materials and Methods: Enrichment of PBL for CD8+ T cells. CD8+ T cells were isolated from thawed PBL using Magnetic Cell Sorting of Human Leukocytes as per the manufacturers directions(MACS, Miltenyi Biotec, Auburn, Calif.). Cells were fluorescently stained with CD8-PE antibody (Becton Dickenson, San Jose, Calif.) to confirm that the positive population contained CD8+ T cells and analyzed by flow cytometry. This procedure consistently yielded >95% CD8+ T cell purity.

Materials and Methods: ELISPOT assay. Multiscreen ninety-six well filtration plates (Millipore, Bedford, Mass.) were coated overnight at 4° C. with 60 µl/well of 10 µg/ml anti-hIFN-γ mouse monoclonal antibody (Mab) 1-D1K (Mabtech, Nacka, Sweden). Wells were then washed 3 times each with 1×PBS and blocked for 2 hours with T cell media. 1×10$^5$ T2 cells pulsed with peptide (10 ng/ml) in 100 µl of T cell media were incubated overnight with 1×10$^5$ thawed PBL that are purified to select CD8+ T cells in 100 µl T-cell media on the ELISPOT plates in replicates of six. The plates were incubated overnight at 37° C. in 5% CO2. Cells were removed from the ELISPOT plates by washing six times with PBS+ 0.05% Tween 20 (Sigma, St. Louis, Mo.). Wells were incubated for 2 hours at 37° C. in 5% CO2 using 60 µl/well of 2 µg/ml biotinylated Mab anti-hIFNgamma 7-B6-1 (Mabtech, Nacka, Sweden). The avidin peroxidase complex (Vectastain ELITE ABC kit, Vetcor Laboratories, Burlingame, Calif.) was added after washing six times with PBS/Tween 0.05% at 100 µl per well and incubated for one hour at room temperature. AEC-substrate solution (3-amino-9-ethylcarbazole) was added at 100 µl/well and incubated for 4-12 minutes at room temperature. Color development was stopped by washing with tap water. Plates were dried overnight at room temperature and colored spots were counted using an automated image system ELISPOT reader (Axioplan2, Carl Zeiss Microimaging Inc., Thornwood, N.Y.).

Example 3

The above data clearly demonstrate a correlation of in vivo DTH response to autologous tumor and long term disease-free survival with the post-vaccination induction of mesothelin-specific CD8+ T cell responses. It is possible, however, that this correlation represents generalized immune suppression (in the patients who failed to demonstrate post-vaccination DTH responses to their autologous tumor and who had disease progression), rather than a vaccine specific induction of T cell responses to mesothelin in the DTH responder patients who remain disease-free. To demonstrate that the post-vaccination induction of mesothelin-specific CD8+ T cells is tumor antigen-specific, we evaluated each HLA-A2 positive patient for T cell responses to the HLA-A2-binding influenza matrix peptide, M1 (28). We chose the influenza M1 peptide because most patients on the vaccine study had received an influenza vaccine sometime prior to enrollment.

Figure 3:
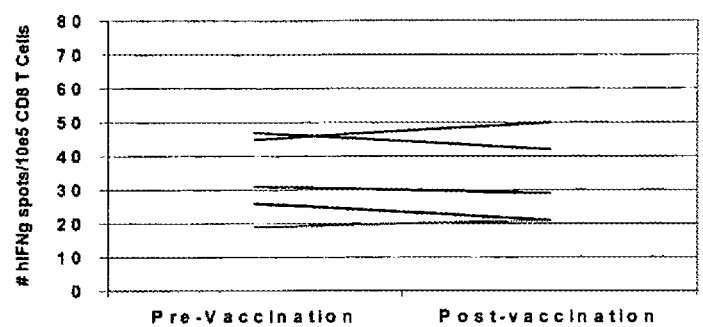
FIG. 3 shows an ELISPOT analysis performed to assess the recognition of the influenza matrix protein HLA-A2 binding epitope M1 (GILGFVFTL; SEQ ID NO: 10) on PBL from all 5 patients on the study who were HLA-A2 positive (4 non-DTH responders and 1 DTH responder). This analysis was performed on the same PBL samples described for FIGS. 2 A to 2D above. The DTH responders are represented by red lines, and the DTH non-responders are represented by black lines. For the detection of nonspecific background, the number of IFN-γ spots for CD8+ T cells specific for the irrelevant control peptides were counted. The HLA-A2 binding HIV-GAG protein derived epitope (SLYNTVATL; SEQ ID NO:7), the HLA-A3 binding HIV-NEF protein derived epitope (QVPLRPMTYK; SEQ ID NO: 8), and the HLA-A24 binding melanoma tyrosinase protein derived epitope (AFLPWHRLF; SEQ ID NO: 9) were used as negative control peptides in these assays. Data represents the average of each condition assayed in triplicate and standard deviations were less than 5%. Plotted are the # of human interferon gamma (hIFNg) spots per 105 CD8+ T cells. Analysis of each patient's PBL was performed at least twice and all ELISPOT assays were performed in a blinded fashion.

As shown in FIG. 3, all HLA-A2 positive patients demonstrated similar pre- and post-vaccination T cell responses to the M1 peptide. Pre-vaccination responses ranged from 19 to 50 IFN-γ spots per 10$^5$ total CD8+ T cells, and post-vaccination responses remained about the same in each patient (FIG. 3). A similar study was not done for HLA-A3 and A24 positive patients because there are no published influenza M1 epitopes known to bind these HLA molecules.

Figure 4A:
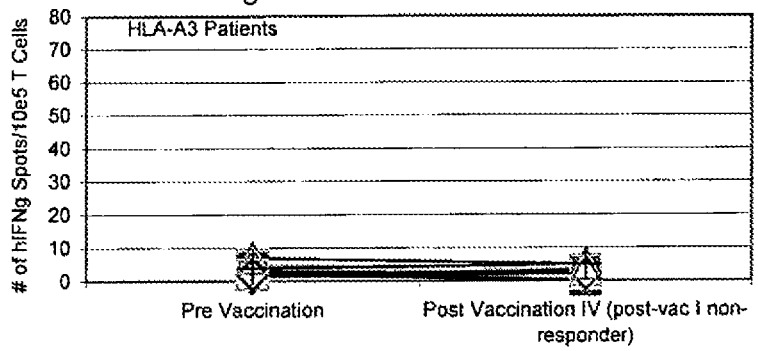
FIG. 4A to 4D shows an ELISPOT analysis of CD8+ T cells from PBMCs. No post-vaccination induction was observed of PSCA-specific T cells in DTH responders or non-DTH responders who received an allogeneic GM-CSF-secreting tumor vaccine for pancreatic cancer.
Figure 4B:
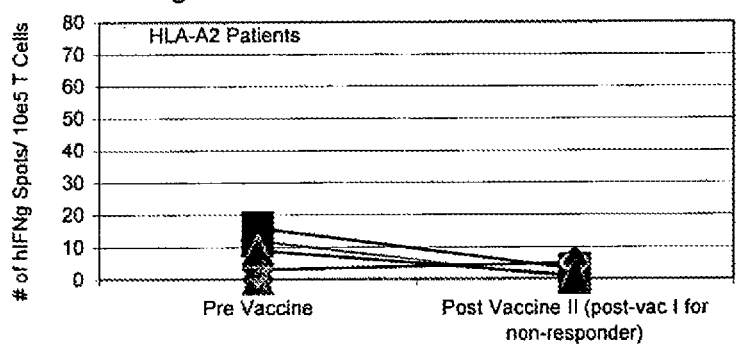
Figure 4C:
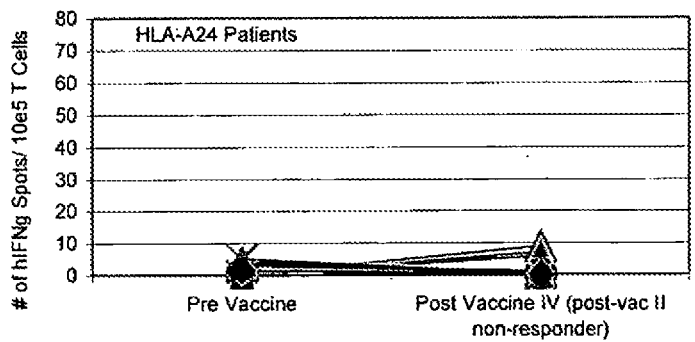
Figure 4D:
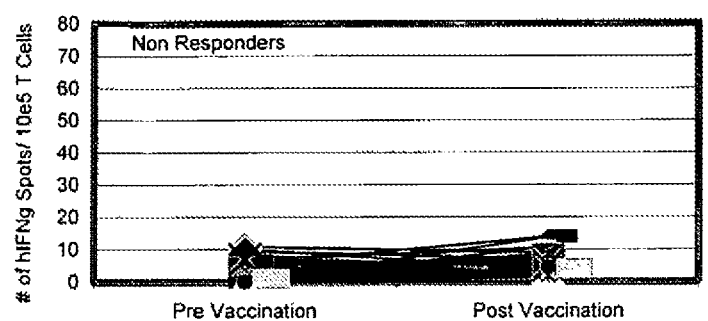

We evaluated the lymphocytes from the same 14 patients for the post-vaccination induction of CD8+ T lymphocytes directed against a second overexpressed antigen, PSCA. In contrast to mesothelin, PSCA did not elicit an immune response in the 3 DTH responders. Again, we synthesized the top two ranking epitopes for HLA-A2, HLA-A3, and HLA-A24 favored by both algorithms and analyzed these according to the same protocols used in the mesothelin experiments. We did not see any post-vaccination induction of PSCA-specific T cells in any of the patients; therefore, we synthesized 4 additional PSCA peptides for each HLA class I molecule to ensure that we had not missed the immunogenic epitope. Analysis of these peptides also failed to demonstrate a post-vaccination induction of PSCA-specific CD8+ T cell responses (FIGS. 4A, 4B, and 4C, respectively). PSCA specific responses could not be demonstrated in the eight non-responders as well (FIG. 4d). This result further supports our finding that mesothelin is a relevant pancreatic tumor antigen because there were no vaccine induced immune responses to PSCA even though they are similarly overexpressed in pancreatic cancer on SAGE analysis. In addition, the PSCA data demonstrate that overexpression of a protein in a tumor is insufficient to predict the protein's utility as a vaccine target.

Figure 5:
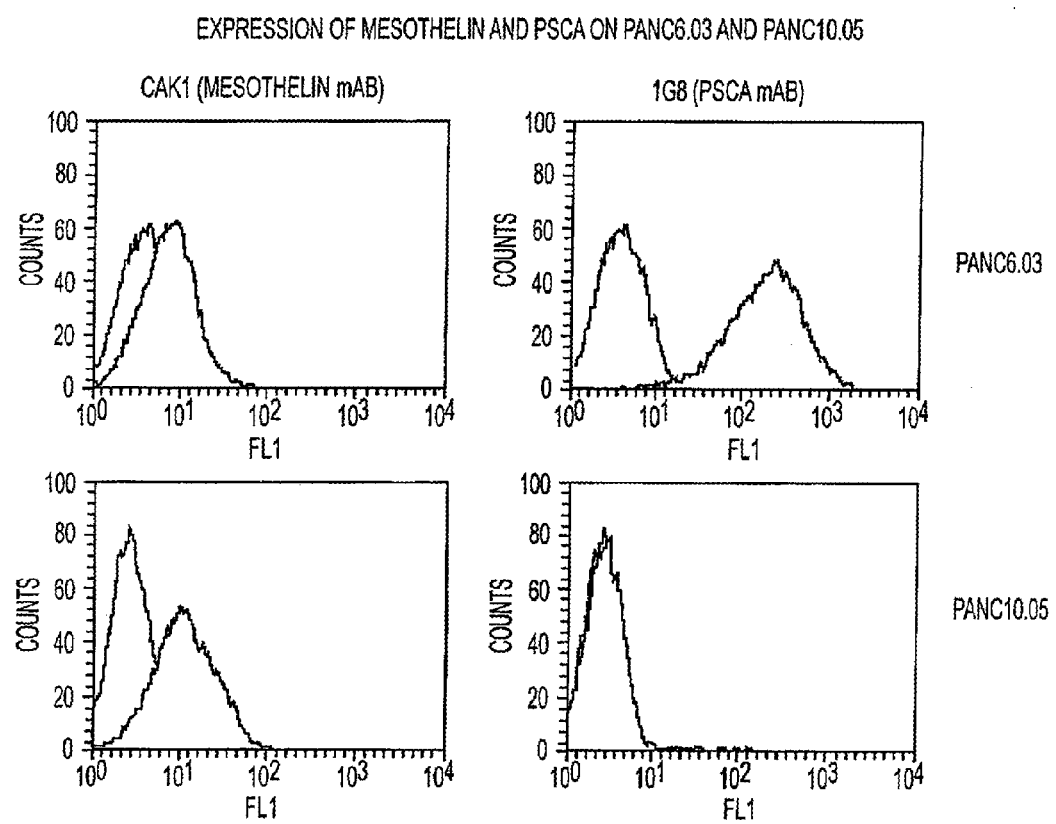
FIG. 5 shows expression of surface Mesothelin and PSCA on Panc 6.03 and Panc 10.05 vaccine lines. The pancreatic tumor vaccine lines Panc 6.03 (top two panels) and Panc 10.05 (bottom two panels) were analyzed by flow cytometry for their levels of surface mesothelin and PSCA using the mesothelin specific monoclonal antibody CAK1 (left panels) and the PSCA specific monoclonal antibody 1G8 (right panels) as the primary antibody and goat anti-mouse IgG FITC as the secondary antibody. The solid line represents the isotype control, the green shaded area represents mesothelin staining, and the pink shaded area PSCA staining.

Flow cytometry analysis of mesothelin and PSCA expression by the two allogeneic vaccine cell lines is shown in FIG. 5. Interestingly, mesothelin is expressed equally by both vaccine cell lines whereas PSCA is only expressed by one of the vaccine cell lines (Panc 6.03).

Materials and Methods: CD8+ M1 specific T cell lines. M1 specific T cell lines were generated by repeated in vitro stimulation of HLA-A201 positive PBL initially with irradiated autologous dendritic cells followed by irradiated autologous Ebstein Barr Virus (EBV) transformed B cells, both pulsed with the HLA-A201 restricted epitope. This line was stimulated biweekly using autologous EBV cells that were pulsed with 10 µg peptide/ml of their respective peptides at 37° C. for 2 hours, washed twice with RPMI-1640, and irradiated with 10,000 rads. T cells were stimulated at a 1:2 T cell to EBV cell ratio in T cell media (RPMI-1640, 10% human serum (pooled serum collected at the Johns Hopkins Hemapheresis Unit) containing 200 µM L-Glutamine, 50 units-µg/ml Pen/Strep, 1% NEAA, and 1% Na-Pyruvate) supplemented with 20 cetus units IL-2/well and 10 ng/well IL-7. This line was used a positive control T cell line in all assays.

Materials and Methods: Flow cytometry. The expression of mesothelin and PSCA on the vaccine lines was evaluated by flow cytometry analysis. The vaccine lines were washed twice and resuspended in "FACS" buffer (HBSS supplemented with 1% PBS, 2% FBS, and 0.2% sodium azide), then stained with mouse monoclonal mesothelin (CAK1) (Signet Laboratories, Dedham, Mass.) or mouse monoclonal to PSCA (clone 1G8, obtained from R.E.R.) followed by FITC-labeled goat antimouse IgG (BD PharMingen, San Jose, Calif.) for flow analysis in a FACScan analyzer (BD Immunocytometry Systems).

These data demonstrate that mesothelin-specific CD8+ T cells are detected following a single vaccination with an allogeneic GM-CSF secreting tumor vaccine in DTH responders but not in non-DTH responders. The patients treated on the reported vaccine study received an initial vaccination 8-10 weeks following pancreaticoduodenectomy and 4 weeks prior to receiving a six month course of adjuvant chemoradiation (27). Six of these patients remained disease-free at the end of the six months and received up to 3 more vaccinations given one month apart. Repeat ELISPOT studies were performed on serial CD8+ T cell enriched PBL samples from these six patients following multiple vaccine treatments to assess the effect of chemoradiation and multiple vaccinations on mesothelin-specific T cell responses.

Figure 6:
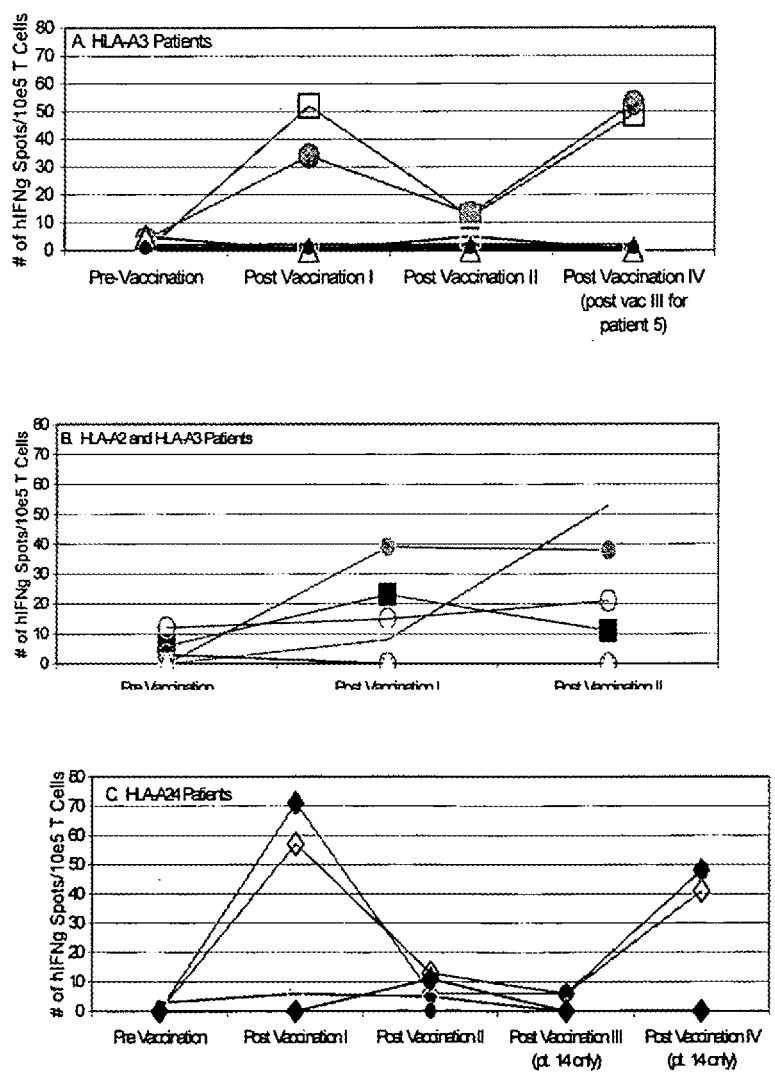
FIGS. 6A to 6C show that mesothelin-specific CD8+ T cells are detected following multiple vaccinations with an allogeneic GM-CSF secreting tumor vaccine in DTH-responders but not in non-DTH responders.

As shown in FIG. 6, two of the three DTH responders demonstrated decreased mesothelin-specific T cell responses following the second vaccination. In both patients, mesothelin-specific T cell responses returned to levels achieved after the initial vaccination by the fourth vaccination. The suppressed mesothelin-specific T cell responses that were observed following the second vaccine are likely the result of the chemotherapy that each patient received between the first and second vaccination. Interestingly, one of the three patients demonstrated similar mesothelin-specific T cell responses after the first and second vaccination. This DTH responder only received two vaccines because she subsequently developed a late autoimmune antibody mediated complication attributed to the Mitomycin-C that required medical intervention and withdrawal from the vaccine study. In contrast, repeated vaccination failed to induce mesothelin-specific T cell responses in those patients who did not demonstrate an initial mesothelin-specific T cell response following the first vaccination (FIG. 6).

These data describing CD8+ T cell responses induced by an allogeneic GM-CSF-secreting pancreatic tumor vaccine support the following conclusions. First, mesothelin can serve as an in vitro biomarker of vaccine-induced immune responses that correlate with in vivo responses in patients with pancreatic adenocarcinoma. Second, the recognition of mesothelin and lack of recognition of another overexpressed gene product, PSCA, by uncultured post-vaccination CD8+ T cells from patients that demonstrated evidence of in vivo immune responses in association with clinical responses validates this antigen identification approach as a rapid functional genomic-based approach for identifying immune relevant tumor targets of CD8+ T cells.

Mesothelin is a 40 kilodalton transmembrane glycoprotein member of the mesothelin/megakaryocyte potentiating factor (MPF) family expressed by most pancreatic adenocarcinomas (36), (37-39). It has also been reported to be expressed by ovarian cancers, mesotheliomas, and some squamous cell carcinomas (37-39). Mesothelin is known to be attached to the cell membrane by a glycosylphosphatidyl-inositol anchor and is postulated to function in cell adhesion (36). Mesothelin and other members of its gene family exhibit limited normal tissue expression. It therefore meets three important criteria that strongly favor its potential use as an immunogen in the future development of antigen-based vaccines for patients with pancreatic adenocarcinoma and other tumor types that overexpress mesothelin: it is widely shared by most pancreatic and ovarian cancers, it has a limited expression in normal tissues, and it induces CD8+ T cell responses following vaccination with tumor cells that express this antigen.

The identification of shared, biologically relevant tumor antigens provides the opportunity to design antigen-based vaccines that have the potential to be more efficient at inducing anti-tumor immunity than current whole cell vaccines. In addition, scale up of recombinant antigen-based approaches is technically more feasible than currently employed whole tumor cell vaccines. However, recombinant antigen-based vaccines require identification of antigens that are both broadly expressed by patients and that are immunogenic. Until now, T cell screening of cDNA libraries, antibody screening of phage display libraries, or the biochemical elution and purification of antigens bound to MHC have identified the majority of known tumor antigens, many of which appear to derive from shared, non-mutated genes that are either overexpressed by or reactivated in tumor cells relative to normal tissue (3-13). Unfortunately, this expanding list of tumor associated antigens recognized by T cells is limited mostly to melanoma because of the technical difficulty of isolating and propagating T cell lines and clones from vaccinated patients with other types of cancer. The tumor antigen identification approach disclosed herein is feasible because it only requires a database of differentially expressed genes within a given tumor, and banked, uncultured bulk PBL from vaccinated patients. Therefore, this antigen identification approach is rapid and can be generalized to most types of cancer. In addition, the use of uncultured lymphocytes rather than T cell lines and clones that have been in long term culture provide the advantage of identifying new biologically relevant immune targets.

PSCA is a second gene product that was found to be overexpressed in our SAGE pancreatic gene expression database. In fact, PSCA was shown to be overexpressed at higher levels than even mesothelin. However, post-vaccination PSCA specific T cell responses were not detected in the DTH responders and DTH non-responder patients. It is unclear at this time why a GM-CSF secreting allogeneic vaccine induces T cell responses to one overexpressed antigen and not to a second similarly overexpressed antigen. It is possible that these two antigens are differently processed and presented during the initial priming event (58).

In this study we also demonstrate that mesothelin-specific T cells can be induced against at least six different peptides presented by three different HLA-A locus alleles. This finding provides further support that mesothelin can serve as a shared antigen. In this study, the highest ranking antigenic epitopes predicted to be the best HLA-A allele binding epitopes based on their motif, bound to their respective HLA alleles and were also recognized by mesothelin-specific T cells. Reports analyzing other tumor antigens have found that the highest ranking epitopes do not necessarily correlate with optimal recognition by T cells (25). We also performed the computer algorithms on two melanoma antigens, tyrosinase and MAGE 1, to determine how their published HLA-A2 binding peptides rank by this method. We found that our HLA-A2 binding mesothelin epitopes were given similar scores as the known tyrosinase and MAGE 1 HLA-A2 binding epitopes. This was also true for the published HLA-A2 HIV GAG and HLA-A3 HIV NEF epitopes that were used as control antigens in our analyses. Choosing epitopes that rank high by both algorithms appears to be an important predictor of the probability of binding to the respective HLA molecule.

We have developed a functional genomic approach that identified a candidate pancreatic tumor antigen. This approach to antigen identification facilitates the identification of other human cancer antigens that are biologically relevant immune targets. The correlation of in vitro T cell responses with in vivo measures of response validates the biologic importance of this approach. This approach is rapid and feasible and can easily be adapted to identify antigens expressed by other cancer types. This in turn, should accelerate the development of recombinant antigen-based vaccines for most human cancer treatment.

References For Background Of The Invention And For Examples 1-4

1. Zhang, L., Zhou, W., Velculescu, V. E., Kern, S. E., Hruban, R. H. et. al. Genome expression profiles in normal and cancer cells. *Science*, 276: 1268-1272, (1997).
2. Zhang, W., Laborde, P. M., Coombes, K. R., Berry, D. A. & Hamilton, S. R. Cancer genomics: promises and complexities. *Clin Cancer Res*, 7: 2159-2167, (2001).
3. Boon, T., Coulie, P. G. & Van den Eynde, B. Tumor antigens recognized by T cells. *Immunol Today*, 18: 267-268, (1997).
4. Rosenberg, S. A. Progress in human tumour immunology and immunotherapy. *Nature*, 411: 380-384, (2001).
5. Rosenberg, S. A. Identification of cancer antigens: impact on development of cancer immunotherapies. *Cancer J Sci Am*, 6: S208-S217, (2000).
6. Chen, Y. T. Cancer vaccine: identification of human tumor antigens by SEREX. *Cancer J Sci Am*, 6: S208-S217, (2000).
7. Nakatsura, T., Senju, S., Ito, M., Nishimurs, Y & Itoh, K. Cellular and humoral immune response to a human pancreatic cancer antigen, coactosin-like protein, originally defined by the SEREX method. *Eur. J. Immunol*, 32: 826-836, (2002).
8. Scanlan, M. J., Welt, S., Gordon, C. M., Chen, Y-T., Gure, A. O. et al. Cancer-related serological recognition of human colon cancer: identification of potential diagnostic and immunotherapeutic targets. *Can Res.*, 62: 4041-4047, (2002).
9. Monji, M., Senju, S., Nakatsura, T., Yamada, K., Sawatsubashi, M., et al. Head and neck cancer antigens recognized by the humoral immune system. *Biochem Biophys Res Commun*, 294: 734-741, (2002).
10. Mashino, K., Sadanaga, N., Tanaka, F., Yamaguchi, H., Nagashima, H. et al. Expression of multiple cancer-testis antigen genes in gastrointestinal and breast carcinomas. *Br J cancer*, 85: 713-720, (2001).
11. Skipper, J. C., Gulden, P. H., Hendrickson, R. C., Harthun, N., Caldwell, J. A. et al. Mass-spectrometic evaluation of HLA-A*0201-associated peptides identifies dominant naturally processed forms of CTL epitopes from MART-1 and gp 100. *Int J Cancer*, 82: 669-677, (1999).
12. Hogan, K. T., Eisinger, D. P., Cupp, S. B., Lekstrom, K. J., Deacon, D. D. et al. The peptide recognized by HLA-A68.2 restricted, squamous cell carcinoma of the lung-specific cytotoxic T lymphocytes is derived from a mutated elongation factor 2 gene. *Cancer Res*, 58: 5144-5150, (1998).
13. Cox, A. L., Skipper, J., Chen, Y., Henderson, R. A., Darrow, T. L. et al. Identification of a peptide recognized by five melanoma-specific human cytotoxic T cell lines. *Science*, 264: 716-719, (1994).
14. Jager, D., Jager, E. & Knuth, A. Vaccination for malignant melanoma: recent developments. *Oncology*, 60:1-7, (2001).
15. Lockhart, K. J., Dong, H., Byrne, M. C., Follettie, M. T., Gallo, M. V. et al. Expression monitoring by hybridizationto high-density oligonucleotide arrays. *Nat. Biotechnol*, 14: 1675-1680, (1996).
16. Schena, M., Shalon, D., Davis, R. W. & Brown, P. O. Quantitative monitoring of gene expression patterns with a complementary DNA microarray. *Science*, 270: 467-470, (1995).
17. Velculescu, V. E., Zhang, L., Vogelstein, B., & Kinzler, K. W. Serial analysis of gene expression. *Science*, 270: 484-487, (1995).
18. Duggan, D. J., Bittner, M., Chen, Y., Meltzer, R. & Trent, J. M. Expression profiling using cDNA microarrays. *Nat Genet*, 21: 10-14, (1999).
19. Khan, J., Bittner, M. L., Chen, Y., Meltzer, P. S. & Trent, J. M. DNA microarray technology: the anticipated impact on the study of human disease. *Biochem Biophys Acta*, 1423: M17-M28, (1999).
20. Argani, P., Rosty, C. Reiter, R. E., Wilenz, R. E., Murgesan, S. R. et al. Discovery of new markers of cancer through serial analysis of gene expression: prostate stem cell antigen is overexpressed in pancreatic adenocarcinoma. *Cancer Res*, 61: 4320-4324, (2001).
21. Argani, P., Iacobuzio-Donahue, C. Ryu, B., Rosty, C. Goggins, M. et al. Mesothelin is overexpressed in the vast majority of ductal adenocarcinomas of the pancreas: identification of a new pancreatic cancer marker by serial analysis of gene expression (SAGE). *Clin Cancer Res*, 3862: 3862-3868, (2001).
22. Ryu, B., Jones, J., Blades, N. J., Parmigiani, G., Hollingsworth, M. A., et al. Relationships and differentially expressed genes among pancreatic cancers examined by large-scale serial analysis of gene expression. *Cancer Res*, 62: 819-826, (2002).
23. Parker, K. C., Bednarek, M. A., & Coligan, J. E. Scheme for ranking potential HLA-A2 binding peptides based on independent binding of individual peptide side chains. *J Immunol*, 152: 163-175, (1994).
24. Rammensee, H.-H., Bachmann, J., Emmerich, N. P. N., Bachor, O. A. & Stevanovic, S. SYFPEITHI: database for MHC ligands and peptide motifs. *Immunogenetics*, 50: 213-219, (1999).
25. Lu, J. C., E. Use of two predictive algorithms of the world wide web for the identification of tumor-reactive T-cell epitopes. *Cancer Res*, 60: 5223-5227, (2000).
26. Salter, R. D., Howell, D. N. & Cresswell, P. Genes regulating HLA class I antigen expression in T-B lymphoblast hybrids. *Immunogenetics*, 21: 235-246, (1985).
27. Jaffee, E. M., Hruban, R. H., Biedrzycki, B., Laheru, D., Schepers, K. et al. Novel allogeneic granulocyte-macrophage colony-stimulating factor-secreting tumor vaccine for pancreatic cancer: phase I trial of safety and immune activation. *J. Clin. Onc*, 19: 145-156, (2001).
28. Bednarek, M. A., Sauma, S. Y., Gammon, M. C., Porter, G., Tamhanker, S. et al. The minimum peptide epitope from the influenza matrixprotein. *J Immunol*, 147: 4047-4053, (1991).
29. Altman, J. D., Moss, P. A., Goulder, P. J., Barouch, D. H., McHeyzer-Williams, M. G. et al. Phenotypic analysis of antigen-specific T lymphocytes. *Science*, 274: 94-96, (1996).
30. Propato, A., Schiaffella, E., Vicenzi, E. Francavilla, V., Baloni, L. et al. Spreading of HIV-specific CD8+ T-cell repertoire in long-term nonprogressors and its role in the control of viral load and disease activity. *Human Immunol*, 62: 561-576, (2001).
31. Kang, X., Kawankami, Y., el-Gamil, M., Wang, R., Sakaguchi, K. et al. Identification of a tyrosinase epitope recognized by HLA-A24 restricted, tumor-infiltrating lymphocytes. *J Immunol*, 155: 1343-1348, (1995).
32. Anderson, K. S., Alexander, J., Wei, M. & Cresswell, P. Intracellular Transport of class I MHC molecules in antigen processing mutant cell lines. *J Immunol*, 151: 3407-3419, (1993).
33. Miyahira, Y., Kenichiro, M., Rodriguez, M., Rodriguez, J. R., Esteban, M. et al. Quantification of antigen specific $CD8^+$ T cells using an ELISPOT assay. *J Immunol Methods*, 181: 45-54, (1995).

34. McCutcheon, M., Wehner, N., Wensky, A., Kushner, M., Doan, S. et al. A sensitive ELISPOT assay to detect low-frequency human T lympocytes. *J Immunol Methods*, 210: 149-166, (1997).

35. Schmittel, A., Keilholz, U. & Scheibenbogen, C. Evaluation of the interferon-γ ELISPOT-assay for the quantification of peptide specific T lymphocytes from peripheral blood. *J Immunol Methods*, 210: 167-174, (1997).

36. Chang, K. P., I. Molecular cloning of mesothelin, differentiation antigen present on mesothelium, mesotheliomas, and ovarian cancers. *Proc Natl Acad. Sci. USA*, 93: 136-140, (1996).

37. Scholler, N., Fu, N., Yang, Y., Ye, Z., Goodman, G. E., et al. Soluble member(s) of the mesothelin/megakaryocyte potentiating factor family are detectable in sera from patients with ovarian carcinoma. *Proc Natl Acad. Sci. USA*, 96: 11531-11536, (1999).

38. Chowdhury, P. S., VIner, J. L., Beers, R., Pastan, I. Isolation of high-affinity stable single-chain Fv specific for mesothelin from DNA-immunized mice by phage display and construction of recombinant immunotoxin with anti-tumor activity. *Proc Natl Acad. Sci. USA*, 95: 669-674, (1998).

39. Hassan, R., Viner, J. L., Wang, Q. C., Margulies, I. Kreitman, R. J., & Pastan, I. Anti-tumor activity of K1-LysPE38QQR, an immunotoxin targeting mesothelin, a cell surface antigen overexpressed in ovarian cancer and malignant mesothelioma. *J Immunother.*, 23: 472-479, (2000).

40. Chang, K. P., I. & Willingham, M. C. Isolation and characterization of monaclonal antibody, K1, reactive with ovarian cancers and normal mesothelium. *Int J Cancer*, 50: 373-381, (1992).

41. Simons, J. W., Jaffee, E. M., Weber, C. E., Levitsky, H. I., Nelson, W. G., et al. Bioactivity of autologous irradiated renal cell carcinoma vaccines generated by ex vivo granulocyte-macrophage colony-stimulating factor gene transfer. *Cancer Res*, 57: 1537-1546, (1997).

42. Soiffer, R., Lynch, T., Mihm, M., Jung, K., Rhuda, C. et at Vaccination with irradiated autologous melanoma cells engineered to secrete human granulocyte-macrophage colony-stimulating factor generates potent antitumor immunity in patients with metastatic melanoma. *Proc Natl Acad. Sci. USA*, 95: 13141-13146, (1998).

43. Sokol, J. E. Measurement of delayed skin test responses. *N Engl J Med*, 29: 501-503, (1995).

44. McCune, C. S., O'Donnell, R. W., Marquis, D. M. & Sahasrabudhe, D. M. Renal cell carcinoma treated by vaccines for active specific immunotherapy: correlation of survival with skin testing by autologous tumor cells. *Cancer Immunol Immunother*, 32: 62-66, (1990).

45. Oren, M. E. H., R. B. Delayed cutaneous hypersensitivity reactions to membrane extracts of human tumour cells. *Clin Exp Immunol*, 9: 45-56, (1977).

46. Hoover Jr., H. C., Surdyke, M., Dangel, R. B., Peters, L. C. & Hanna Jr., M. G. Delayed cutaneous hypersensitivity to autologous tumor cells in colorectal cancer patients immunized with an autologous tumor cell: bacillus calmette-guerin vaccine. *Cancer Res*, 44: 1671-1676, (1984).

47. Berd, D., Maguire Jr., H. C., McCue, P. & Mastrangelo, M. J. Treatment of metastatic melanoma with an autologous tumor-cell vaccine: clinical and immunologic results in 64 patients. *J Clin Oncol*, 8: 1858-1867, (1990).

48. Berd, D., Maguire Jr., H. C., & Mastrangelo, M. J. Induction of cell-mediated immunity to autologous melanoma cells and regression of metastases after treatment with a melanoma cell vaccine preceded by cyclophoshamide. *Cancer Res*, 46: 2572-2577, (1986).

49. Disis, M. L., Schiffman, K., Gooley, T. A., McNeel, D. G., Rinn, K. et al. Delayed-type hypersensitivity response is a predictor of peripheral blood T-cell immunity after HER-2/neu peptide immunization. *Clin Cancer Res*, 6: 1347-1350, (2000).

50. Disis, M. L., Gooley, T. A., Rinn, K., Davis, D., Piepkorn, M. et al. Generation of T-cell immunity to the HER-2/neu protein after active immunization with HER-2/neu peptide-based vaccines. *J Clin Oncol*, 20: 2624-2632, (2002).

51. Knutson, K. L., Schiffman, K., Cheever, M. A. & Disis, M. L. Immunization of cancer patients with a HER-2/neu, HLA-A2 peptide, p369-377, results in short-lived peptide-specific immunity. *Clin Cancer Res*, 8: 1014-1018, (2002).

52. Gjertsen, M. K., Buanes, T., Rosseland, A. R., Bakka, A., Gladhaug, I. et at Intradermal ras peptide vaccination with granulocyte-macrophage colony-stimulating factor as adjuvant: Clinical and immunological responses in patients with pancreatic adenocarcinoma. *Int J Cancer*, 92: 441-450, (2001).

53. Pittet, M. J., Speiser, D. E., Lienard, D., Valmori, D., Guillaume, P. et al. Expansion and functional maturation of human tumor antigen-specific CD8+ T cells after vaccination with antigenic peptide. *Clin Cancer Res*, 7: 796s-803s, (2001).

54. Abrams, S. I., Khleif, S. N., Bergmann-Leitner, E. S., Kantor, J. A., Chung, Y. et al. Generation of stable $CD4^+$ and $CD8^+$ T cell lines from patients immunized with ras oncogene-derived peptides reflecting codon 12 mutations. *Cellular Immunol*, 182: 137-151, (1997).

55. DiFronzo, L. A., Gupta, R. K., Essner, R., Foshag, L. J., O'Day, S. J., et al. Enhanced humoral immune response correlates with improved disease-free and overall survival in american joint committee on cancer stage 11 melanoma patients receiving adjuvant polyvalent vaccine. *J Clin Oncol*, 20: 3242-3248, (2002).

56. Hodi, F. S., Schmollinger, J. C., Soiffer, R. J., Saliga, R., Lynch, T. et al. ATP6S1 elicits potent humoral responses associated with immune-mediated tumor destruction. *Proc Natl Acad. Sci. USA*, 99: 6919-6924, (2002).

57. Moulton, H. M., Yoshihara, P. H., Mason, D. H., Iverson, P. L., & Triozzi, P. L. Active specific immunotherapy with a β-human chorionic gonadotropin peptide vaccine in patients with metastatic colorectal cancer: antibody response is associated with improved survival. *Clin Cancer Res*, 8: 2044-2051, (2002).

58. Kedl R. M., R. W. A., Hildeman D. A., Schaefer B., Mitchell T., Kappler J., Marrack P. T cells Compete for Access to Antigen-bearing Antigen-presenting Cells. Journal Experimental Medicine, 192: 1105-1113, 2000.

59. Ochsenbein, A. F., Sierro, S., Odermatt, B., Pericin, M., Karrer, U. et al. Roles of tumour localization, second signals, and cross priming in cyotoxic T-cell induction. Nature, 411: 1058-1064, (2001).

60. Huang, A. Y., Bruce, A. T., Pardoll, D. M., Levitsky, H. I. In vivo cross-priming of MHC class I-restricted antigens requires the TAP transporter. *Immunity*, 4: 349-355, (1996).

61. Huang, A. Y. C., Golumbek, P., Ahmadzeadeh, M., Jaffee, E. M., Pardoll, D. M., et al. Role of bone marrow-derived cells in presenting MHC class I-restricted tumor antigens. *Science*, 264: 961-965, (1994).

62. Norbury, C. C., Princiotta, M. F., Bacik, I., Brutkewicz, R. R., Wood, P. et at Multiple antigen-specific processing pathways for activating naïve $CD8^+$ T cells in vivo. *J Immunol*, 166: 4355-4362, (2001).

63. den Haan, J. M. B., M. J. Antigen presentation to CD8+ T cells: cross priming in infectious diseases. *Curr Opin Immunol,* 13: 437-441, (2001).
64. Kovacsovics-Bankowski, M., & Rock, K. L. A phagosome-to-cytosol pathway for exogenous antigens presented on MHC class I molecules. *Science,* 267: 243-246, (1995).
65. Albert, M. L., Sauter, B. & Bhardwaj, N. Dendritic cells acquire antigen from apoptotic cells induce class I-restricted CTLs. *Nature,* 392: 86-89, (1998).
66. Berard, F., Blanco, P., Davoust, J., Neidhart-Berard, E. M., Nouri-Shirazi, M. et al. Cross-priming of naïve CD8 T cells against melanoma antigens using dendritic cells loaded with killed allogeneic melanoma cells. *J Exp Med,* 192: 1535-1544, (2000).
67. Hoffmann, T. K., Meidenbauer, N., Dworacki, G., Kanaya, H. & Whiteside, T. L. Generation of tumor-specific T lymphocytes by cross-priming with human dendritic cells ingesting apoptotic tumor cells. *Cancer Res,* 60: 3542-3549, (2001).
68. John, M., Flam, M. & Palma, N. Ten-year results of chemoradiation for anal cancer: focus on late morbidity. *Int J Radiat Oncl Biol Phys,* 34: 65-69, (1996).

Example 5

Construction of Mouse Tumor Cells by Co-transformation with HPV-16 E6 and E7 and Activated ras Oncogene. Primary peritoneal cells of C57BL/6 mice were immortalized by HPV-16 E6 and E7 and then transformed with pEJB expressing activated human c-Ha-ras gene. This co-transformation produced a tumorigenic cell line.

C57BL/6 mouse peritoneal cells were collected and washed with 1×HBSS. The primary single cell suspension was cultured in vitro in RPMI1640, supplemented with 10% fetal calf serum, 50 units/ml penicillin/streptomycin, 2 mM L-glutamine, 1 mM sodium pyruvate, and 2 mM nonessential amino acids, and grown at 370 C. with 5% CO2. Transduction of HPV-16 E6 and E7 genes into primary peritoneal cells was performed using the LXSN16E6E7 retroviral vector, kindly provided by Denise A. Galloway (Fred Hutchinson Cancer Research Center, Seattle, Wash.) (Halbert, et al., (1991) J Virol, 65:473-478). HPV-16 E6- and E7-containing LXSN16E6E7 was used to infect CRIP cells to generate recombinant virus with a wide host range. Primary peritoneal cells were immortalized by transduction as described previously (Halbert, et al., (1991) J Virol, 65:473-478). Following transduction, the retroviral supernatant was removed, and cells were grown in G418 (0.4 mg/ml) culture medium for an additional 3 days to allow for integration and expression of recombinant retroviral genes. The immortalized lung (E6+ E7+) cells were then transduced with pVEJB expressing activated human c-Ha-ras gene, kindly provided by Chi V. Dang (The John Hopkins Hospital, Baltimore, Md.), and selected with G418 (0.4 mg/ml) and hygromycin (0.2 mg/ml).

Example 6

Characterization of Histological and Pathological Features of WF-3. 5×104 WF-3 tumor cells were injected into C57BL/6 mice intraperitoneally. 4 weeks later, mice were sacrificed to examine the formation of ascites and tumors. Removed organs were fixed with 4% buffered formaldehyde and histological sections were made, followed by routine hematoxylin-eosin staining Slides were observed under a light microscope.

Mice were injected with 5×104 WF-3 tumor cells intraperitoneally and sacrificed 4 weeks later. This cell line was capable of generating ascites in mice challenged with tumor cells intraperitoneally (see FIG. 7A). Morphologically, WF-3 tumor cells showed a papillary architecture resembling serous tumors found in the human ovary/peritoneum (FIG. 1B). Furthermore, the tumor showed a high level of mitotic activity, pleiomorphic nuclei, abnormal mitosis, and a high nuclear/cytoplasmic ratio, consistent with a highly malignant neoplasm (see FIG. 7C).

Figure 7:
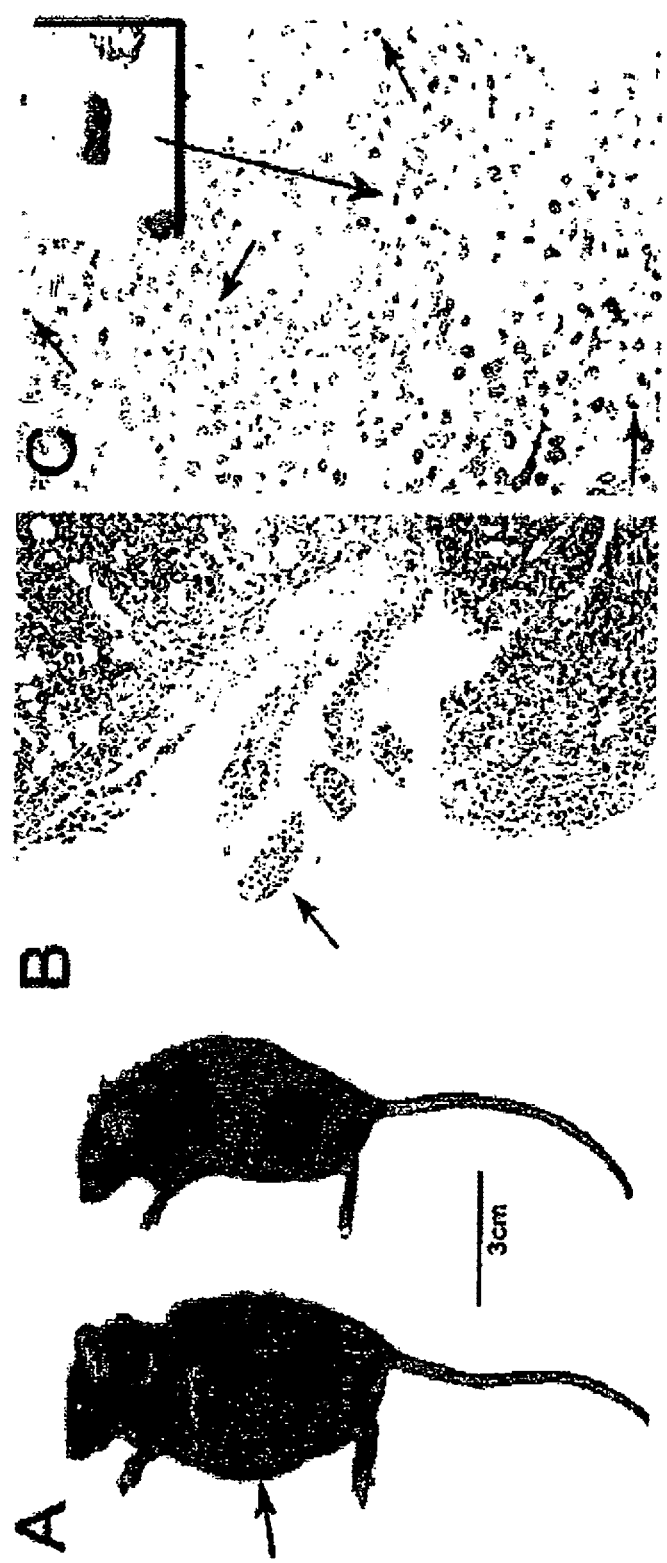
FIGS. 7A to 7C show the generation and characterization of an ascitogenic ovarian tumor cell line (WF-3) in mice. WF-3 tumor cells were injected into C57BL/6 mice intraperitoneally at a dose of $1\times10^5$ cells/mouse. Mice were euthanized 4 weeks after tumor challenge (FIG. 7A) Representative gross picture to demonstrate ascites formation in mice. Note: Mice developed significant ascites with an increase in abdominal girth 4 weeks after tumor challenge.

FIG. 7 shows the generation and characterization of an ascitogenic ovarian tumor cell line (WF-3). WF-3 tumor cells were injected into C57BL/6 mice intraperitoneally at a dose of 1×105 cells/mouse. Mice were euthanized 4 weeks after tumor challenge (see FIG. 7A) Representative gross picture to demonstrate ascites formation in mice. Note: Mice developed significant ascites with an increase in abdominal girth 4 weeks after tumor challenge. FIG. 7B shows hematoxylin and eosin staining of the explanted tumors viewed at 100× magnification. The tumors displayed a papillary configuration, morphologically consistent with tumors derived from the peritoneum or ovaries. FIG. 7C shows tumors viewed at 400× magnification. The inset displays the features of a WF-3 tumor cell in greater detail.

Example 7

MHC Class I and Class II Presentation of WF-3 Tumor Cells. WF-3 tumor cells were harvested and prepared for flow cytometry analysis. Anti-H-2 Kb/H-2 Db monoclonal antibody or anti-1-Ab monoclonal antibody was added for the detection of MHC class I and class II expression on WF-3 tumor cells.

WF-3 tumor cells were harvested, trypsinized, washed, and resuspended in FACScan buffer. Anti-H-2 Kb/H-2 Db monoclonal antibody (Clone 28-8-6, PharMingen, San Diego, Calif.) or anti-1-Ab monoclonal antibody (Clone 25-9-17, PharMingen, San Diego, Calif.) was added and incubated for 30 min on ice. After washing twice in FACScan buffer, FITC-conjugated goat anti-mouse antibody (Jackson ImmunoResearch Lab. Inc., West Grove, Pa.) was added and incubated for 20 min on ice. Samples were resuspended in FACScan buffer. Analysis was performed on a Becton Dickinson FACScan with CELLQuest software (Becton Dickinson Immunocytometry System, Mountain View, Calif.).

Figure 8A:
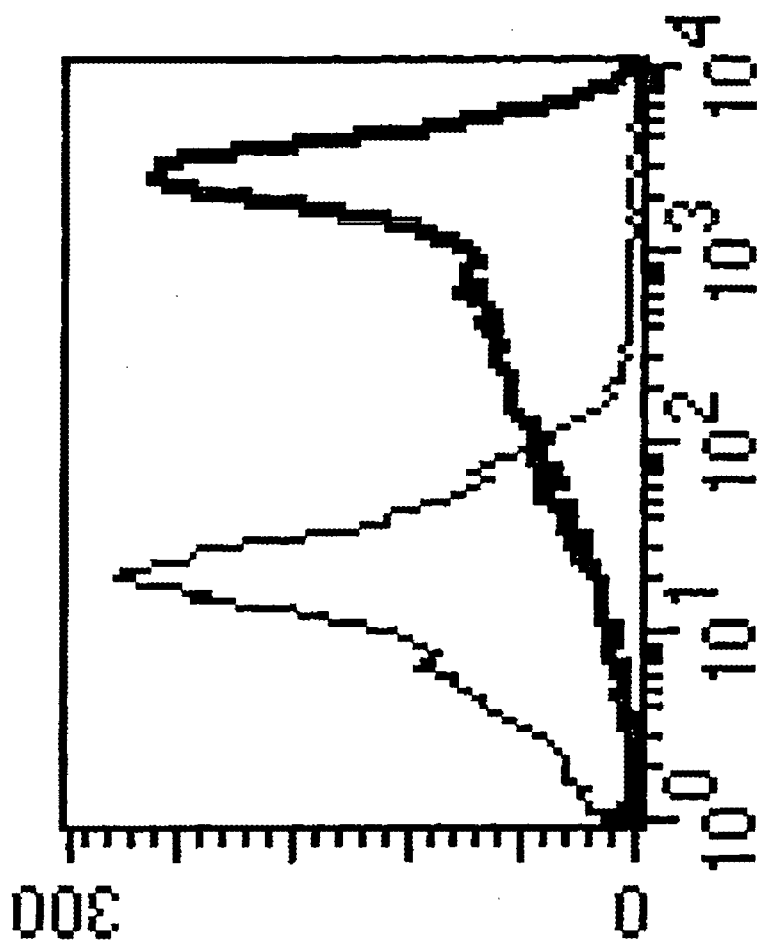

Our data indicate that WF-3 is positive for MHC class I expression (FIG. 8A) but negative for MHC class II expression (FIG. 8B). In particular, FIG. 8 shows the MHC class I and II presentation on WF-3 tumor cells. WF-3 tumor cells were harvested, trypsinized, washed, and resuspended in FACSCAN buffer. Anti-H-2 Kb/H-2 Db monoclonal antibody or anti-1-Ab monoclonal antibody was added, followed by flow cytometry analysis to detect MHC class I and class II expression on WF-3 tumor cells. FIG. 8A shows WF-3 tumor cells which were positive for MHC class I presentation (thick line) compared to the MHC class I-negative control (thin line). FIG. 8B shows the WF-3 tumor cells which were negative for MHC class II presentation. The thin line indicates staining of the MHC class II-negative control.

Example 8

Determination of Minimal Tumor Dose of WF-3 Tumor Cells to Lead to Formation of Lethal Ascites. WF-3 tumor cells were injected into C57BL/6 mice intraperitoneally at various doses (1×104, 5×104, 1×105, and 1×106 cells/mouse). Mice were monitored twice a week for formation of ascites and tumors and sacrificed after 90 days. For survival following tumor challenge, mice were challenged intraperitoneally with various doses of WF-3 (1×104, 5×104, 1×105, and 1×106 cells/mouse) and monitored for their survival after tumor challenge.

Figure 9B:
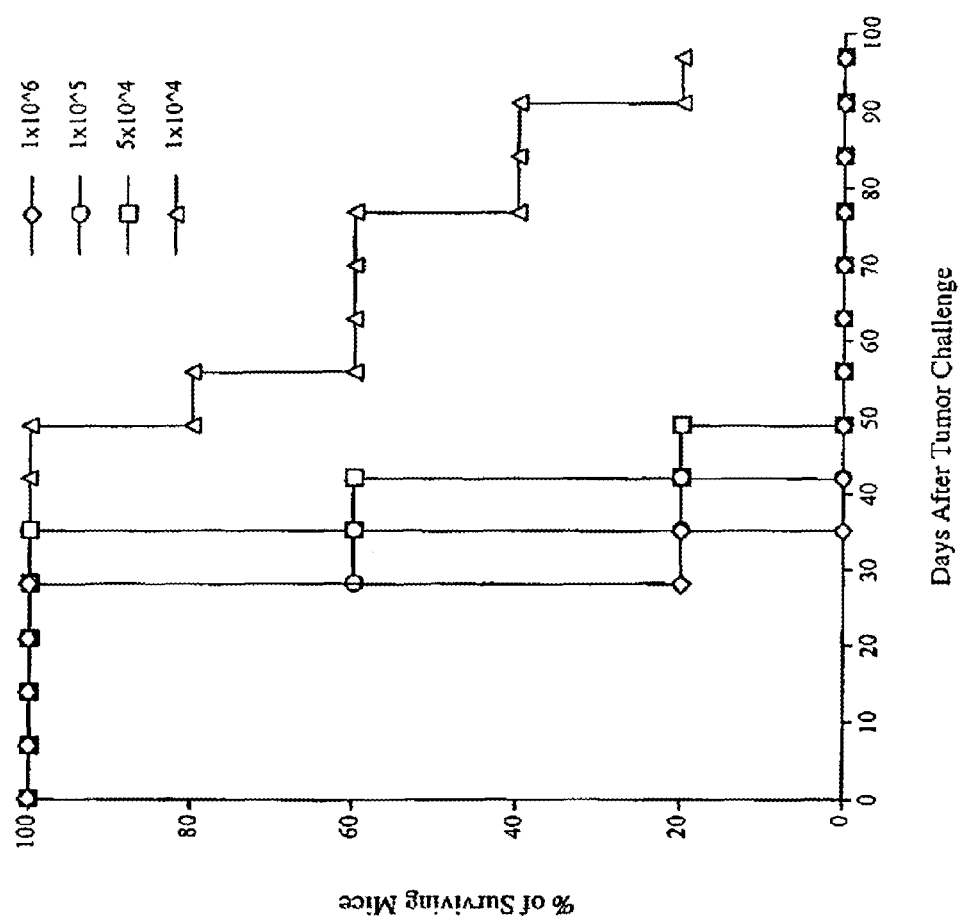

As shown in FIG. 9A, all of the mice injected with 5×104, 1×105, and 1×106 cells intraperitoneally formed ascites within 30 days. Meanwhile, 20% of mice injected with 1×104/mouse were tumor-free and without ascites formation 90 days after tumor challenge. All of the mice injected with a dose of 5×104 tumor cells or greater died within 50 days of tumor challenge (FIG. 9B). These data suggest that WF-3 tumor cells are able to lead to formation of ascites and solid tumors in the peritoneum of mice and eventually kill the injected mice at a certain tumor challenge dose.

Example 9

Mesothelin is Highly Expressed in the WF-3 Preclinical Ovarian Cancer Model. We have performed microarray analysis (Incyte Genomics Corporation, Palo Alto, Calif.) to characterize the gene expression profile of WF-3 compared to pre-WF0. The pre-WF0 cell line was generated by immortalizing mouse primary peritoneal cells with a retroviral vector carrying HPV-16 E6 and E7 genes using a previously described method (Lin, et al., (1996) Cancer Research, 56:21-26). We have chosen pre-WF0 as a reference cell line in order to identify genes in WF-3 that are relevant to tumorigenicity in later stages of ovarian cancer. Table 4 (below) summarizes highly expressed genes present in WF-3 relative to pre-WF0. As shown in Table 4, below, mesothelin is among the top 10 up-regulated genes in WF-3, suggesting that WF-3 may be a suitable preclinical model for developing mesothelin-specific cancer immunotherapy against ovarian cancer.

TABLE 4

Summary of Specifically Expressed Genes in WF-3

| Marker/Antigen | Sequence Accession # | Balanced differential expression |
|---|---|---|
| EGF-containing fibulin-like extracellular matrix protein 1 | AI156278 | 6.5 |
| Mesothelin | AA673869 | 3.8 |
| alpha-2-HS-glycoprotein | AI386037 | 3.3 |
| Protein kinase, cGMP-dependent, type II | AA771678 | 3.2 |
| sema domain, immunoglobulin domain (Ig), short basic domain, secreted (semaphorin) 3E | AA241390 | 3.2 |
| Ankyrin-like repeat protein | AA792499 | 2.8 |
| RIKEN cDNA 1300019103 gene | AA600596 | 2.6 |
| Matrix gamma-carboxyglutamate (gla) protein | W88093 | 2.4 |
| serine (or cysteine) proteinase inhibitor, clade F (alpha-2 antiplasmin, pigment epithelium Derived factor), member 1 | AA727967 | 2.3 |
| RIKEN cDNA1200011C15 gene | AA608330 | 2.2 |

Example 10

Expression of Mesothelin mRNA and Protein in WF-3 Tumor Cells. We further confirmed the expression of mesothelin by the WF-3 cell line using RT-PCR.

RNA was extracted from WF-3 tumor cells using RNAzol (Gibco BRL, Gaithersburg, Md.) according to the manufacturer's instructions. RNA concentration was measured and 1 mg of total cellular RNA was reverse transcribed in a 20 ml volume using oligo(dT) as a primer and Superscript reverse transcriptase (Gibco BRL). One ml of cDNA was amplified by the PCR using a set of primers (5'-CCCGAATTCATGGCCTTGCCAACAGCTCGA-3' and 5'-TATGGATCCGCTCAGCCTTAAAGCTGGGAG-3'; SEQ ID NOS: 11 and 12, respectively). The primer was derived from the published murine mesothelin cDNA sequence (Kojima, et al., (1995) J Biol Chem, 270:21984-21990). PCR was performed in a 50 ml reaction mixture with 250 mM of each dNTP, 100 nM of primers, 5 ml of 10× buffer (New England Biolabs, Berverly, Mass.), and 1 U of Vent DNA polymerase (New England Biolabs) using 30 cycles (94° C., 1-min denaturation; 55° C., 1-min annealing; and 72° C., 2-min extension). The reaction mixture (10 ml samples) was analyzed using agarose gel electrophoresis (1%) in TAE buffer containing 0.2 mg/ml ethidium bromide.

Figure 10:
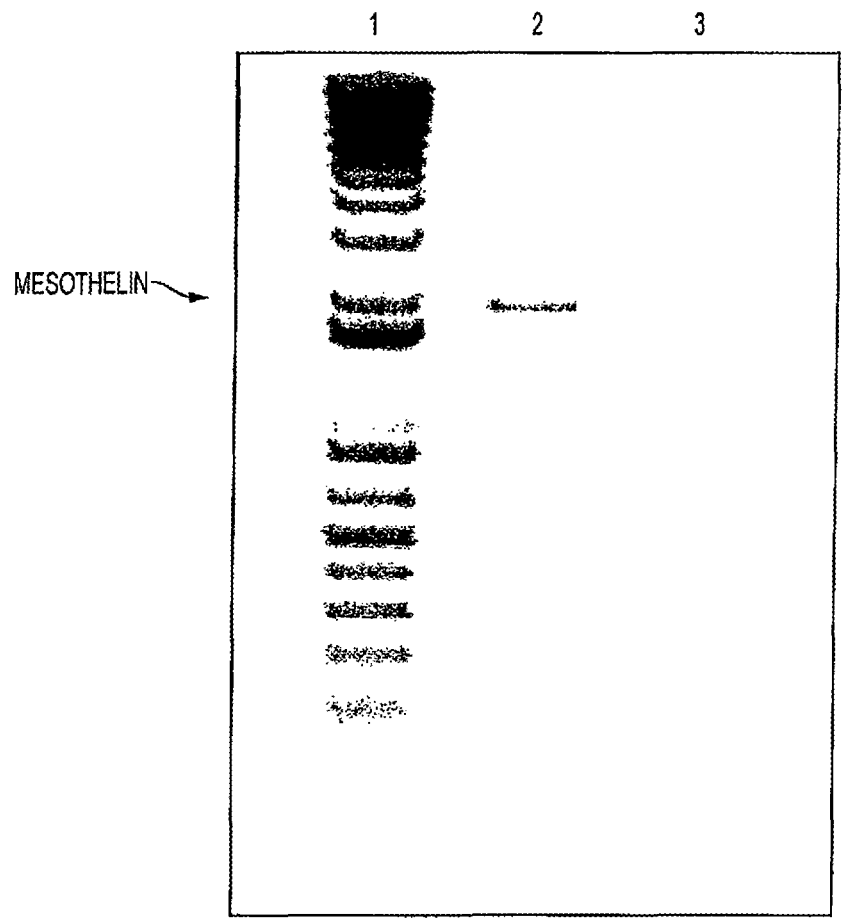
FIG. 10 shows expression of murine mesothelin in WF-3 tumor cells demonstrated by RT-PCR with gel electrophoresis.

Murine mesothelin protein shares about 65% similarity with human mesothelin protein. As shown in FIG. 10, we were able to detect mRNA expression of murine mesothelin in WF-3 tumor by RT-PCR (lane 2) but not in the control, B-16 tumor cells (lane 3). Western blot analysis was performed to determine expression of mesothelin protein in WF-3 tumor cells. Tumor cells were stained with anti-mesothelin mouse polyclonal antibodies. Results of the Western blot analysis confirmed that WF-3 was positive for mesothelin protein while B16 melanoma cells were mesothelin-negative (data not shown). Thus, our results indicate that WF-3 cells express mesothelin mRNA and protein.

FIG. 10 shows expression of murine mesothelin in WF-3 tumor cells as demonstrated by RT-PCR with gel electrophoresis. Western blot analysis was also performed to confirm expression (not shown). As shown in FIG. 10, RT-PCR was performed using the Superscript One-Step RT-PCR Kit (Gibco, BRL) and a set of primers: 5'-CCCGAATTCATGGCCTTGCCAACAGCTCGA-3' and 5'-TATGGATCCGCTCA GCCTTAAAGCTGGGAG-3' (SEQ ID NOS: 11 and 12, respectively). Western blot analysis was also used to demonstrate the expression of mesothelin protein in WF-3 tumor cells. Tumor cells were stained with anti-mesothelin mouse polyclonal antibody followed by FITC-conjugated goat anti-mouse IgG secondary antibody (data not shown).

Example 11

Mesothelin DNA Cancer Vaccine Immunotherapy. Using the peritoneal tumor model described above we demonstrated the ability of a DNA vaccine encoding mesothelin to generate mesothelin-specific cytotoxic T lymphocyte responses and antitumor effects greater than empty plasmid DNA. These data indicate that a DNA tumor vaccine targeting mesothelin can be used in treating or controlling ovarian carcinomas and other cancers in which mesothelin is highly expressed.

Plasmid DNA Construction. With the availability of the mesothelin-expressing tumor cell line, WF-3, we created DNA vaccines encoding mesothelin to test their antitumor effect against WF-3 in C57BL/6 mice. We used a mammalian cell expression vector, pcDNA3, to generate a DNA vaccine encoding murine full-length mesothelin protein (total length: 625 aa).

For construction of pcDNA3-mesothelin, a DNA fragment encoding mesothelin was first amplified from WF-3 extracted RNA and a set of primers (5'-CCCGAATTCATGGCCTTGCCAACAGCTCGA-3' and 5'-TATGGATCCGCTCAGCCTTAAAGCTGGGAG-3'; SEQ ID NOS: 11 and 12, respectively) by RT-PCR using the Superscript One-Step RT-PCR Kit (Gibco, BRL) and cloned into the EcoRI/BamHI sites of pcDNA3. The primer was derived from the published murine mesothelin cDNA sequence (11). The accuracy of DNA constructs was confirmed by DNA sequencing.

Vaccination with a DNA Vaccine Encoding Mesothelin Protein Protects Against Challenge with Mesothelin-Expressing Ovarian Tumors. We tested the ability of this pcDNA3-mesothelin DNA vaccine to protect against tumor challenge with WF-3 cells. Preparation of DNA-Coated Gold Particles and Gene Gun Particle-Mediated DNA vaccination using a helium-driven gene gun (Bio-rad, Hercules, Calif.) was performed according to a previously described protocol (Chen, et al., (2000) Cancer Research, 60: 1035-1042. DNA-coated gold particles (1 mg DNA/bullet) were delivered to the shaved abdominal region of C57BL/6 mice using a helium-driven gene gun (Bio-rad, Hercules, Calif.) with a discharge pressure of 400 p.s.i.

For the tumor protection experiment, mice (ten per group) were vaccinated intradermally with 2 mg of pcDNA3-mesothelin DNA. One week later, mice received a booster with the same dose. Mice were challenged one week after booster with a lethal injection of $5 \times 10^4$ WF-3 tumor cells intraperitoneally. Mice were monitored for evidence of ascites formation by palpation and inspection twice a week; the mice were sacrificed at day 90. The percentage of ascites-free mice in each vaccination group was determined.

Figure 11:
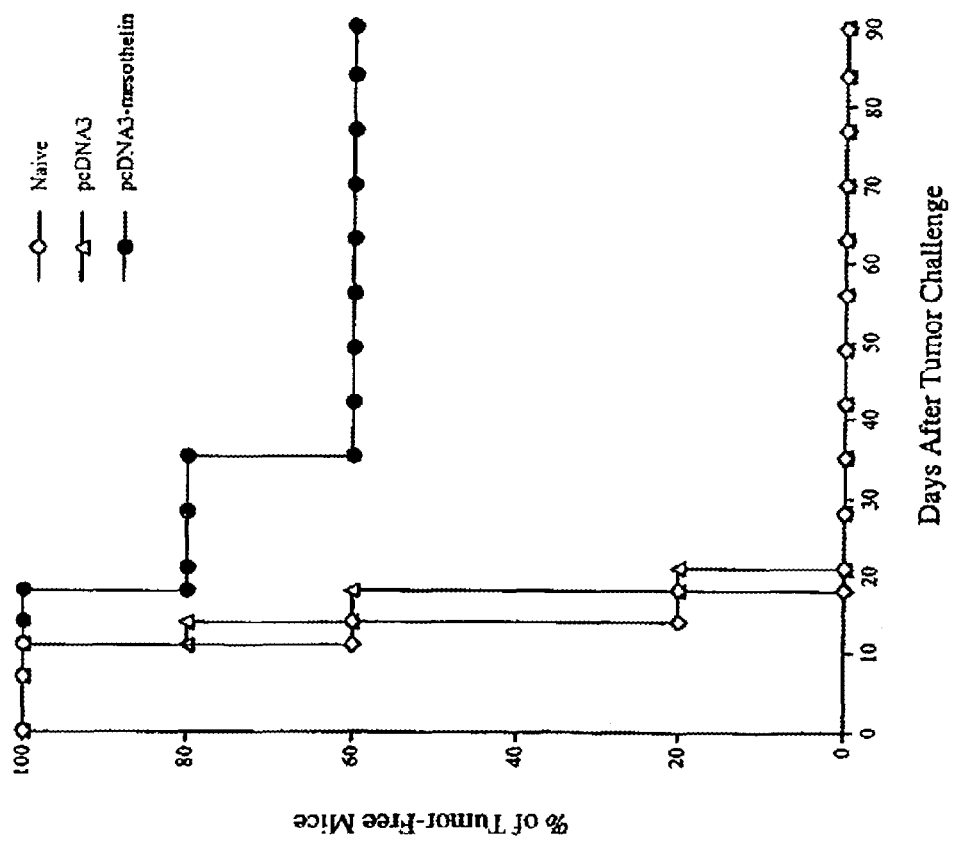
FIG. 11 shows in vivo tumor protection experiments against WF-3 tumor growth using mesothelin-specific DNA vaccines. Mice received a booster with the same dose one week later, followed by intraperitoneal challenge with $5\times10^4$ WF-3 cells/mouse one week afterward. Ascites, formation in mice was monitored by palpation and inspection. Mice were, sacrificed at day 90. Note: Vaccination with pcDNA3-mesothelin DNA resulted in a significantly higher percentage of tumor-free mice than vaccination with other DNA. (P<0.00 1). Results shown here are from one representative experiment of two performed.

Our data indicated that pcDNA3-mesothelin generated a high degree of protection (60%) against WF-3 tumor challenge. Controls were vaccinated with pcDNA3 vector alone (0%) or were not vaccinated (0%). FIG. 11 shows in vivo tumor protection experiments against WF-3 tumor growth using mesothelin-specific DNA vaccines.

Example 12

Vaccination with pcDNA3-mesothelin Generate Mesothelin-Specific Cytotoxic Immune Responses. CD8+ T lymphocytes are important effector cells for mediating antitumor immunity. Cytotoxic T lymphocyte (CTL) assays were performed to determine the cytotoxic effect of mesothelin-specific CD8+ T cells generated by the pcDNA3-mesothelin DNA vaccine. Splenocytes from vaccinated mice served as effector cells after being cultured with cell lysates containing mesothelin protein. WF-3 tumor cells served as target cells.

Generation of Mesothelin-Containing Cell Lysates from Transfected 293 Db,Kb Cells. To generate mesothelin containing cell lysates to pulse splenocytes for the CTL assays, a total of 20 mg of pcDNA3-mesothelin or empty plasmid DNA was transfected into $5 \times 10^6$ Db,Kb cells with lipofectamine 2000 (Life Technologies) according to the manufacturer's protocol. The transfected 293 Db,Kb cells were collected 40-44 h after transfection, then treated with three cycles of freeze-thaw. The protein concentration was determined using the Bio-Rad protein assay (Bio-Rad, Hercules, Calif.) according to vendor's protocol. Cell lysates containing mesothelin were used to pulse splenocytes obtained from the various vaccinated mice as described below.

Cytotoxic T Lymphocyte (CTL) Assays. Cytolysis was determined by quantitative measurements of lactate dehydrogenase (LDH) using CytoTox96 non-radioactive cytotoxicity assay kits (Promega, Madison, Wis.) according to the manufacturer's protocol. Briefly, splenocytes were harvested from vaccinated mice (5 per group) and pooled 1 week after the last vaccination. Splenocytes were pulsed with 20 mg of cell lysates in a total volume of 2 ml of RPMI 1640, supplemented with 10% (vol/vol) fetal bovine serum, 50 units/ml penicillin/streptomycin, 2 mM L-glutamine, 1 mM sodium pyruvate, 2 mM nonessential amino acids in a 24-well tissue culture plate for 6 days as effector cells. WF-3 tumor cells were used as target cells. WF-3 cells were mixed with splenocytes at various effector/target (E:T) ratios. After 5 hr incubation at 370 C., 50 µl of the cultured media were collected to assess the amount of LDH in the cultured media according to the manufacturer's protocol. The percentage of lysis was calculated from the following equation: $100 \times (A-B)/(C-D)$, where A is the reading of experimental-effector signal value, B is the effector spontaneous background signal value, C is maximum signal value from target cells, D is the target spontaneous background signal value.

Statistical Analysis. Statistical determinations were made using the Student's t-test. Two-sided values are presented in all experiments, and significance was defined as P<0.05. No mice were excluded from statistical evaluations.

Figure 12:
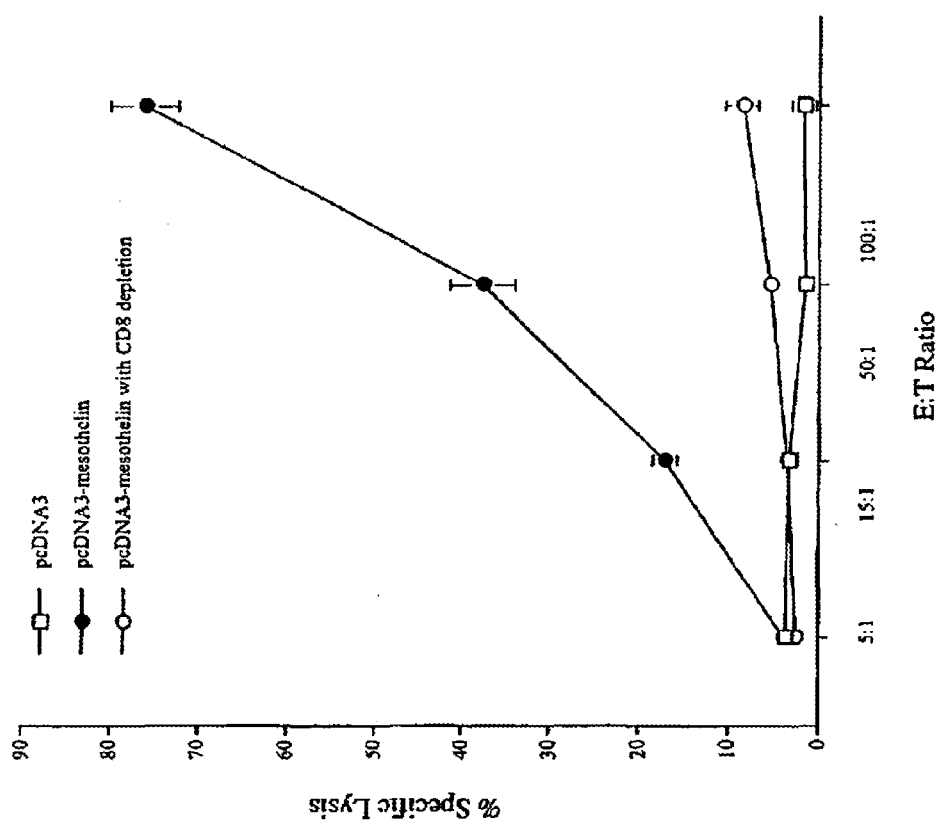
FIG. 12 shows CTL assays which demonstrate specific lysis induced by vaccination with mesothelin-specific DNA vaccines. Mice (5 per group) were immunized with various DNA vaccines intradermally. Mice received a booster with the same dose one week later. Splenocytes from mice were pooled 14 days after vaccination. To perform the cytotoxicity assay, splenocytes were cultured with mesothelin protein-for 6 days and used as effector cells. WF-3 tumor cells served as target cells. WF-3 cells were mixed with splenocytes at various E:T ratios. Cytolysis was determined by quantitative measurements of LDH. Note: The pcDNA3-mesothelin DNA vaccine generated a significantly higher percentage of specific lysis than the other DNA vaccines (P<0.001). The data presented in this figure are from one representative experiment of two performed.

As shown in FIG. 12, vaccination with pcDNA3-mesothelin generated a significant percentage of specific lysis compared to vaccination with pcDNA3 or no vaccination (P<0.001, one-way ANOVA). These results indicate that vaccination with pcDNA3-mesothelin DNA is capable of generating mesothelin-specific T cell-mediated specific lysis of WF-3.

Cytotoxic T Lymphocyte (CTL) assays which demonstrate specific lysis induced by vaccination with mesothelin-specific DNA vaccines. Mice (5 per group) were immunized with various DNA vaccines intradermally. Mice received a booster with the same dose one week later. Splenocytes from mice were pooled 14 days after vaccination. To perform the cytotoxicity assay, splenocytes were cultured with mesothelin protein for 6 days and used as effector cells. WF-3 tumor cells served as target cells. WF-3 cells were mixed with splenocytes at various E:T ratios. Cytolysis was determined by quantitative measurements of LDH. Note: The pcDNA3-mesothelin DNA vaccine generated a significantly higher percentage of specific lysis than the other DNA vaccines (P<0.001). The data presented in this figure are from one representative experiment of two performed.

Example 13

In this example, we utilize an attenuated strain of *Salmonella typhimurium* as a vehicle for oral genetic immunization. PcDNA3.1/myc-His(−) vectors expressing a myc-tagged version of mesothelin were constructed. Following immunization with the recombinant *S. typhimurium* aroA strain harboring the mesothelin expression vector, we are able to detect high levels of expression of the mesothelin/myc fusion protein using an anti-myc antibody by immunoassay. The *S. typhimurium* auxotrophic aroA strain SL7202 *S. typhimurium* 2337-65 derivative hisG46, DEL407 [aroA::Tn10(Tc-s)]), is used as carrier for these in vivo studies (see Darji et al. (1997) Cell 91: 761-775; Darji et al. (2000) FEMS Immunology and Medical Microbiology 27: 341-9). This *S. typhimurium*-based mesothelin DNA vaccine delivery system is then used to test whether this vaccine can protect ovarian cancer cells challenge using our WF-3 tumor model system.

References For Examples 5-13

1. Condon, C. et al., DNA-based immunization by in vivo transfection of, dendritic cells. Nat Med, 2: 1122-1128, 1996.
2. Ji, H., et al., Targeting BPV-16 E7 to the endosomal-lysosomal compartment enhances the antitumor immunity of DNA vaccines against murine HPV-16 E7-expressing tumors. Human Gene Therapy, 10: 2727-2740, 1999.
3. Chen, C. H., Ji, H., Suh, K. W., Choti, M. A., Pardoll, D. M., and Wu, T. C. Gene gun-mediated DNA vaccination induces antitumor immunity against human papillornavirus type 16 E7-expressing uterine tumor-metastases in the liver and lungs. Gene Ther, 6: 1972-1981, 1999.
4. Chen, C.-H., Suh, K. W., Ji, H., Choti, M. A., Pardoll, D. M., and Wu, T.-C Antigen-specific immunotherapy for HPV-16 E7-expressing tumors grown in liver. J. Hepatology, 33(1):91-8, 2000.
5. Chen, C.-H., Wang, T.-L., Hung, C.-F., Yang, Y., Young, R. A., Pardoll, D. M., and Wu, T.-C. Enhancement of DNA vaccine potency by linkage of antigen gene to an HSP70 gene. Cancer Research, 60: 1035-1042, 2000.
6. Hung, C.-F., Cheng, W.-F., Hsu, K.-F., Chai, C.-Y., He, L., Ling, M., and Wu, T.-C. Cancer immunotherapy using a DNA vaccine encoding the translocation domain of a bacterial toxin linked to a tumor antigen. Cancer Research, 61: 3698-3703, 2001.
7. Hung, C.-F., Cheng, W.-F., Chai, C.-Y., Hsu, K.-F., He, L., Ling, M., and Wu, T.-C. Improving vaccine potency through intercellular spreading and enhanced NMC class I presentation of antigen. J Immunol, 166: 5733-5740., 2001.
8. Hung, C.-F., Hsu, K.-F., Cheng, W.-F., Chai, C.-Y., He, L., Ling, M., and Wu, T.-C. Enhancement of DNA vaccine potency by linkage of antigen gene to a gene encoding the extracellular domain of F1t3-ligand. Cancer Research, 61: 1080-1088, 2001.
9. Cheng, W. F., Hung, C. F., Chai, C. Y., Hsu, K. F., He, L., Ling, M., and Wu, T. C. Tumor-specific immunity and antiangiogenesis generated by a DNA vaccine encoding calreticulin linked to a tumor antigen. J Clin Invest, 108: 669-678, 2001.
10. Halbert, C. L., Demers, G. W., and Galloway, D. A. The E7 gene of human papillomavirus type 16 is sufficient for immortalization of human epithelial cells. J Virol, 65:473-478, 1991.
11. Kojima, T., Oh-eda, M., Hattori, K., Taniguchi, Y., Tamura, M., Ochi, N., Yamaguchi, N. Molecular cloning and expression of megakaryocyte potentiating factor cDNA. J Biol Chem, 270: 21984-21990, 1995.
12. Lin, K.-Y., Guarnieri, F. G., Staveley-OCarroll, K. F., Levitsky, H. I., August, T., Pardoll, D. M., and Wu, T.-C. Treatment of established tumors with a novel vaccine that enhances major histocompatibility class II presentation of tumor antigen. Cancer Research, 56: 21-26, 1996.
13. Yokoyama, Y., Dhanabal, M., Griffloen, A. W., Sukhatme, V. P., and Ramakrishnan, S. Synergy between angiostatin and endostatin: inhibition of ovarian cancer growth. Cancer Res, 60: 2190-2196, 2000.
14. Huang, S., Robinson, 1. B., Deguan, A., Bucana, C. D., and Fidler, I. J. Blockade of nuclear factor-kappaβ signaling inhibits angiogenesis and tumorigenicity of human ovarian cancer cells by suppressing expression of vascular endothelial growth factor and interleukin 8 Cancer Res, 60: 5334 5339, 2000
15. Nielsen, L. L., Shi, B., Hajian, G., Yaremko, B., Lipari, P., Ferrari, E., Gurnani, M., Malkowski, M., Chen, J., Bishop, W. R., and Liu, M. Combination therapy with the farnesyl protein transferase inhibitor SCH66336 and SCH58500 (p53 adenovirus) in preclinical cancer models. Cancer Res, 59: 5896-5901., 1999.
16. Mesiano, S., Ferrara, N., and Jaffe, R. B. Role of vascular endothelial growth factor in ovarian cancer inhibition of ascites formation by immunoneutralization. Am J Pathol, 153: 1249-1256., 1998.
17. Elliott G. and O'Hare, P. Intercellular trafficking and protein delivery by a herpesvirus structural protein. Cell, 88: 223-233, 1997.
18. Rosenberg, S. A. A new era for cancer immunotherapy based on the genes that encodecancer antigens. Immunity, 10: 281-287., 1999.
19. Boon, T., Cerottini, J. C., Van den Eynde, B., van der Bruggen, P., and Van Pel, A. Tumor antigens recognized by T lymphocytes Annu Rev Immunol, 12: 337-365, 1994.
20. Schena, M., Shalon, D, Davis, R. W., and Brown, P. O. Quantitative monitoring of gene expression patterns with a complementary DNA microarray. Science, 270: 467-470, 1995.
21. Velculescu, V. E., Zhang, L., Vogelstein, B., and Kinzler, K. W. Serial analysis of gene expression. Science, 270: 484-487., 1995.
22. Lander, E. S., et al., Initial sequencing and analysis of the human genome. Nature, 409: 860-921, 2001.
23. Chen, Y. T., Scanlan, M. J., Sahin, U., Tureci, O., Gure, A. O, Tsang, S., Williamson, B., Stockert, E., Pfreundschuh, M., and Old, L. J. A testicular antigen aberrantly expressed in human cancers detected by autologous antibody screening. Proc Natl Acad Sci USA, 94: 1914-1918., 1997.
24. Tureci, O., Sahin, U., Schobert, I., Koslowski, M., Scmitt, H., Schild, H. J., Stenner, F., Seitz, G., Ranunensee, H. G., and Pfreundschuh, M. The SSX-2 gene, which is involved in the t(X; 18) translocation of synovial sarcomas, codes for the human tumor antigen HOM-MEL-40. Cancer Res, 56: 4766 4772, 1996.

Example 15

Materials and Methods (for Examples 16-25)
Mice
Female C57BL/6 and athymic nude mice were acquired from the National Cancer Institute. All animals were maintained under specific pathogen-free conditions, and all procedures were performed according to approved protocols and in accordance with recommendations for the proper use and care of laboratory animals.
Cell Lines
A syngeneic mouse ovarian epithelial cancer cell line ID8 transfected with VEGF-A and β-defensin 29 (named Defb29 Vegf) was a generous gift from Dr. Coukos.[34] Defb29 Vegf-luciferase (Defb29 Vegf-luc) were generated by transducing Defb29 Vegf cells with the retrovirus containing luciferase pLuci-thy1.1 and flow cytometry sorting following the protocol described previously.[18] For stable expression of human mesothelin on this cell line, Defb29 Vegf-luc was further transduced with retrovirus containing full-length mesothelin cDNA and isolated as described previously.[35] Growth rate of Defb29 Vegf-luc/Hmeso cells was comparable to those of Defb29 Vegf-luc cells (data not shown). Luciferase and GFP-expressing OVCAR3 (OVCAR3-luc/GFP) was generated by transduction with a lentivirus containing luciferase and GFP. Lentiviral vector pCDH1-luc-EF1-GFP was transfected into Phoenix packaging cell line using lipofectamine (Invitrogen, Carlsbad, Calif.) and the virion-containing supernatant was collected 48 h after transfection. The supernatant was then filtered through a 0.45-mm cellulose acetate syringe filter (Nalgene, Rochester, N.Y.) and used to infect OVCAR3 cells in the presence of 8 mg/mL Polybrene (Sigma, St. Louis, Mo.). Transduced cells were isolated using preparative flow cytometry with GFP signal.
Plasmid DNA Constructs and DNA Preparation
The generation of pcDNA3-Hmeso has been described previously.[35] A lentiviral construct pCDH-Luc-EF1-GFP (System Biosciences, Mountain View, Calif.) expressing both luciferase and GFP was made to transduce the OVCAR3 cells. Firefly luciferase was amplified by PCR from pGL3- basic (Promega, Madison, Wis.) and cloned into pCDF1-MCS2-EF1-copGFP (System Biosciences, Mountain View, Calif.). All the constructs were verified by restriction analysis and DNA sequencing using ABI 3730 DNA Analyzer by Johns Hopkins DNA analysis facility.

Tumor Treatment

Naïve C57BL6 (5 per group) mice were intra-peritoneally injected with $5×10^5$ Defb29 Vegf-Luc/Hmeso cells. After 3 days, mice were treated with 2 μg/mouse of pcDNA3-Hmeso or empty vector (pcDNA/myc-His) DNA vaccine through gene gun 3 times at one-week interval. Tumor load in DNA treated mice was evaluated by luminescence activity once per week for eight weeks using IVIS 200 bioluminescent imaging system (Xenogen, Cranbury, N.J.).

C57BL6 mice (5 per group) were vaccinated with 2 μg/mouse of empty vector (group 1) or pcDNA3-Hmeso DNA (groups 2-5) by gene gun two times at one a week-interval. Of them, groups 3-5 mice vaccinated with pcDNA3-Hmeso were injected intraperitoneally (i.p.) with blocking antibody using a protocol similar to one described previously.[36] Mice were injected with 100 μg/mouse of purified rat monoclonal antibody GK1.5 (anti-CD4, group 3), mAb 2.43 (anti-CD8, group 4), or mAb PK136 (anti-NK1.1, group 5). Depletion was started one week after mesothelin DNA vaccination and continued every other day for one week and every week onwards. All these five groups of mice were then challenged intra-peritoneally with $1×10^6$/mouse of Defb29 Vegf-luc/Hmeso cells two weeks after the last vaccination. Depletion was maintained by continuing the antibody injections weekly for the duration of the tumor imaging follow-up. Differences in the luminescence activity of tumor growth were monitored once a week.

Antibody Binding and Flow Cytometry Analysis

Blood was obtained from C57BL/6 mice (5 per group) vaccinated with 2 μg/mouse of pcDNA-Hmeso DNA vaccine three times at one-week intervals one week after the last vaccination. The presence of human mesothelin-specific antibodies was characterized by staining the Defb29 Vegf-luc, Defb29 Vegf-luc/Hmeso, and human OVCAR3 ovarian cancer cells using serum from pcDNA3-Hmeso DNA vaccinated mice in a 1/200 dilution, followed by Phycoerythrin (PE)-conjugated anti-mouse IgG antibody (eBioscience, San Diego, Calif.) staining Serum from naïve mice was used as control. Analysis of cell staining was performed on a Becton-Dickinson FACScan with CELLQuest software (Becton Dickinson Immunocytometry System, Mountain View, Calif.).

Adoptive Serum Transfer Experiment in C57BL/6 and Athymic Nude Mice

Serum containing human mesothelin-specific antibodies was prepared from C57BL6 mice immunized with 2 μg/mouse pcDNA-Hmeso three times in one-week interval. One week after last vaccination, serum obtained from these immunized mice or naïve mice (control) were collected for adoptive therapy. C57BL/6 mice were challenged with $5×10^5$/mouse of Defb29 Vegf-luc/Hmeso cells, and followed by IVIS bioluminescent imaging on D3 to confirm equal amount of growing tumor in each mouse. Tumor challenged mice (5 per group) were subjected to adopted therapy with intraperitoneal injection of serum from mesothelin immunized mice or naïve mice (100 μl/mouse every three days for four times). Athymic nude mice were injected with $2×10^5$/per mouse of Defb29 Vegf-luc/Hmeso cells or OVCAR3-luc/GFP cells. Treatments with serum from immunized or naïve mice were commenced after confirmation of equal amount of tumor growth on D5 (for mice challenged with Defb29 Vegf-luc/Hmeso tumor cells) and D3 (for mice challenged with OVCAR3-luc/GFP tumor cells). These mice were followed for their tumor growth by IVIS bioluminescent imaging every week and also for their survival.

Complement Dependent Toxicity Assay

Target cells Defb29 Vegf-luc/Hmeso were seeded in 96-well plate ($1×10^4$/well). Sera collected from mice immunized with human mesothelin (pcDNA-Hmeso) or non-immunized mice were added into the well in the following amounts: 10 μl, 1 μl, and 0 μl and followed by a naïve rabbit serum in a final dilution 1:5 dilution used for complement (Sigma-Aldrich, St Louis, Mo.) with culture medium in total volume of 100 μl.[37] Defb29 Vegf-luc cells were used as a negative control. After incubation for 6 hours, cell viability was measured as bioluminescent activity by IVIS Imaging System.

Statistical Analysis

All data expressed as means±standard deviation (SD) are representative of at least two different experiments. Comparisons between individual data points were made using a Student's t-test. Differences in survival between experimental groups were analyzed using the Kaplan-Meier approach. The statistical significance of group differences will be assessed using the log-rank test.

Example 16

Intraperitoneal tumors such as ovarian cancer, malignant mesothelioma and pancreatic cancer represent serious diseases in humans. Ovarian cancer is the sixth most common malignancy in women and the leading cause of death from all gynecological cancers in the United States. 1 Malignant mesothelioma is rarely noticed at its early stages and therefore, little is known of the establishment and progression of the disease (for review, see 2,3). Pancreatic carcinoma is the fourth leading cause of cancer-associated deaths in the United States. 4 Current therapies such as surgery, chemotherapy and radiotherapy usually fail to control advanced stages of these diseases. Therefore, alternative approaches such as immunotherapy may serve as an important method to control these intraperitoneal tumors.

Antigen-specific immunotherapy is an attractive approach for the treatment of cancers since it has the potency to specifically eradicate systemic tumors and control metastases without damaging normal cells. The immune system has multiple collaborative effector mechanisms capable of killing target cells through two major response pathways: T-cell mediated immunity and the humoral response. T cells can generate tumor-specific immune responses by recognizing tumor-specific antigens (as peptide fragments) via a vast array of clonally distributed antigen receptors. Thus, identification of tumor-associated antigens expressed uniquely in intraperitoneal tumors is important for the development of antigen-specific cancer immunotherapy. B cells can also elicit a tumor-specific humoral response when activated by helper T cells to produce immunoglobulin G antibodies specific to antigens. The antibodies will then respond by neutralization, opsonization or complement activation.

DNA vaccines have emerged as a potentially potent antigen-specific immunotherapy since they have the ability to activate both T-cell mediated responses and humoral responses. Furthermore, DNA vaccines are a favorable form of vaccine for the control of infectious diseases and cancers since they offer many advantages over conventional vaccines such as peptide or attenuated live pathogens (for review, see [5-8]). For instance, DNA vaccines can be administered time after time without adverse effects and are relatively safe. In addition, DNA vaccines are comparatively easy to produce on a large scale and are able to yield products with high purity and stability. Most importantly, effective DNA vaccine delivery systems, such as direct intradermal administration of DNA vaccines via gene gun to professional antigen presenting cells (APCs), have been well established. Using this delivery method, we have previously developed several innovative strategies to enhance DNA vaccine potency by modifying the properties of DNA-transfected APCs (for reviews, see [9,10]).

DNA vaccines targeting mesothelin as a tumor-antigen may serve as an important form of vaccine against mesothelin-expressing intraperitoneal tumors such as ovarian cancer, mesothelioma, and pancreatic adenocarcinoma. Mesothelin has been found to be highly overexpressed in these intraperitoneal tumors.[11-15] Furthermore, it is absent or present in low levels in normal tissues and other types of cancer.[11] In addition, it has been suggested that mesothelin is a highly immunogenic protein in cancers with high mesothelin-expression. For example, Ho, et al. showed that a high percentage of anti-mesothelin antibodies was found in ovarian cancer and mesothelioma patient sera and was associated with high expression of the antigen in tumors.[16] In comparison, antibodies to mesothelin were found in only 4% of pharynx and larynx squamous cell carcinoma patients in a study done by Suaraez-Alverez, et al.[17] Therefore, mesothelin represents a potentially ideal target antigen for the development of cancer immunotherapy using DNA vaccines against mesothelin-expressing tumors.

In the current study, we have generated a murine ovarian cancer cell line, Defb29 Vegf-luc/Hmeso that expresses human mesothelin. We found that treatment of mice challenged with Defb29 Vegf-luc/Hmeso tumor cells with mesothelin DNA vaccine inhibits tumor growth and promotes survival. We have shown that protective anti-tumor effect generated by the mesothelin DNA vaccine is dependent in part on CD8+ and CD4+ lymphocytes. Furthermore, we found that serum obtained from mesothelin DNA immunized mice can kill tumor cells in vitro through rabbit complement and binds to mesothelin-expressing cancer cells. We also found that serum from mesothelin DNA immunized mice produces an anti-tumor effect and leads to long-term survival in both immunocompetent and immunocompromised mice using adoptive serum transfer experiments. Therefore, employment of DNA vaccine encoding human mesothelin in addition to the anti-human mesothelin antibody containing serum obtained from vaccinating mice with mesothelin DNA vaccine serves as a potentially potent antigen-specific cancer immunotherapy.

Example 17

Figure 13:
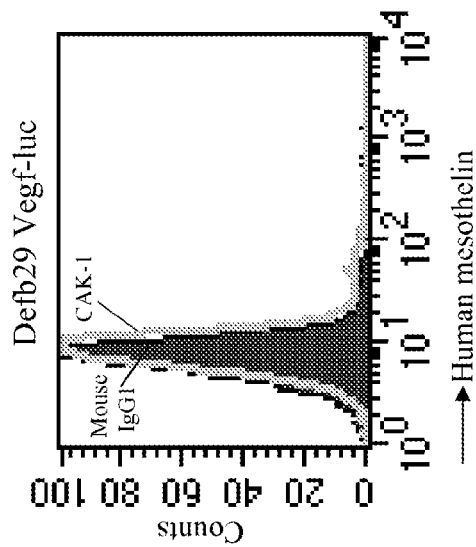
FIG. 13: Flow cytometry analysis to characterize the expression of human mesothelin in Defb29 Vegf-luc/Hmeso cell line. Characterization of human mesothelin expression was performed in Defb29 Vegf-luc/Hmeso and Defb29 Vegf-luc cells using flow cytometry analysis. The cell lines were stained with the human mesothelin-specific mouse monoclonal antibody CAK-1, followed by flow cytometry analysis. Mouse IgG1 isotype was used as a control.
Figure 13:
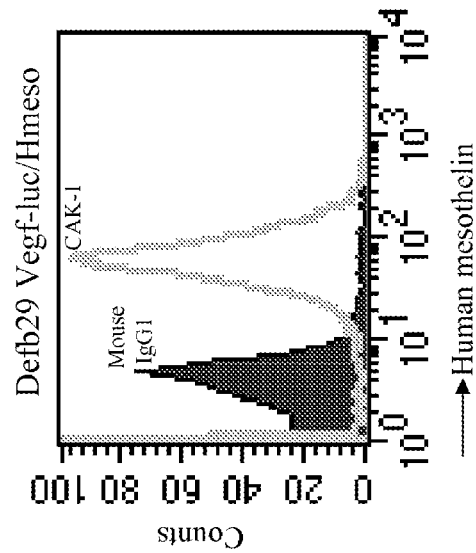

Murine ovarian cancer cells transfected with DNA encoding human mesothelin led to expression of human mesothelin. We generated a human mesothelin-expressing ovarian cancer cell line by transducing Defb29 Vegf-luc cells[18] with retrovirus encoding full-length human mesothelin (Defb29 Vegf-luc/Hmeso). To characterize the human mesothelin (Hmeso) expression of the transduced cells, we performed flow cytometry analysis using human mesothelin-specific mouse monoclonal antibody, CAK-1. As shown in FIG. 13, Defb29 Vegf-luc/Hmeso cells expressed human mesothelin (left panel). In comparison, Defb29 Vegf-luc cells without transduction showed no expression of human mesothelin (right panel). Thus our data indicate that transduction of Defb29 Vegf-luc cells with retrovirus encoding human mesothelin leads to expression of human mesothelin.

Example 18

Figures 14A, 14B, 14C:
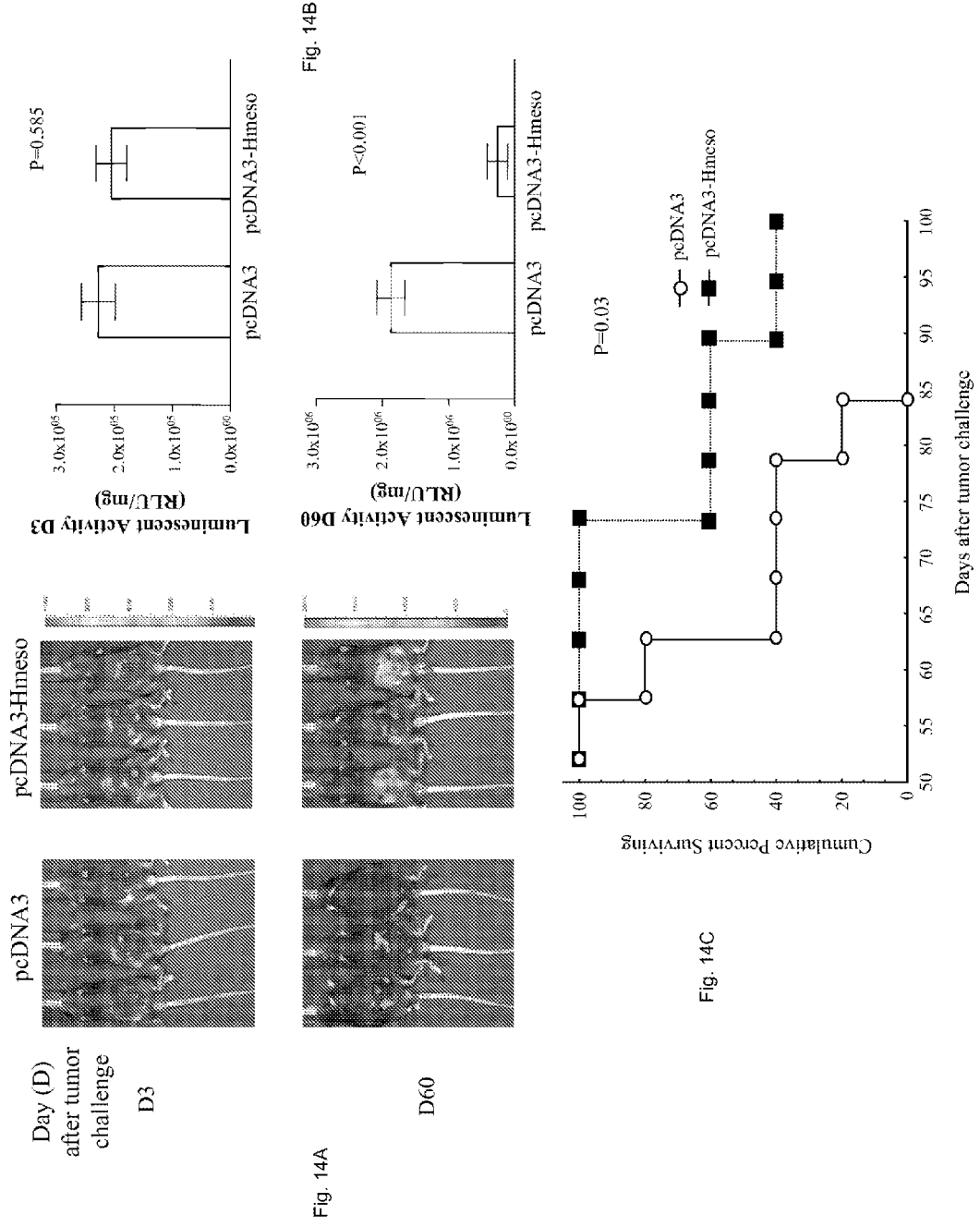
FIGS. 14A-14C: Characterization of anti-tumor effects generated by treatment with human mesothelin expressing DNA vaccine. C57BL/6 mice (5 per group) were challenged with $5\times10^5$/mouse of Defb29 Vegf-luc/Hmeso cells (day 0). Three days after tumor challenge, mice with established Defb29 Vegf-luc/Hmeso tumors were treated with DNA vaccine encoding human mesothelin (pcDNA3-Hmeso) via gene gun. An empty vector vaccine (pcDNA3) was used as a control. Mice were imaged using the IVIS Imaging System Series 200. Bioluminescence signals were acquired for one minute.

Treatment with pcDNA3-Hmeso DNA vaccine inhibits tumor growth and promotes survival in mice challenged with Defb29 Vegf-luc/Hmeso tumor cells. To characterize the therapeutic effects of treatment with Hmeso DNA vaccine, we first challenged C57BL/6 mice with $5 \times 10^5$/mouse of Defb29 Vegf-luc/Hmeso cells. Three days later, tumor challenged mice were treated with empty vector DNA (pcDNA3) or human-mesothelin DNA (pcDNA3-Hmeso) vaccines. Tumor growth in challenged mice was then monitored using bioluminescent imaging systems. As shown in FIG. 14A, we observed a significant reduction in luciferase activity in Defb29 Vegf-luc/Hmeso tumor-bearing mice treated with pcDNA3-Hmeso compared to tumor challenged mice treated with pcDNA3 (*p=0.585). A graphical representation of the luminescent activity data is depicted in FIG. 14B. We also characterized the survival of the treated mice using the Kaplan & Meier survival analysis. As shown in FIG. 14C, prolonged survival was observed in tumor challenged mice treated with pcDNA3-Hmeso compared to mice treated with pcDNA3 (*p<0.001). Thus, our data indicate that treatment with pcDNA3-Hmeso DNA leads to significant anti-tumor effects and prolonged survival in mice bearing mesothelin-expressing Defb29 Vegf-luc/Hmeso tumors.

Example 19

Figures 15A, 15B:
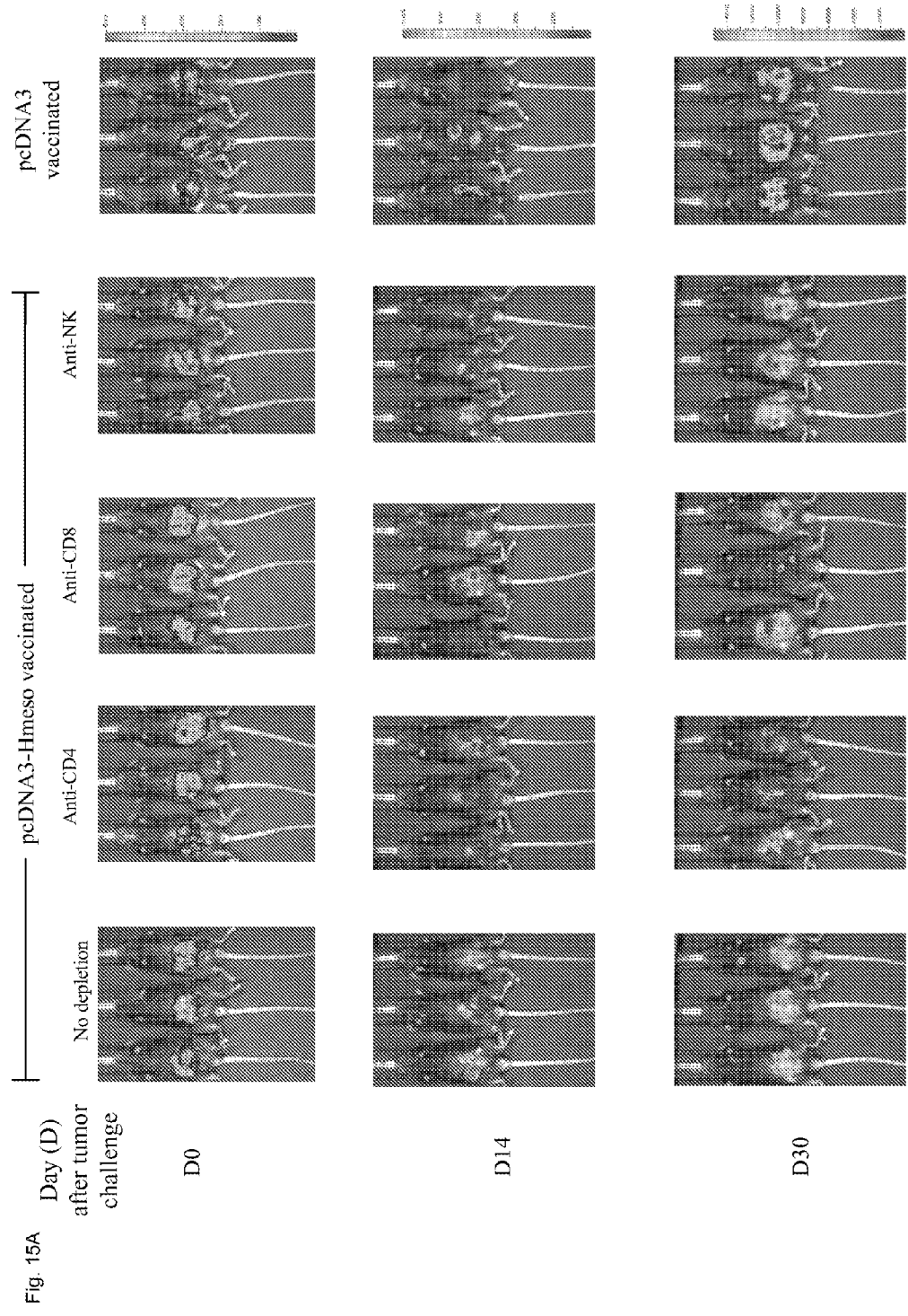
FIGS. 15A-15B: In vivo antibody depletion experiment. C57BL/6 mice (5 per group) were intraperitoneally immunized with pcDNA3-Hmeso twice at a one-week interval via gene gun. One week after the last vaccination, the pcDNA3-Hmeso vaccinated mice were depleted of either CD8, CD4 or NK cells using relevant antibodies every other day for one week and then once every week, as described in the Materials and Methods section. A group of non-depleted pcDNA3-Hmeso vaccinated mice was used as a control. Two weeks after vaccination, depleted and non-depleted mice were challenged with $1\times10^6$/mouse of Defb29 Vegf-luc/Hmeso tumor cells (day 0). Mice were imaged using the IVIS Imaging System Series 200. Bioluminescence signals were acquired for one minute. pcDNA3 vaccinated mice challenged with Defb29 Vegf-luc/Hmeso cells were used as a control.
Figure 15B:
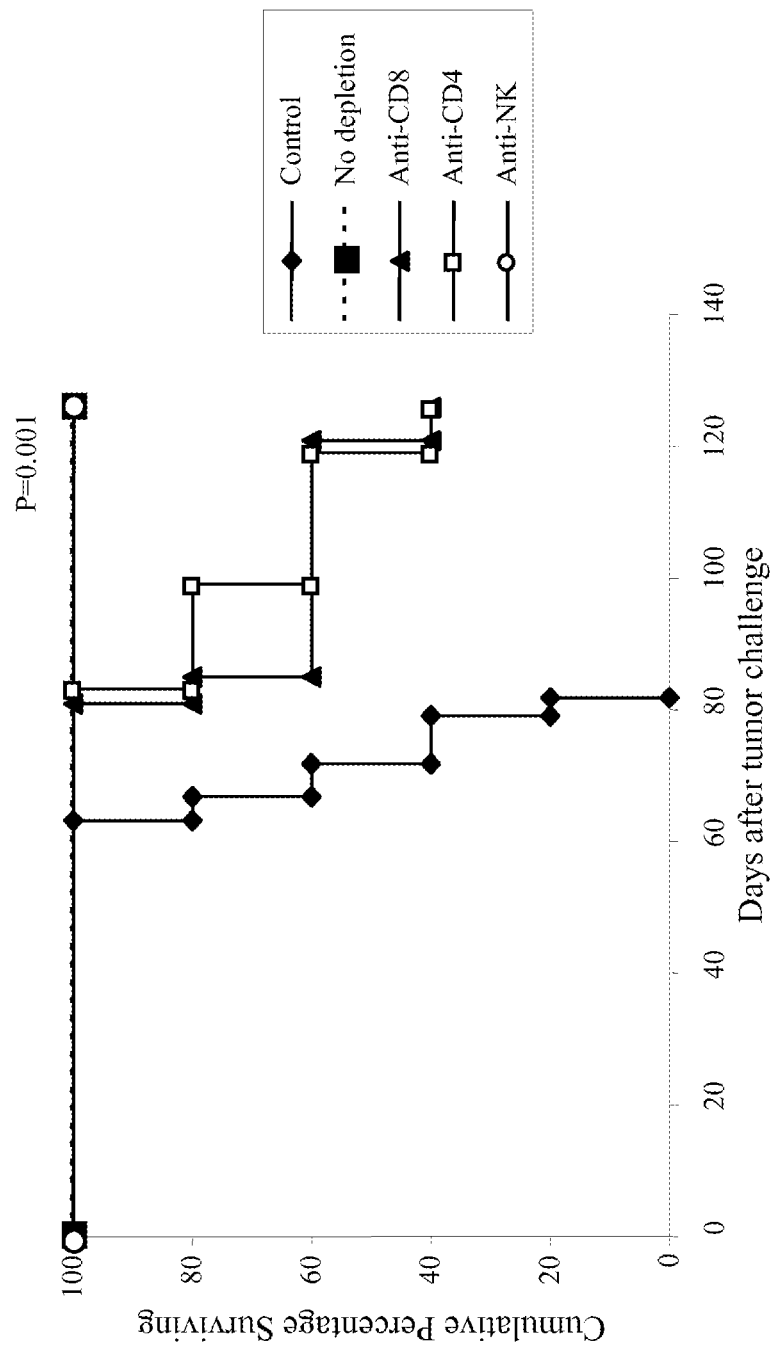

CD8+ and CD4+ T lymphocytes are important for the protective anti-tumor effects generated by pcDNA3-Hmeso DNA vaccine. To determine the subset of lymphocytes that are important for the anti-tumor effect, we performed in vivo depletion experiments using monoclonal antibodies specific for CD4+ T cells, CD8+ T cells or NK cells. C57BL/6 mice were immunized with the pcDNA3-Hmeso DNA vaccine. One week after vaccination, depletion was initiated of pcDNA3-Hmeso immunized groups. Depletion occurred every other day for one week and then once a week through follow-up imaging. Two weeks after the last vaccination, all mice were challenged with Defb29 Vegf-luc/Hmeso tumor cells. Another group of C57BL/6 mice were vaccinated with pcDNA3 as a tumor growth control. Tumor growth was monitored using bioluminescent imaging systems. As shown in FIG. 15A, we observed a significant decrease in luciferase activity in pcDNA3-Hmeso vaccinated mice compared to pcDNA3 vaccinated mice, indicating preventive anti-tumor effects of pcDNA3-Hmeso DNA vaccination (*p=0.05). In addition, a significant increase in luciferase activity was observed in pcDNA3-Hmeso vaccinated mice depleted of CD8+ or CD4+ T cells compared to pcDNA3-Hmeso vaccinated mice without depletion or with NK depletion. Furthermore, as shown in FIG. 15B, prolonged survival was observed in 100% of the pcDNA3-Hmeso DNA vaccinated mice without lymphocyte depletion and with NK depletion as compared to only 40% of the pcDNA3-Hmeso DNA vaccinated mice depleted of CD8+ and CD4+ cells. Our data suggest that immunization of mice with pcDNA3-Hmeso leads to significant protective anti-tumor effect and prolonged survival in mice challenged with Defb29 Vegf-luc/Hmeso tumor cells. Furthermore, CD8+ T cells and CD4+ T cells but not NK cells contribute to the observed protective anti-tumor effects.

Example 20

Figure 16:
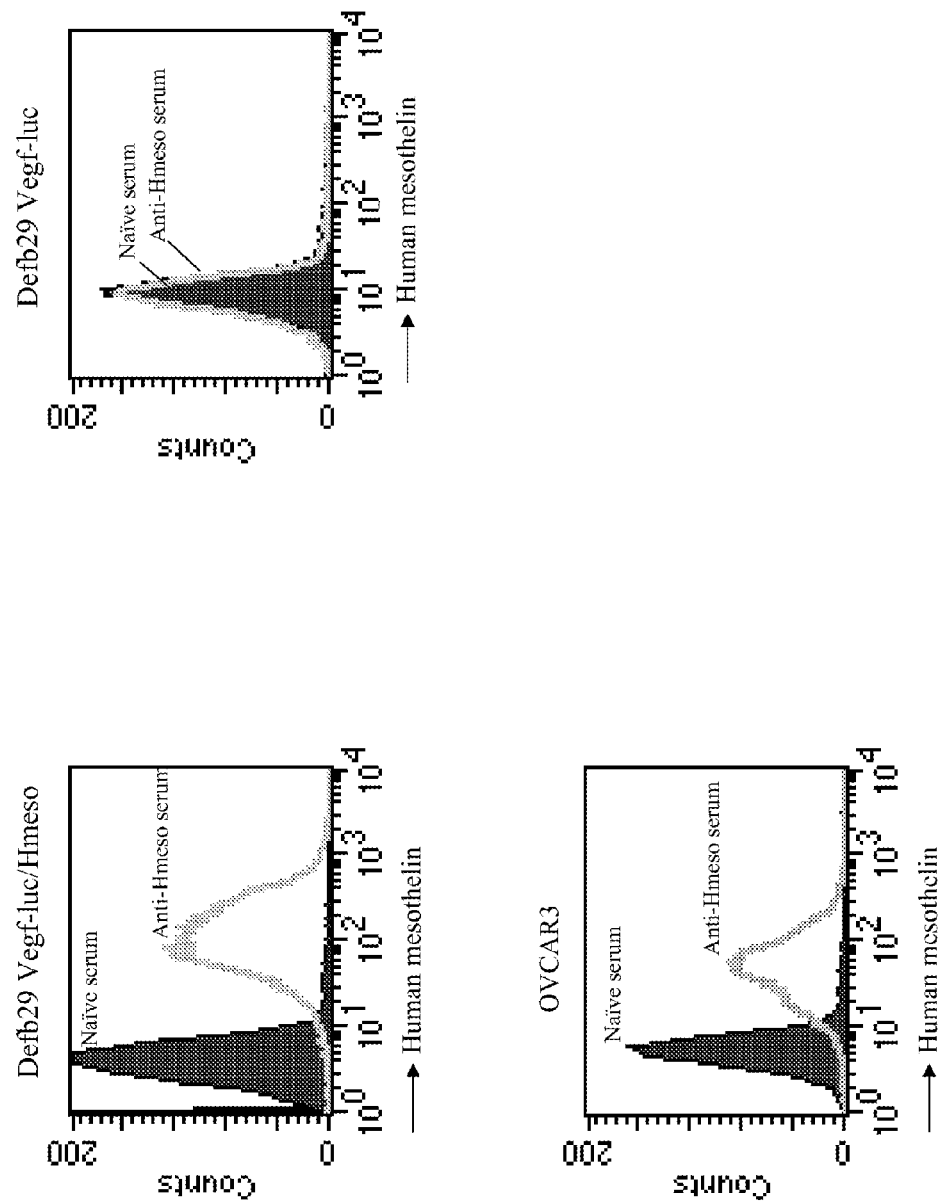
FIG. 16: Flow cytometry analysis to characterize the expression of human mesothelin in murine and human ovarian cancer cell lines. Human mesothelin-specific antibody containing serum was generated by immunization of C57BL/6 mice with pcDNA3-Hmeso DNA vaccine three times at one-week intervals via gene gun. One week after vaccination, blood sera were collected from immunized mice and used to stain murine and human cancer cell lines. The characterization of human mesothelin expression in Defb29 Vegf-luc/Hmeso, Defb29 Vegf-luc and OVCAR3 was performed with flow cytometry analysis using sera collected from pcDNA3-Hmeso immunized mice. Sera from naïve mice was used as a negative control.

Immunization of mice with pcDNA3-Hmeso elicits a strong human mesothelin-specific antibody responses. In order to characterize the antibody response in mice immunized with pcDNA3-Hmeso DNA vaccine, we performed flow cytometry analyses of mesothelin-expressing and non-mesothelin expressing cell lines using sera from vaccinated mice. Sera were collected from pcDNA3-Hmeso immunized C57BL/6 mice one week after the last immunization and used to stain the various ovarian cancer cell lines: Defb29 Vegf-luc/Hmeso (murine), Defb29 Vegf-luc (murine), and OVCAR3 (human). Sera from naïve C57BL/6 mice were used as a control. As shown in FIG. 16, Defb29 Vegf-luc/Hmeso and OVCAR3 cell lines, both known to express human-mesothelin, showed significant shifts of fluorescent signal. In comparison, no specific staining was observed in Defb 29 Vegf-luc cells, which were used as a negative control. Furthermore, no specific staining was observed when staining mesothelin-expressing cell lines with sera collected from naïve mice. These data suggest that immunization of C57BL/6 mice induces human mesothelin-specific antibody responses in vaccinated mice.

Example 21

Figures 17A, 17B:
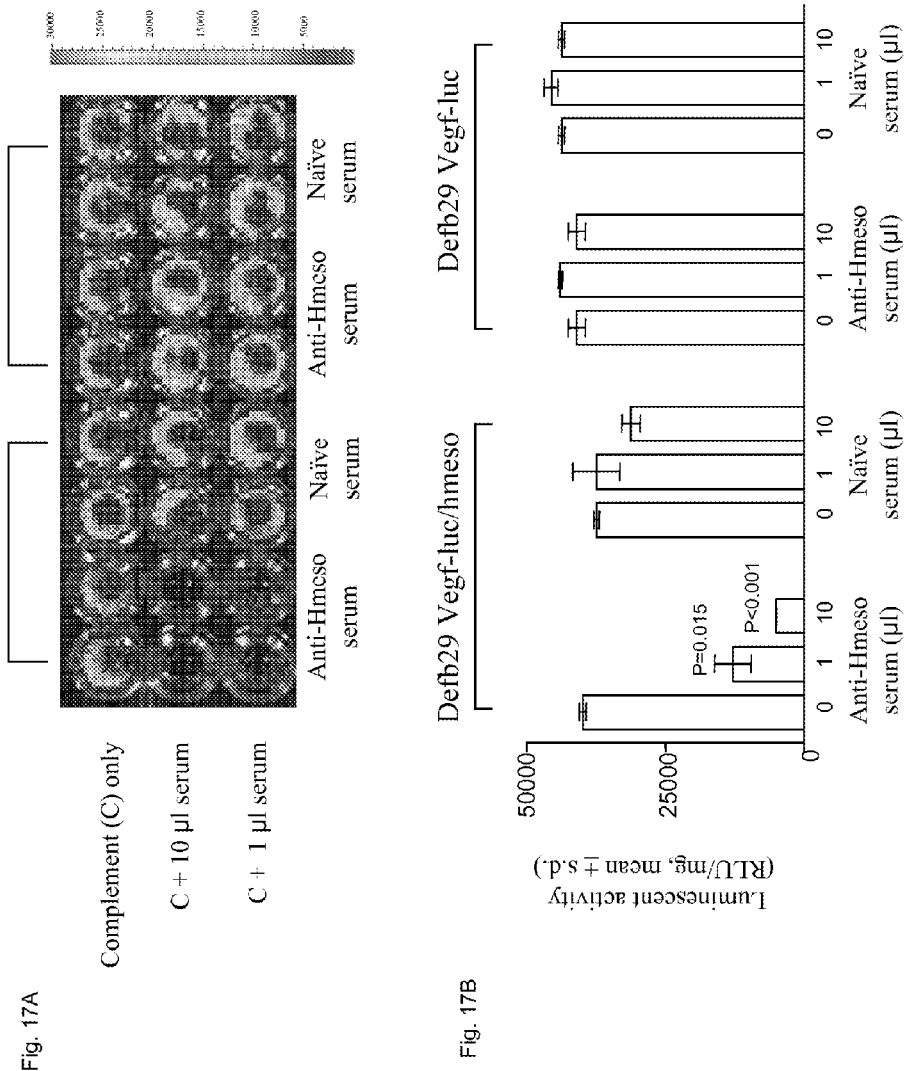
FIGS. 17A-17B: Complement dependent cytotoxicity assay using human mesothelin-specific antibodies from pcDNA3-Hmeso immunized mice. $1 \times 10^4$ Defb29 Vegf-luc/Hmeso cells were seeded in 96-well plate. Defb29 Vegf-luc cells were used as a negative control. Cell viability was determined after adding serum and complement using the IVIS Imaging System Series 200. Sera obtained from either pcDNA3-Hmeso immunized mice or naïve mice were added in amounts of 0, 1 and 10 μl/well to both cell lines. Rabbit sera (complement) was added to all wells at a 1:5 dilution. Bioluminescence signals were acquired for one minute.

Human mesothelin-specific antibodies from pcDNA3-Hmeso immunized mice cause complement-mediated lysis of Defb29 Vegf-luc/Hmeso cells in vitro. In order to determine whether the human mesothelin-specific antibodies present in sera collected from pcDNA3-Hmeso vaccinated mice can cause complement-mediated lysis of human mesothelin-expressing tumor cells in vitro, we performed complement dependent cytotoxicity experiments using Defb29 Vegf-luc/Hmeso or Defb Vegf-luc cell lines with rabbit sera for complement. As shown in FIG. 17A, tumor cell lysis was observed specifically in Defb29 Vegf-luc/Hmeso cells incubated with sera collected from pcDNA3-Hmeso vaccinated mice and complement but not with sera collected from naïve mice and complement, as indicated by reduced luciferase expression (P<0.02). No specific lysis was observed when Defb29 Vegf-luc was incubated with sera collected from pcDNA3-Hmeso vaccinated mice and complement or with sera collected from naïve mice with complement. The luciferase activity in the wells was quantified in the form of bar graphs (FIG. 17B). Our data indicate that human mesothelin specific antibodies in sera collected from pcDNA3-Hmeso immunized mice can cause lysis of human-mesothelin expressing tumor cells in the presence of complement in vitro.

Example 22

Figure 18:
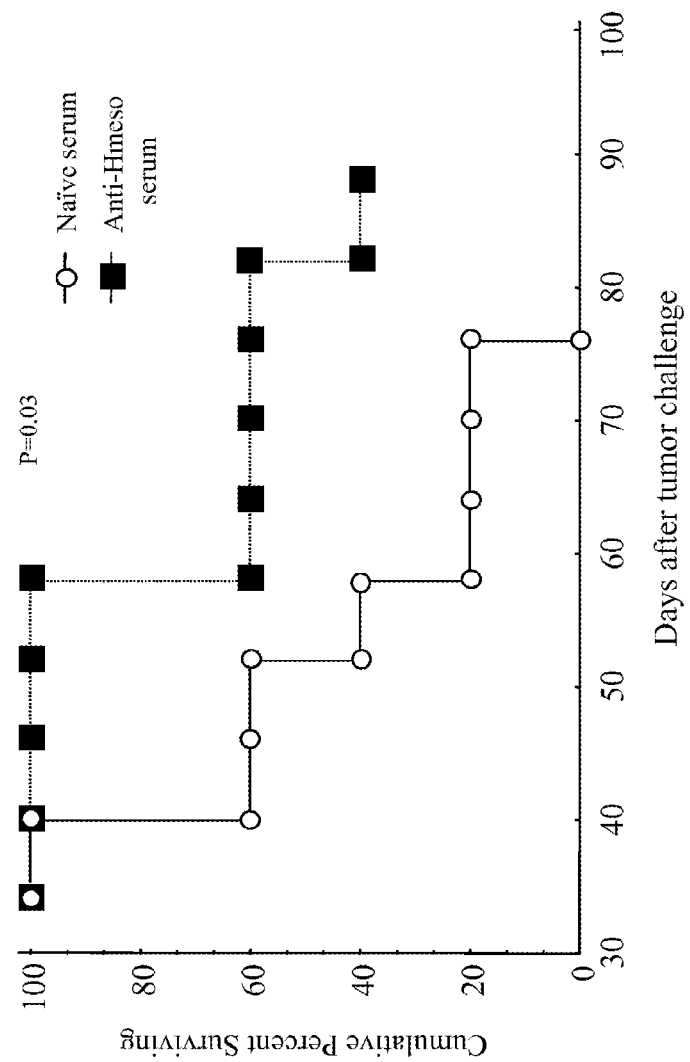
FIG. 18: Adoptive serum transfer experiments in tumor-bearing C57BL/6 mice. C57BL/6 mice (5 per group) were challenged with $5 \times 10^4$/mouse of Defb29 Vegf-luc/Hmeso cells. Five days later, the tumor-bearing mice were treated with sera from pcDNA3-Hmeso immunized mice or sera from naïve mice intraperitoneally every three days for four times. Kaplan & Meier survival analysis of the tumor-bearing mice was performed. The days indicated follow from day 0 of tumor challenge.

Adoptive transfer of human mesothelin-specific antibodies leads to long-term survival of Defb29 Vegf-luc/Hmeso tumor-bearing immunocompetent mice. In order to characterize the anti-tumor effects generated by human mesothelin-specific antibodies in serum from pcDNA3-Hmeso immunized mice in the absence of T cells, we performed serum transfer experiments using Defb29 Vegf-luc/Hmeso tumor-bearing athymic nude mice. In order to characterize the influence of sera derived from pcDNA3-Hmeso immunized mice on the survival of C57BL/6 mice challenged with Defb29 Vegf-luc/Hmeso cells, we performed serum transfer experiments using sera from immunized mice or naïve mice. Since treatment with pcDNA3 showed no anti-tumor effect, serum from pcDNA3-immunized mice would not be significantly different from serum from naïve mice. In fact, we have done the first experiment with naïve mice challenged with Defb29 Vegf-luc/Hmeso cells and found no difference in luciferase expression from challenged mice treated with pcDNA3 (data not shown). Therefore, we have used serum from naïve mice for the experiments involving treatment with serum. C57BL/6 mice with established Defb29 Vegf-luc/Hmeso tumors were intraperitoneally injected with sera collected from pcDNA3-Hmeso immunized mice or naïve mice. The survival of the tumor challenged mice was characterized using Kaplan & Meier survival analysis. As shown in FIG. 18, tumor challenged mice that received anti-Hmeso serum showed significantly better survival compared to the survival of challenged mice that received sera from naïve mice (*p=0.03). Thus, these data indicate that human mesothelin-specific antibodies in sera collected from pcDNA3-Hmeso immunized mice are able to control human mesothelin expressing murine ovarian tumors in immunocompetent mice.

Example 23

Figures 19A, 19B, 19C:
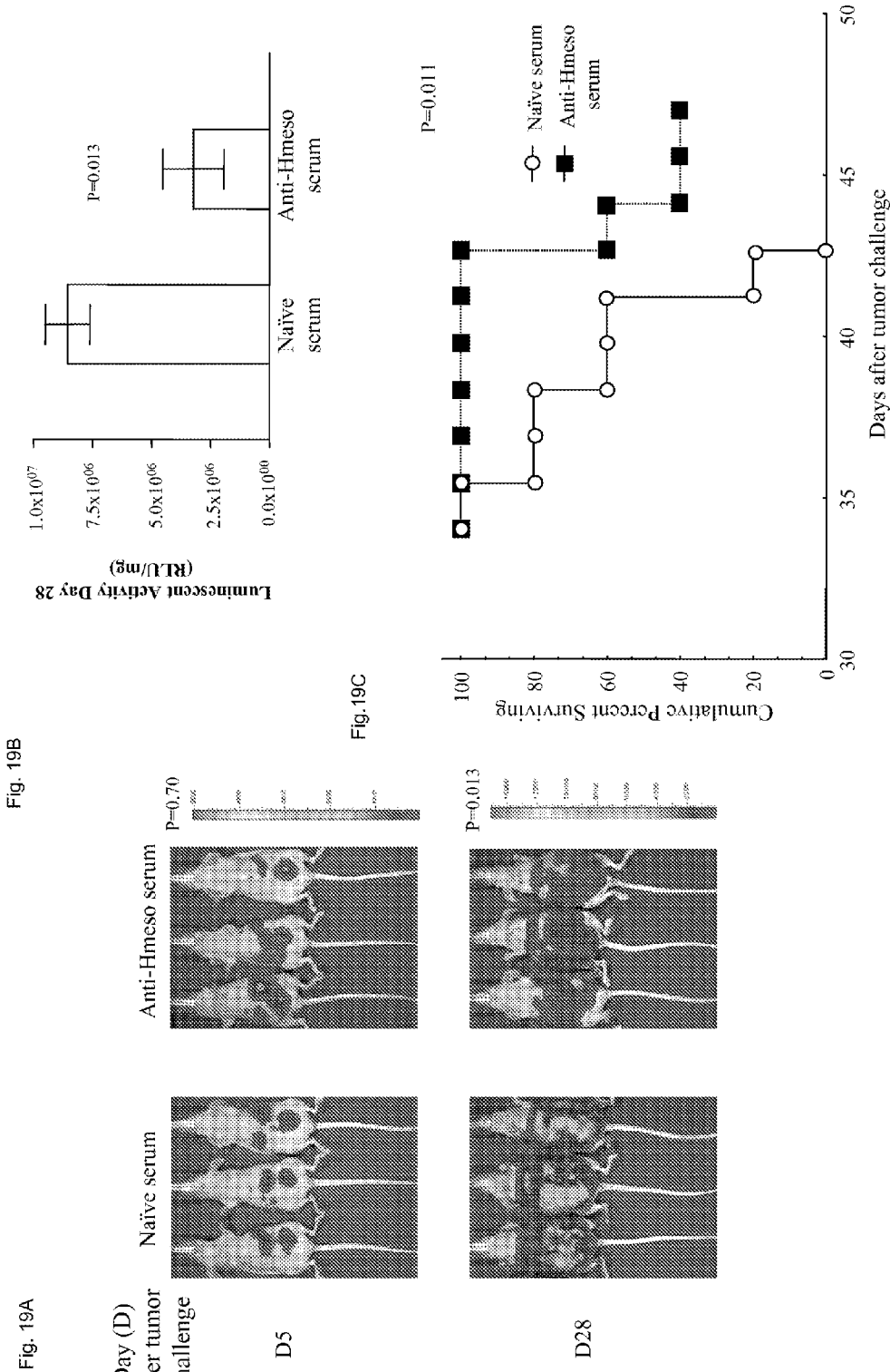
FIGS. 19A-19C: Serum transfer experiments in tumor-bearing immunocompromised mice. Athymic nude mice (5 per group) were challenged with $5 \times 10^4$/mouse of Defb29 Vegf-luc/Hmeso cells (day 0). Three days later, the tumor-bearing mice were treated with sera from pcDNA3-Hmeso immunized mice or sera from naïve mice intraperitoneally every three days for four times. Tumor load in treated mice was monitored using the IVIS Imaging System Series 200. Bioluminescence signals were acquired for one minute.

Adoptive transfer of human mesothelin-specific antibodies leads to long-term survival of Defb29 Vegf-luc/Hmeso tumor-bearing immunocompromised mice. In order to characterize the anti-tumor effects generated by human mesothelin-specific antibodies in sera from pcDNA3-Hmeso immunized mice in the absence of T cells, we performed serum transfer experiments using Defb29 Vegf-luc/Hmeso tumor-bearing athymic nude mice. Recipient athymic nude mice were subcutaneously challenged with $5 \times 10^4$/mouse of Defb29 Vegf-luc/Hmeso cells. Equal tumor growth among mice was confirmed by bioluminescence imaging. One week after tumor challenge, tumor-bearing mice were intraperitoneally injected with serum from pcDNA3-Hmeso immunized mice or naïve mice. Tumor growth among challenged mice was characterized by bioluminescence imaging. As shown in FIG. 19A, tumor-bearing mice treated with sera from pcDNA3-Hmeso immunized mice show significantly lower tumor volume over time than mice treated with sera from naïve mice, as indicated by lower luciferase activity (*p=0.013). A graphical representation of the tumor volume by quantification of luminescent activity is depicted in FIG. 19B. We further characterized the survival of tumor challenged mice following treatment with sera from pcDNA3-Hmeso immunized mice using Kaplan & Meier survival analysis. As shown in FIG. 19C, tumor-bearing mice that received sera from pcDNA3-Hmeso immunized mice showed significantly better long-term survival compared to tumor-bearing mice that received sera from naïve mice (*p=0.011). Thus, these data indicate that treatment with human-mesothelin specific antibody containing sera is capable of controlling human mesothelin-expressing murine ovarian tumors in the absence of T cells.

Example 24

Figures 20A, 20B:
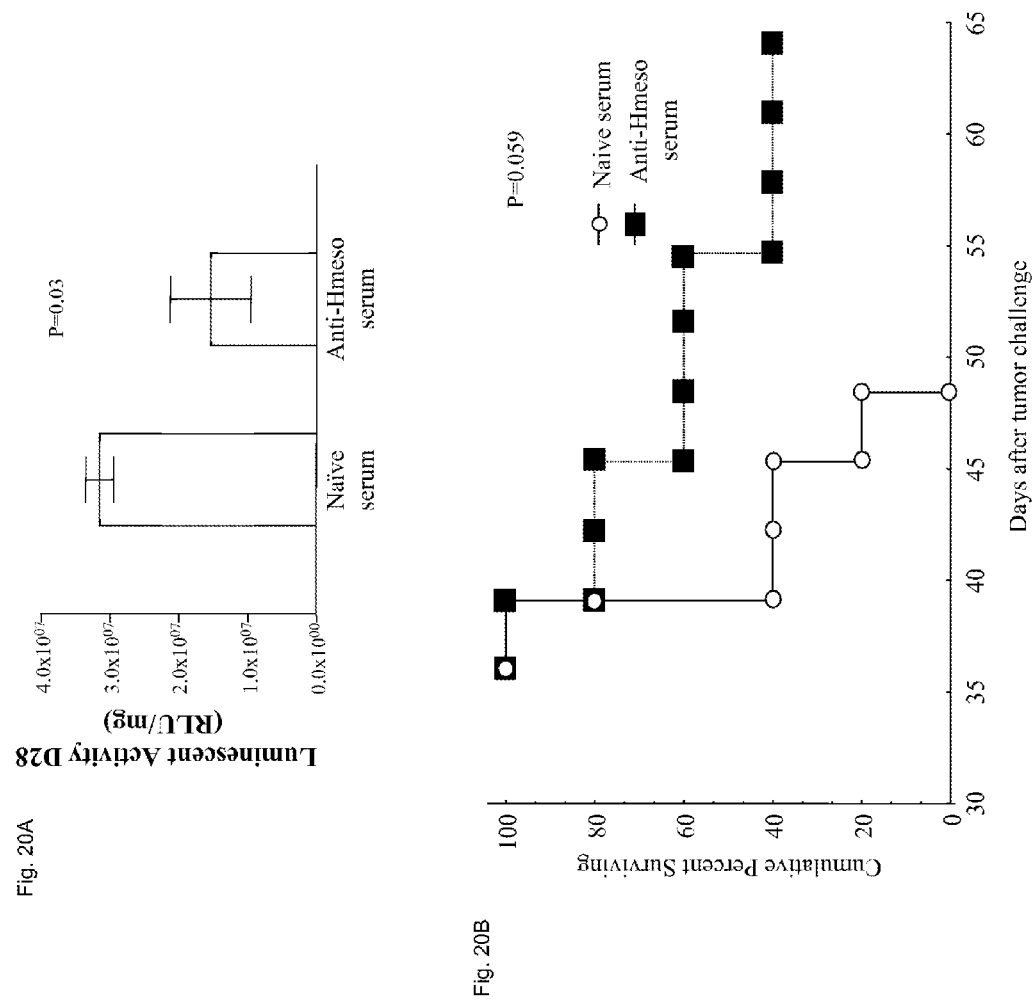
FIGS. 20A-20B: Serum transfer experiments in human ovarian cancer bearing immunocompromised mice. Athymic nude mice (5 per group) were challenged with $5 \times 10^4$/mouse of OVCAR3-luc/Hmeso cells (day 0). Three days later, the tumor-bearing mice were treated with sera from pcDNA3-Hmeso immunized mice or sera from naïve mice intraperitoneally every three days for four times. Tumor load in treated mice was monitored using the IVIS Imaging System Series 200. Bioluminescence signals were acquired for one minute.

Adoptive transfer of human mesothelin-specific antibodies leads to long-term survival of OVCAR3-luc/GFP tumor-bearing immunocompromised mice. In order to determine human mesothelin-specific antibodies in sera from pcDNA3-Hmeso immunized mice are capable of controlling mesothelin-expressing human ovarian cancer, we performed serum transfer experiments using OVCAR3-luc/GFP tumor-bearing athymic nude mice. Recipient athymic nude mice were subcutaneously challenged with $5 \times 10^4$/mouse of OVCAR3-luc/GFP cells. Equal tumor growth among mice was confirmed by bioluminescence imaging. One week after tumor challenge, OVCAR3-luc/GFP tumor-bearing mice were intraperitoneally injected with sera from pcDNA3-Hmeso immunized mice or naïve mice. As shown in FIG. 20A, OVCAR3-luc/GFP challenged mice treated with sera from pcDNA3-Hmeso immunized mice show significantly lower tumor volume over time than tumor-bearing mice treated with serum from naïve mice (*p=0.03). We further characterized the survival of tumor challenged mice treated with sera from pcDNA3-Hmeso immunized mice using Kaplan & Meier survival analysis. As shown in FIG. 20B, tumor challenged mice that received sera from pcDNA3-Hmeso immunized mice showed better survival compared to challenged mice that received sera from naïve mice, although the differences are not statistically significant (*p=0.059). Thus, these data indicate that treatment of OVCAR3-luc/GFP challenged athymic nude mice with anti-Hmeso serum induces therapeutic anti-tumor effects and borderline prolonged survival compared to treatment of challenged mice with naïve serum.

Example 25

As described in Examples 15-25, we created a murine ovarian cancer cell line that expressed human mesothelin for our DNA vaccine studies. We found that the Defb29 Vegf-luc/Hmeso tumor-bearing mice can be effectively controlled by treatment with human mesothelin DNA vaccine, pcDNA3-Hmeso. In addition, we found that both CD4$^+$ and CD8$^+$ T cells but not NK cells contribute to the anti-tumor effects generated by vaccination with pcDNA3-Hmeso DNA vaccine. Furthermore, we found that the human mesothelin-specific antibodies in sera collected from pcDNA3-Hmeso DNA immunized mice are capable of controlling human mesothelin-expressing murine and human ovarian cancer cell lines, resulting in prolonged survival of tumor-bearing mice. Our results serve as an important foundation for future clinical translation.

While our system demonstrated significant therapeutic effects against human mesothelin-expressing ovarian cancer with pcDNA3-Hmeso DNA vaccine, our system does not address the issue of tolerance. Human mesothelin is not normally expressed in the mouse, thus no tolerance against human mesothelin is expected in mice. In fact, we have also performed similar experiments using a DNA vaccine encoding murine mesothelin in C57BL/6 mice challenged with murine mesothelin-expressing mouse ovarian surface epithelial cancer (MOSEC) cells. Treatment of mice challenged with MOSEC tumor cells with the murine mesothelin DNA vaccine failed to control tumor growth (data not shown). Thus, in order to extend our study to future clinical translation, we need to consider innovative strategies that are capable of breaking tolerance against endogenous antigens. For example, the employment of xenogeneic antigens for the DNA vaccine development has been shown to effectively break tolerance in some cancer models.[19-28] Other strategies that are capable of breaking tolerance includes the employment of suicidal DNA vectors and bacterial vectors.[29-33] Thus, the use of tolerance breaking methods in conjunction with therapeutic strategies targeting human mesothelin may overcome this problem.

In the current study we observed that human mesothelin-specific antibodies in sera collected from mice immunized with pcDNA3-Hmeso have therapeutic effects against human mesothelin-expressing murine an ovarian tumors. The therapeutic effects translate into a better survival in tumor-bearing mice. Although the mechanism for the anti-tumor effects mediated by human mesothelin-specific antibodies remain unclear, our in vitro data suggest that complement mediated lysis may contribute to the anti-tumor effect (see FIG. 17). The encouraging results from this preclinical study suggests that the further development of mesothelin-specific antibody-based immunotherapy may represent a potentially plausible approach for the control of intraperitoneal mesothelin-expressing tumors. Currently, there is one early phase of clinical trials using humanized monoclonal antibodies against human mesothelin in patients with mesothelin-expressing pancreatic cancer (Dr. Elizabeth Jaffe, personal communication) and ovarian cancer (Dr. Deborah Armstrong, personal communication) at Johns Hopkins Hospital.

In summary, we have shown that DNA vaccine encoding human mesothelin is capable of generating therapeutic anti-tumor effects against human mesothelin-expressing tumors through both T-cell mediated and humoral-mediated immune responses. Further development of the DNA vaccine employing strategies that are capable of breaking tolerance to human mesothelin may lead to eventual clinical translation.

References For Examples 15 to 25

1 Greenlee R T, Murray T, Bolden S, Wingo P A. Cancer statistics, 2000. *CA Cancer J Clin* 2000; 50: 7-33.
2 Zellos L S, Sugarbaker D J. Multimodality treatment of diffuse malignant pleural mesothelioma. *Semin Oncol* 2002; 29: 41-50.
3 Nowak A K, Lake R A, Kindler H L, Robinson B W. New approaches for mesothelioma: biologics, vaccines, gene therapy, and other novel agents. *Semin Oncol* 2002; 29: 82-96.
4 Jhala N, Jhala D, Vickers S M, Eltoum I, Bata S K, Manne U et al. Biomarkers in Diagnosis of pancreatic carcinoma in fine-needle aspirates. *Am J Clin Pathol* 2006; 126: 572-579.
5 Shedlock D J, Weiner D B. DNA vaccination: antigen presentation and the induction of immunity. *J Leukoc Biol* 2000; 68: 793-806.
6 Pardoll D M, Beckerleg A M. Exposing the immunology of naked DNA vaccines. *Immunity* 1995; 3: 165-169.
7 Moniz M, Ling M, Hung C F, Wu T C. HPV DNA vaccines. *Front Biosci* 2003; 8: d55-68.
8 Donnelly J J, Ulmer J B, Shiver J W, Liu M A. DNA vaccines. *Annu Rev Immunol* 1997; 15: 617-648.
9 Hung C F, Wu T C. Improving DNA vaccine potency via modification of professional antigen presenting cells. *Curr Opin Mol Ther* 2003; 5: 20-24.
10 Boyd D, Hung C F, Wu T C. DNA vaccines for cancer. *IDrugs* 2003; 6: 1155-1164.
11 Scholler N, Fu N, Yang Y, Ye Z, Goodman G E, Hellstrom K E et al. Soluble member(s) of the mesothelin/megakaryocyte potentiating factor family are detectable in sera from patients with ovarian carcinoma. *Proc Natl Acad Sci USA* 1999; 96: 11531-11536.
12 Yen M J, Hsu C Y, Mao T L, Wu T C, Roden R, Wang T L et al. Diffuse mesothelin expression correlates with prolonged patient survival in ovarian serous carcinoma. *Clin Cancer Res* 2006; 12: 827-831.
13 Argani P, Iacobuzio-Donahue C, Ryu B, Rosty C, Goggins M, Wilentz R E et al. Mesothelin is overexpressed in the vast majority of ductal adenocarcinomas of the pancreas: identification of a new pancreatic cancer marker by serial analysis of gene expression (SAGE). *Clin Cancer Res* 2001; 7: 3862-3868.
14 Robinson B W, Creaney J, Lake R, Nowak A, Musk A W, de Klerk N et al. Mesothelin-family proteins and diagnosis of mesothelioma. *Lancet* 2003; 362: 1612-1616.
15 Hassan R, Bera T, Pastan I. Mesothelin: a new target for immunotherapy. *Clin Cancer Res* 2004; 10: 3937-3942.
16 Ho M, Hassan R, Zhang J, Wang Q C, Onda M, Bera T et al. Humoral immune response to mesothelin in mesothelioma and ovarian cancer patients. *Clin Cancer Res* 2005; 11: 3814-3820.

17 Suarez-Alvarez B, Garcia Suarez M M, Arguelles M E, Sampedro A, Alvarez Marcos C, Mira E et al. Circulating IgG response to stromelysin-3, collagenase-3, galectin-3 and mesothelin in patients with pharynx/larynx squamous cell carcinoma. *Anticancer Res* 2001; 21: 3677-3684.
18 Hung C F, Tsai Y C, He L, Coukos G, Fodor I, Qin L et al. Vaccinia virus preferentially infects and controls human and murine ovarian tumors in mice. *Gene Ther* 2007; 14: 20-29.
19 Mendiratta S K, That G, Eslahi N K, Thull N M, Matar M, Bronte V et al. Therapeutic tumor immunity induced by polyimmunization with melanoma antigens gp100 and TRP-2. *Cancer Res* 2001; 61: 859-863.
20 Steitz J, Bruck J, Steinbrink K, Enk A, Knop J, Tuting T. Genetic immunization of mice with human tyrosinase-related protein 2: implications for the immunotherapy of melanoma. *Int J Cancer* 2000; 86: 89-94.
21 Lu Y, Wei Y Q, Tian L, Zhao X, Yang L, Hu B et al. Immunogene therapy of tumors with vaccine based on xenogeneic epidermal growth factor receptor. *J Immunol* 2003; 170: 3162-3170.
22 Wei Y Q, Huang M J, Yang L, Zhao X, Tian L, Lu Y et al. Immunogene therapy of tumors with vaccine based on Xenopus homologous vascular endothelial growth factor as a model antigen. *Proc Natl Acad Sci USA* 2001; 98: 11545-11550.
23 Forconi F, King C A, Sahota S S, Kennaway C K, Russell N H, Stevenson F K. Insight into the potential for DNA idiotypic fusion vaccines designed for patients by analysing xenogeneic anti-idiotypic antibody responses. *Immunology* 2002; 107: 39-45.
24 Weber L W, Bowne W B, Wolchok J D, Srinivasan R, Qin J, Moroi Y et al. Tumor immunity and autoimmunity induced by immunization with homologous DNA. *J Clin Invest* 1998; 102: 1258-1264.
25 Steitz J, Bruck J, Gambotto A, Knop J, Tuting T. Genetic immunization with a melanocytic self-antigen linked to foreign helper sequences breaks tolerance and induces autoimmunity and tumor immunity. *Gene Ther* 2002; 9: 208-213.
26 Johnen H, Kulbe H, Pecher G. Long-term tumor growth suppression in mice immunized with naked DNA of the human tumor antigen mucin (MUC1). *Cancer Immunol Immunother* 2001; 50: 356-360.
27 Su J M, Wei Y Q, Tian L, Zhao X, Yang L, He Q M et al. Active immunogene therapy of cancer with vaccine on the basis of chicken homologous matrix metalloproteinase-2. *Cancer Res* 2003; 63: 600-607.
28 Hawkins W G, Gold J S, Dyall R, Wolchok J D, Hoos A, Bowne W B et al. Immunization with DNA coding for gp100 results in CD4 T-cell independent antitumor immunity. *Surgery* 2000; 128: 273-280.
29 Leitner W W, Hwang L N, deVeer M J, Zhou A, Silverman R H, Williams B R et al. Alphavirus-based DNA vaccine breaks immunological tolerance by activating innate antiviral pathways. Nat Med 2003; 9: 33-39.
30 Niethammer A G, Xiang R, Becker J C, Wodrich H, Pertl U, Karsten G et al. A DNA vaccine against VEGF receptor 2 prevents effective angiogenesis and inhibits tumor growth. *Nat Med* 2002; 8: 1369-1375.
31 Luo Y, Zhou H, Mizutani M, Mizutani N, Reisfeld R A, Xiang R. Transcription factor Fos-related antigen 1 is an effective target for a breast cancer vaccine. *Proc Natl Acad Sci USA* 2003; 100: 8850-8855.
32 Niethammer A G, Primus F J, Xiang R, Dolman C S, Ruehlmann J M, Ba Y et al. An oral DNA vaccine against human carcinoembryonic antigen (CEA) prevents growth and dissemination of Lewis lung carcinoma in CEA transgenic mice. *Vaccine* 2001; 20: 421-429.
33 Xiang R, Lode H N, Chao T H, Ruehlmann J M, Dolman C S, Rodriguez F et al. An autologous oral DNA vaccine protects against murine melanoma. *Proc Natl Acad Sci USA* 2000; 97: 5492-5497.
34 Conejo-Garcia J R, Benencia F, Courreges M C, Kang E, Mohamed-Hadley A, Buckanovich R J et al. Tumor-infiltrating dendritic cell precursors recruited by a beta-defensin contribute to vasculogenesis under the influence of Vegf-A. *Nat Med* 2004; 10: 950-958.
35 Hung C F, Calizo R, Tsai Y C, He L, Wu T C. A DNA vaccine encoding a single-chain trimer of HLA-A2 linked to human mesothelin peptide generates anti-tumor effects against human mesothelin-expressing tumors. *Vaccine* 2007; 25: 127-135.
36 Chen C H, Wang T L, Hung C F, Yang Y, Young R A, Pardoll D M et al. Enhancement of DNA vaccine potency by linkage of antigen gene to an HSP70 gene. *Cancer Res* 2000; 60: 1035-1042.
37 Jasinska J, Wagner S, Radauer C, Sedivy R, Brodowicz T, Wiltschke C et al. Inhibition of tumor cell growth by antibodies induced after vaccination with peptides derived from the extracellular domain of Her-2/neu. *Int J Cancer* 2003; 107: 976-983.

We claim:

1. A composition which induces a CD8$^+$ T cell or CD4$^+$ T cell response, comprising:
    a polypeptide consisting of 9 to 25 contiguous amino acid residues of mesothelin, said polypeptide comprising VLPLTVAEV (SEQ ID NO: 2), wherein said polypeptide induces a CD8$^+$ T cell or CD4$^+$ T-cell response to mesothelin; and
    a carrier for stimulating a CD8$^+$ T cell or CD4$^+$ T cell immune response, wherein the carrier is selected from the group consisting of: (a) a protein that is fused to the polypeptide, said protein selected from the group consisting of CD40, CD40 ligand, OX-40, OX-40 ligand, CTLA-4 antagonist, and GM-CSF, (b) a bacterial cell that is transformed to express the polypeptide, and (c) an antigen presenting cell on whose surface the polypeptide is bound, wherein the composition does not comprise whole tumor cells.

2. The composition of claim 1 which comprises *Listeria monocytogenes* bacteria which express said polypeptide.

3. The composition of claim 1 wherein the carrier is CD40 ligand.

4. The composition of claim 1 wherein the carrier is OX-40 ligand.

5. The composition of claim 1 wherein the carrier is a CTLA-4 antagonist.

6. The composition of claim 1 wherein the carrier is GM-CSF.

7. The composition of claim 1 wherein the carrier is dendritic cells.

* * * * *